(12) United States Patent
Karve et al.

(10) Patent No.: US 12,053,551 B2
(45) Date of Patent: Aug. 6, 2024

(54) PROCESS OF PREPARING mRNA-LOADED LIPID NANOPARTICLES

(71) Applicant: Translate Bio, Inc., Lexington, MA (US)

(72) Inventors: Shrirang Karve, Lexington, MA (US); Frank DeRosa, Lexington, MA (US); Ashish Sarode, Lexington, MA (US); Natalia Vargas Montoya, Lexington, MA (US); Priyal Patel, Lexington, MA (US)

(73) Assignee: TRANSLATE BIO, INC., Waltham, MA (US)

( * ) Notice: Subject to any disclaimer, the term of this patent is extended or adjusted under 35 U.S.C. 154(b) by 200 days.

(21) Appl. No.: 17/129,666

(22) Filed: Dec. 21, 2020

(65) Prior Publication Data

US 2021/0186890 A1 Jun. 24, 2021

Related U.S. Application Data

(60) Provisional application No. 62/951,784, filed on Dec. 20, 2019.

(51) Int. Cl.
| | | |
|---|---|---|
| *A61K 9/51* | (2006.01) | |
| *A61K 31/7105* | (2006.01) | |
| *B82Y 5/00* | (2011.01) | |
| *B82Y 40/00* | (2011.01) | |

(52) U.S. Cl.
CPC ........ *A61K 9/5192* (2013.01); *A61K 31/7105* (2013.01); *B82Y 5/00* (2013.01); *B82Y 40/00* (2013.01)

(58) Field of Classification Search
CPC .... A61K 9/5192; A61K 31/7105; B82Y 5/00; B82Y 40/00
See application file for complete search history.

(56) References Cited

U.S. PATENT DOCUMENTS

| | | | |
|---|---|---|---|
| 4,857,319 A | 8/1989 | Crowe et al. | |
| 5,049,392 A | 9/1991 | Weiner et al. | |
| 7,094,423 B1 | 8/2006 | Maurer et al. | |
| 2002/0119990 A1* | 8/2002 | Madden ............... | A61K 9/1272 514/283 |
| 2014/0206753 A1 | 7/2014 | Guild et al. | |
| 2015/0110857 A1 | 4/2015 | DeRosa et al. | |
| 2018/0125989 A1 | 5/2018 | DeRosa et al. | |
| 2018/0153822 A1* | 6/2018 | Karve ............ | C12Y 603/04005 |

FOREIGN PATENT DOCUMENTS

| | | |
|---|---|---|
| EP | 3020701 A1 | 5/2016 |
| WO | WO 1993/03709 A1 | 3/1993 |
| WO | WO 2001/005375 A1 | 1/2001 |
| WO | WO 2014/144196 A1 | 9/2014 |
| WO | WO 2015/128030 A1 | 9/2015 |
| WO | WO 2016/004318 A1 | 1/2016 |
| WO | WO 2018/089801 A1 | 5/2018 |
| WO | WO 2019/207060 A1 | 10/2019 |
| WO | WO 2021/007278 A1 | 1/2021 |

OTHER PUBLICATIONS

Cullis et al., Molecular Therapy vol. 25 No. 7, Jul. 2017, 1467-1475 (Year: 2017).*
Alton, E. et al., "A randomised, double-blind, placebo-controlled trial of repeated nebulisation of non-viral cystic fibrosis transmembrane conductance regulator (CFTR) gene therapy in patients with cystic fibrosis," Efficacy and Mechanism Evaluation, Jul. 2016, vol. 3, No. 5, ISSN 2050-4365.
Avnir et al., Amphipathic Weak Acid Glucocorticoid Prodrugs Remote-Loaded Into Sterically Stabilized Nanoliposomes Evaluated in Arthritic Rats and in a Beagle Dog, Arthritis & Rheumatism, vol. 58, No. 1, Jan. 2008, pp. 119-129.
Belliveau et al., "Microfluidic Synthesis of Highly Potent Limit-Size Lipid Nanoparticles for In Vivo Delivery of siRNA", Molecular Therapy-Nucleic Acids (2012) 1, e37.
Buyens et al., "Liposome based systems for systemic siRNA delivery: Stability in blood sets the requirements for optimal carrier design", Journal of Controlled Release 158 (2012) 362-370.
De Cock et al., "Sonoprinting and the importance of microbubble loading for ultrasound mediated cellular delivery nanoparticles", Biomaterials 83 (2016) 294-307.
Fenske et al., "Entrapment of Small Molecules and Nucleic Acid-Based Drugs in Liposomes", Methodology of Liposome Drug Delivery Systems, 2008, 5(1): 25-44.
Fritze et al., "Remote loading of doxorubicin into liposomes driven by a transmembrane phosphate gradient", Biochimica et Biophysica Acta 2006, 1758: 1633-1640.
Gibco Optimem. Product Information, 2001.
Gjetting et al., "A simple protocol for preparation of a liposomal vesicle with encapsulated plasmid DNA that mediate high accumulation and reporter gene activity in tumor tissue", Results in Pharma Sciences 1 (2011) 49-56.
Hayes et al., "Genospheres: self-assembling nucleic acid-lipid nanoparticles suitable for targeted gene delivery", Gene Therapy (2006) 13, 646-651.
Hood et al., "Microfluidic remote loading for rapid single-step liposomal drug preparation", Lab on a Chip, 2014, 14: 3359-3367.
International Search Report for PCT/US17/61113, 5 pages, (dated Mar. 2, 2018).
International Search Report for PCT/US20/66431, 5 pages, (dated Apr. 6, 2021).
Jeffs et al., "A Scalable, Extrusion-Free Method for Efficient Liposomal Encapsulation of Plasmid DNA", Pharmaceutical Research, vol. 22, No. 3, Mar. 2005.

(Continued)

Primary Examiner — Robert S Cabral
(74) Attorney, Agent, or Firm — LATHROP GPM LLP; James H. Velema, Esq.

(57) ABSTRACT

The present invention provides an improved process for lipid nanoparticle formulation and mRNA encapsulation. In some embodiments, the present invention provides a process of encapsulating messenger RNA (mRNA) in lipid nanoparticles comprising a step of combining a solution of preformed lipid nanoparticles with lipid nanoparticles encapsulating mRNA, resulting in a composition of increased potency of mRNA encoded protein expression in vivo.

2 Claims, 7 Drawing Sheets

(56) References Cited

OTHER PUBLICATIONS

Kauffman et al., "Optimization of Lipid Nanoparticle Formulations for mRNA Delivery in Vivo with Fractional Factorial and Definitive Screening Designs", Nano Letters 2015, 15, 7300-7306 (2015).

Kubota et al., "Effect of the nanoformulation of siRNA-lipid assemblies on their cellular uptake and immune stimulation", International Journal of Nanomedicine, 12, 5121-5133 (2017).

Leung et al., "Lipid Nanoparticles Containing siRNA Synthesized by Microfluidic Mixing Exhibit an Electron-Dense Nanostructured Core", The Journal of Physical Chemistry (2012) 116: 18440-18450.

Maurer et al., "Spontaneous Entrapment of Polynucleotides upon Electrostatic Interaction with Ethanol-Destabilized Cationic Liposomes", Biophysical Journal, vol. 80, 2310-2326 (May 2001).

Martinon et al., "Induction of virus-specific cytotoxic T lymphocytes in vivo by liposome-entrapped mRNA", European Journal of Immunology, 1993, 23: 1719-1722.

Rejman et al., "mRNA transfection of cervical carcinoma and mesenchymal stem cells mediated by cationic carriers", Journal of Controlled Release, 2010, 147: 385-391.

Wan et al., "Lipid nanoparticle delivery systems for siRNA-based therapeutics", Drug Delivery and Translational Research (2014) 4:74-83.

Wang et al., Encapsulating Protein into Preformed Liposomes by Ethanol-Destabilized Method, Artificial Cells, Blood Substitutes, and Biotechnology, 31:3, 303-312 (2003).

Wang et al., Systemic Delivery of Modified mRNA Encoding Herpes Simplex Virus 1 Thymidine Kinase for Targeted Cancer Gene Therapy, The American Society of Gene & Cell Therapy, 2013, 21(2):358-367.

"Overview of Transfection", Mar. 18, 2016, retrieved from URL: https://web.archive.org/web/20160318192804/https://www.mirusbio.com/transfectopedia/methods, submitted as Exhibit C (7 pages).

* cited by examiner

PROCESS OF PREPARING mRNA-LOADED LIPID NANOPARTICLES

CROSS-REFERENCE TO RELATED APPLICATIONS

This application claims priority to, and the benefit of, U.S. provisional application No. 62/951,784, filed on Dec. 20, 2019, the contents of which is hereby incorporated by reference in its entirety.

BACKGROUND

Messenger RNA therapy (MRT) is becoming an increasingly important approach for the treatment of a variety of diseases. MRT involves administration of messenger RNA (mRNA) to a patient in need of the therapy for production of the protein encoded by the mRNA within the patient's body. Lipid nanoparticles are commonly used to encapsulate mRNA for efficient in vivo delivery of mRNA.

To improve lipid nanoparticle delivery, much effort has focused on identifying novel methods and compositions that can affect intracellular delivery and/or expression of mRNA, and can be adaptable to a scalable and cost-effective manufacturing process. In addition, due consideration is now being given to the safety and tolerability of the compositions associated with lipid mediated mRNA delivery. Recent reports suggest an inverse relationship between potency and tolerability of liposome (Roursgaard M. et al., Toxicology In Vitro, 2016, 36: 164-171). Therefore it is necessary to achieve the right balance between safety and efficacy in designing a successful therapeutic. However, existing approaches need considerable improvement to meet these requirements.

SUMMARY OF INVENTION

The present invention provides, among other things, an improved process for preparing a composition comprising mRNA-loaded lipid nanoparticles (mRNA-LNPs). The invention is based on the surprising discovery that an mRNA-LNP composition of the invention induces much higher protein expression in vivo than the mRNA-LNP compositions previously known. The invention provides, among other things, a process (referred to as Process C) for preparing a composition comprising mRNA-LNPs, comprising the steps: (a) mixing preformed empty LNPs with mRNA to form the mRNA-LNPs, and (b) combining the mRNA-LNPs generated in step (a) with preformed lipid nanoparticles to form an mRNA-LNP composition. The step (a) of Process C is also referred to as Process B, as described in US 2018/0153822, which is incorporated by reference in its entirety.

In certain embodiments, the preformed lipid nanoparticles which are combined with mRNA-LNPs in step (b) are empty LNPs. In some embodiments, the preformed lipid nanoparticles which are combined with mRNA-LNPs in step (b) are identical to the empty LNPs in step (a).

Applicant found that the mRNA-LNP composition generated by the method described herein is significantly potent, i.e. resulted in much higher protein expression in vivo as compared to traditionally formed mRNA-LNPs, which are prepared in general, by mixing lipids with mRNA. Applicant also found that the mRNA-LNP composition generated by the method described herein is significantly potent as compared to mRNA-LNPs formed using step (a) alone (Process B). Furthermore, the mRNA-LNP composition generated by the method described herein has higher or comparable tolerability despite significantly higher potency. Therefore, in one embodiment, because of the higher potency of the mRNA-LNP composition the improved process of the invention allows administration of lower amounts of mRNA to the subject in order to obtain a therapeutic benefit of mRNA. In one embodiment, the mRNA-LNP composition formed by the improved method of the invention exhibits comparable in vivo tolerability as mRNA-LNPs generated for example in step (a) alone. In some embodiments, the in vivo tolerability is determined by induction of liver tolerability marker enzymes aspartate transaminase (AST) and/or alanine aminotransferase (ALT). Therefore, in one embodiment, the LNP composition formed by the invention described herein exhibits higher tolerability (i.e. lower AST and/or ALT level) than previously known mRNA-LNPs.

The present invention is particularly useful for manufacturing mRNA-LNPs using lower amounts of mRNA for therapeutic use, thereby increasing the therapeutic index (t.i.) of the mRNA therapeutic product.

Thus, in one aspect, the present invention provides a method of manufacturing lipid nanoparticles encapsulating mRNA, comprising the steps: (a) mixing a solution comprising preformed empty lipid nanoparticles and mRNA such that lipid nanoparticles encapsulating mRNA (mRNA-LNPs) are formed, and (b) combining the mRNA-LNPs formed in step (a) with preformed LNPs, resulting in the composition comprising mRNA-LNPs. In some embodiments, the preformed LNPs in step (b) are empty LNPs, that is, they do not comprise any mRNA or other polynucleotides.

In some embodiments, the preformed empty LNPs in step (a) and the preformed LNPs in step (b) have the same lipid formulation. In some embodiments, the preformed empty LNPs in step (a) and the preformed LNPs in step (b) have the different lipid formulation. In some embodiments, the preformed empty LNPs in step (a) and the preformed LNPs in step (b) comprise same cationic lipids. In some embodiments, the preformed empty LNPs in step (a) and the preformed LNPs in step (b) comprise the different cationic lipids. In some embodiments, the preformed empty LNPs in step (a) and/or the preformed LNPs in step (b) do not contain a cationic lipid. In some embodiments, the preformed LNPs in step (b) do not contain a cationic lipid.

In some embodiments, the preformed empty LNPs in step (a) and the preformed empty LNPs in step (b) comprise the same lipids combined in the same ratios in the LNP. In some embodiments, the preformed empty LNPs in step (a) and the preformed empty LNPs in step (b) comprise the same lipids but combined in different ratios in the LNP. In some embodiments, the preformed empty LNPs in step (a) and the preformed empty LNPs in step (b) comprise different lipids other than cationic lipids. In some embodiments, the preformed empty LNPs in step (a) and the preformed empty LNPs in step (b) comprise same lipids other than cationic lipids. In some embodiments, the preformed empty LNPs in step (a) and the preformed empty LNPs in step (b) comprise different lipids.

In some embodiments, the preformed empty LNPs in step (a) and/or the preformed empty LNPs in step (b) comprise one or more cationic lipids, one or more non-cationic lipids and one or more PEG-modified lipids. In some embodiments, the preformed empty LNPs in step (a) and/or the preformed empty LNPs in step (b) comprise one or more neutral lipids and one or more PEG-modified lipids. In some embodiments, the preformed empty LNPs in step (a) and/or the preformed empty LNPs in step (b) further comprise one or more cholesterol-based lipids.

In some embodiments, the method further comprises a step of first mixing lipids to form empty LNPs prior to step (a) and/or step (b).

In some embodiments, the mRNA-LNPs and the preformed LNPs are combined in step (b) at a ratio ranging from 20:1 to 1:20, from 10:1 to 1:10, from 5:1 to 1:5, from 3:1 to 1:3, or from 2:1 to 1:2. In some embodiments, the mRNA-LNPs and the preformed LNPs are combined in step (b) at a ratio of or greater than 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, or 1:20.

In some embodiments, the mRNA-LNPs and the empty LNPs each have an average size ranging from about 75-150 nm in diameter. In some embodiments, the mRNA-LNPs and the preformed LNPs each have an average size of less than 100 nm in diameter. In some embodiments, the composition has a ratio of total lipids to total mRNA ranging from 20:1 to 1:1, from 10:1 to 1:1, from 5:1 to 1:1, from 5:1 to 2:1, or from 4:1 to 2:1, or greater than 1:1, 2:1, 3:1, 4:1, 5:1, 6:1, 7:1, 8:1, 9:1, 10:1, 12:1, 15:1, or 20:1.

In some embodiments, the composition comprising lipid nanoparticles has an N/P ratio of about 1, about 2, about 3, about 4, about 5, about 6, about 7, about 8, about 9, about 10, about 11, about 12, about 13, about 14, about 15, about 16, about 17, about 18 about 19 or about 20. Accordingly, in some embodiments, the composition comprising lipid nanoparticles has an N/P ratio of about 1. In some embodiments, the composition comprising lipid nanoparticles has an N/P ratio of about 2. In some embodiments, the composition comprising lipid nanoparticles has an N/P ratio of about 3. In some embodiments, the composition comprising lipid nanoparticles has an N/P ratio of about 4. In some embodiments, the composition comprising lipid nanoparticles has an N/P ratio of about 5. In some embodiments, the composition comprising lipid nanoparticles has an N/P ratio of about 6. In some embodiments, the composition comprising lipid nanoparticles has an N/P ratio of about 7. In some embodiments, the composition comprising lipid nanoparticles has an N/P ratio of about 8. In some embodiments, the composition comprising lipid nanoparticles has an N/P ratio of about 9. In some embodiments, the composition comprising lipid nanoparticles has an N/P ratio of about 10. In some embodiments, the composition comprising lipid nanoparticles has an N/P ratio of about 11. In some embodiments, the composition comprising lipid nanoparticles has an N/P ratio of about 12. In some embodiments, the composition comprising lipid nanoparticles has an N/P ratio of about 13. In some embodiments, the composition comprising lipid nanoparticles has an N/P ratio of about 14. In some embodiments, the composition comprising lipid nanoparticles has an N/P ratio of about 15. In some embodiments, the composition comprising lipid nanoparticles has an N/P ratio of about 16. In some embodiments, the composition comprising lipid nanoparticles has an N/P ratio of about 17. In some embodiments, the composition comprising lipid nanoparticles has an N/P ratio of about 18. In some embodiments, the composition comprising lipid nanoparticles has an N/P ratio of about 19. In some embodiments, the composition comprising lipid nanoparticles has an N/P ratio of about 20.

In some embodiments, the composition comprising lipid nanoparticles has an N/P ratio of between about 1 to about 7. In some embodiments, the composition comprising lipid nanoparticles has an N/P ratio of between about 1 to about 6. In some embodiments, the composition comprising lipid nanoparticles has an N/P ratio of between about 1 to about 5. In some embodiments, the composition comprising lipid nanoparticles has an N/P ratio of between about 1 to about 4. In some embodiments, the composition comprising lipid nanoparticles has an N/P ratio of between about 1 to about 3. In some embodiments, the composition comprising lipid nanoparticles has an N/P ratio of between about 1 to about 2. In some embodiments, the composition comprising lipid nanoparticles has an N/P ratio of between about 2 to between about 7. In some embodiments, the composition comprising lipid nanoparticles has an N/P ratio of between about 2 to between about 6. In some embodiments, the composition comprising lipid nanoparticles has an N/P ratio of between about 2 to between about 5. In some embodiments, the composition comprising lipid nanoparticles has an N/P ratio of between about 2 to between about 4. In some embodiments, the composition comprising lipid nanoparticles has an N/P ratio of between about 2 to between about 3. In some embodiments, the composition comprising lipid nanoparticles has an N/P ratio of between about 3 to between about 7. In some embodiments, the composition comprising lipid nanoparticles has an N/P ratio of between about 3 to between about 6. In some embodiments, the composition comprising lipid nanoparticles has an N/P ratio of between about 3 to between about 5. In some embodiments, the composition comprising lipid nanoparticles has an N/P ratio of between about 3 to between about 4. In some embodiments, the composition comprising lipid nanoparticles has an N/P ratio of between about 4 to between about 7. In some embodiments, the composition comprising lipid nanoparticles has an N/P ratio of between about 4 to between about 6. In some embodiments, the composition comprising lipid nanoparticles has an N/P ratio of between about 4 to between about 5. In some embodiments, the composition comprising lipid nanoparticles has an N/P ratio of between about 5 to between about 7. In some embodiments, the composition comprising lipid nanoparticles has an N/P ratio of between about 5 to between about 6. In some embodiments, the composition comprising lipid nanoparticles has an N/P ratio of between about 6 to between about 7.

The N/P ratio can be achieved in various manners. For example, in some embodiments, a method of manufacturing a composition comprising lipid nanoparticles encapsulating mRNA (mRNA-LNPs) comprises (a) mixing preformed empty lipid nanoparticles (LNPs) with mRNA under conditions that allow formation of mRNA-LNPs at an N/P ratio of about 2; and (b) combining the mRNA-LNPs formed in step (a) with preformed LNPs at an N/P ratio of about 2, resulting in the composition comprising mRNA-LNPs at an N/P ratio of about 4. In other embodiments, a method of manufacturing a composition comprising lipid nanoparticles encapsulating mRNA (mRNA-LNPs) comprises (a) mixing preformed empty lipid nanoparticles (LNPs) with mRNA under conditions that allow formation of mRNA-LNPs at an N/P ratio of about 2; and (b) combining the mRNA-LNPs formed in step (a) with preformed LNPs at an N/P ratio of about 4, resulting in the composition comprising mRNA-LNPs at an N/P ratio of about 6. In further embodiments, a method of manufacturing a composition comprising lipid nanoparticles encapsulating mRNA (mRNA-LNPs) comprises (a) mixing preformed empty lipid nanoparticles (LNPs) with mRNA under conditions that allow formation of mRNA-LNPs at an N/P ratio of about 4; and (b) combining the mRNA-LNPs formed in step (a) with preformed LNPs at an N/P ratio of about 2, resulting in the composition comprising mRNA-LNPs at an N/P ratio of about 6. In some embodiments, the composition comprising lipid nanoparticles formed in step (a) of FIG. 1 has an N/P ratio of about 1, about 2, about 3, about 4, about 5, about 6, or about 7, about 8, about 9, about 10, about 11, about 12, about 13, about 14, about 15, about 16, about 17, about 18, about 19 or about 20. Accordingly, in some embodiments, the composition comprising lipid nanoparticles formed in step (a) has an N/P ratio of about 1. In some embodiments, the composition comprising lipid nanoparticles formed in step (a) has an N/P ratio of about 2. In some embodiments, the composition comprising lipid nanoparticles formed in step (a) has an N/P ratio of about 3. In some embodiments, the composition comprising lipid nanoparticles formed in step (a) has an N/P ratio of about 4. In some embodiments, the composition comprising lipid nanoparticles formed in step (a) has an N/P ratio of about 5. In some embodiments, the composition comprising lipid nanoparticles formed in step (a) has an N/P ratio of about 6. In some embodiments, the composition comprising lipid nanoparticles formed in step (a) has an N/P ratio of about 7. In some embodiments, the composition comprising lipid nanoparticles formed in step (a) has an N/P ratio of about 8. In some embodiments, the composition comprising lipid nanoparticles formed in step (a) has an N/P ratio of about 9. In some embodiments, the composition comprising lipid nanoparticles formed in step (a) has an N/P ratio of about 10. In some embodiments, the composition comprising lipid nanoparticles formed in step (a) has an N/P ratio of about 11. In some embodiments, the composition comprising lipid nanoparticles formed in step (a) has an N/P ratio of about 12. In some embodiments, the composition comprising lipid nanoparticles formed in step (a) has an N/P ratio of about 13. In some embodiments, the composition comprising lipid nanoparticles formed in step (a) has an N/P ratio of about 14. In some embodiments, the composition comprising lipid nanoparticles formed in step (a) has an N/P ratio of about 15. In some embodiments, the composition comprising lipid nanoparticles formed in step (a) has an N/P ratio of about 16. In some embodiments, the composition comprising lipid nanoparticles formed in step (a) has an N/P ratio of about 17. In some embodiments, the composition comprising lipid nanoparticles formed in step (a) has an N/P ratio of about 18. In some embodiments, the composition comprising lipid nanoparticles formed in step (a) has an N/P ratio of about 19. In some embodiments, the composition comprising lipid nanoparticles formed in step (a) has an N/P ratio of about 20.

In some embodiments, the composition comprising lipid nanoparticles formed in step (b) of FIG. 1 has an N/P ratio of about 1, about 2, about 3, about 4, about 5, about 6, about 7, about 8, about 9, about 10, about 11, about 12, about 13, about 14, about 15, about 16, about 17, about 18, about 19 or about 20. Accordingly, in some embodiments, the composition comprising lipid nanoparticles formed in step (b) has an N/P ratio of about 1. In some embodiments, the composition comprising lipid nanoparticles formed in step (b) has an N/P ratio of about 3. In some embodiments, the composition comprising lipid nanoparticles formed in step (b) has an N/P ratio of about 4. In some embodiments, the composition comprising lipid nanoparticles formed in step (b) has an N/P ratio of about 5. In some embodiments, the composition comprising lipid nanoparticles formed in step (b) has an N/P ratio of about 6. In some embodiments, the composition comprising lipid nanoparticles formed in step (b) has an N/P ratio of about 7. In some embodiments, the composition comprising lipid nanoparticles formed in step (b) has an N/P ratio of about 8. In some embodiments, the composition comprising lipid nanoparticles formed in step (b) has an N/P ratio of about 9. In some embodiments, the composition comprising lipid nanoparticles formed in step (b) has an N/P ratio of about 10. In some embodiments, the composition comprising lipid nanoparticles formed in step (b) has an N/P ratio of about 11. In some embodiments, the composition comprising lipid nanoparticles formed in step (b) has an N/P ratio of about 12. In some embodiments, the composition comprising lipid nanoparticles formed in step (b) has an N/P ratio of about 13. In some embodiments, the composition comprising lipid nanoparticles formed in step (b) has an N/P ratio of about 14. In some embodiments, the composition comprising lipid nanoparticles formed in step (b) has an N/P ratio of about 15. In some embodiments, the composition comprising lipid nanoparticles formed in step (b) has an N/P ratio of about 16. In some embodiments, the composition comprising lipid nanoparticles formed in step (b) has an N/P ratio of about 17. In some embodiments, the composition comprising lipid nanoparticles formed in step (b) has an N/P ratio of about 18. In some embodiments, the composition comprising lipid nanoparticles formed in step (b) has an N/P ratio of about 19. In some embodiments, the composition comprising lipid nanoparticles formed in step (b) has an N/P ratio of about 20.

In some embodiments, the mRNA in lipid nanoparticles is present at a concentration of 5 mg/ml, 4 mg/ml, 3 mg/ml, 2 mg/ml, 1 mg/ml, 0.9 mg/ml, 0.8 mg/ml, 0.7 mg/ml, 0.6 mg/ml, 0.5 mg/ml, 0.4 mg/ml, 0.3 mg/ml, 0.25 mg/ml, 0.2 mg/ml, 0.15 mg/ml, 0.1 mg/ml, 0.05 mg/ml, or 0.01 mg/ml.

In some embodiments, the mRNA is present in the solution at a concentration of no greater than 3 mg/ml, 2 mg/ml, 1 mg/ml, 0.9 mg/ml, 0.85 mg/ml, 0.8 mg/ml, 0.75 mg/ml, 0.7 mg/ml, 0.65 mg/ml, 0.6 mg/ml, 0.55 mg/ml, 0.5 mg/ml, 0.45 mg/ml, 0.4 mg/ml, 0.35 mg/ml, 0.3 mg/ml, 0.25 mg/ml, 0.2 mg/ml, 0.15 mg/ml, 0.1 mg/ml, 0.05 mg/ml, or 0.01 mg/ml.

In some embodiments, the preformed lipid nanoparticles are formed by mixing lipids dissolved in ethanol with an aqueous solution.

In one aspect, the invention provides a composition comprising lipid nanoparticles encapsulating mRNA (mRNA-LNPs) manufactured according to a method of the invention. In some embodiments, the composition comprises a combination of lipid nanoparticles encapsulating mRNA (mRNA-LNPs) and empty lipids nanoparticles (LNPs), wherein the mRNA-LNPs and the empty LNPs comprise the same cationic lipids. In some embodiments, the mRNA-LNPs and the empty LNPs have a same lipid formulation. In some embodiments, the mRNA-LNPs and the empty LNPs have a different lipid formulation.

In some aspects, the invention provides a composition comprising lipid nanoparticles encapsulating mRNA (mRNA-LNPs) and empty lipids nanoparticles (LNPs), wherein the mRNA-LNPs and/or the empty LNPs do not contain a cationic lipid. In some embodiments, the empty LNPs do not contain a cationic lipid. In some embodiments, the empty LNPs do not contain a cationic lipid. In some embodiments, the mRNA-LNPs and/or the empty LNPs comprise one or more cationic lipids, one or more neutral lipids, and one or more PEG-modified lipids. In some embodiments, the mRNA-LNPs and/or the empty LNPs comprise one or more neutral lipids and one or more PEG-modified lipid. In some embodiments, the mRNA-LNPs and/or the empty LNPs further comprise one or more cholesterol based lipids.

In some embodiments, the mRNA-LNPs and the empty LNPs are present at a ratio ranging from 20:1 to 1:20, from 10:1 to 1:10, from 5:1 to 1:5, from 3:1 to 1:3, or from 2:1 to 1:2. In some embodiments, the mRNA-LNPs and the empty LNPs are present at a ratio of or greater than 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, or 1:20.

In some embodiments, the mRNA-LNPs and the empty LNPs each have an average size ranging from about 75-150 nm in diameter. In some embodiments, the mRNA-LNPs and the empty LNPs each have an average size of less than 100 nm in diameter.

In some embodiment, the composition has a ratio of total amount of mRNA to total amount of lipids ranging from 20:1 to 1:1, from 10:1 to 1:1, from 5:1 to 1:1, from 5:1 to 2:1, or from 4:1 to 2:1, or greater than 1:1, 2:1, 3:1, 4:1, 5:1, 6:1, 7:1, 8:1, 9:1, 10:1, 12:1, 15:1, or 20:1.

In some embodiments, the mRNA encodes a protein or a peptide.

In one aspect, the invention provides a method of delivering mRNA for in vivo protein expression, comprising administering to a subject a composition of the invention as described in the preceding paragraphs.

In some embodiments, expression level of the protein or peptide encoded by the mRNA following administering the composition to the subject is increased as compared to the expression level of the protein or peptide encoded by the same amount of mRNA administered with identical mRNA-LNPs but without the empty LNPs, with comparable expression level of liver enzyme aspartate transaminase (AST) and/or alanine aminotransferase (ALT).

In some embodiments, the expression level of the protein or peptide is increased by at least 20%, 40%, 50%, 60%, 70%, 80%, 90%, 1-fold, 1.5-fold, 2-fold, 3-fold, 4-fold, or 5-fold.

In one aspect, the invention provides a method for manufacturing an mRNA composition for therapeutic use, the method comprising lipid nanoparticles encapsulating mRNA (mRNA-LNPs), the method comprising: (a) dividing a stock of preformed empty lipid nanoparticles into two portions; (b) mixing a first portion of preformed empty lipid nanoparticles (LNPs) with mRNA under conditions that allow formation of mRNA-LNPs; (c) combining the mRNA-LNPs formed in step (b) with the second portion of the empty LNPs in step (a), resulting in the composition comprising mRNA-LNPs.

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

DEFINITIONS

Figure 1:
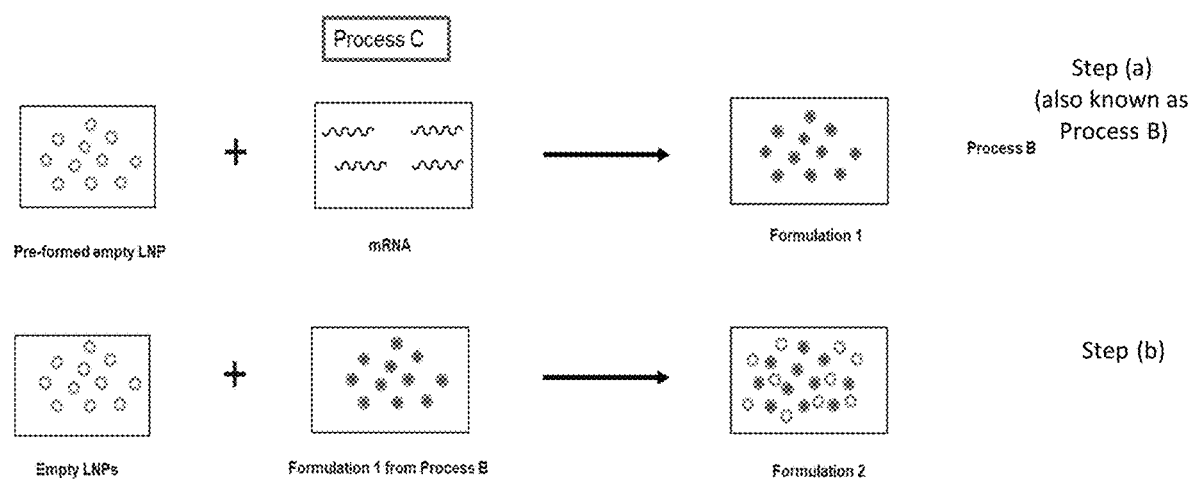
FIG. 1 is an exemplary schematic representation of Process C. Process C comprises a step (a) and a step (b) for generating a composition comprising mRNA and LNP of high potency. Step (a) of Process C is also referred to as Process B.

In order for the present invention to be more readily understood, certain terms are first defined below. Additional definitions for the following terms and other terms are set forth throughout the specification. The publications and other reference materials referenced herein to describe the background of the invention and to provide additional detail regarding its practice are hereby incorporated by reference.

Amino acid: As used herein, the term "amino acid," in its broadest sense, refers to any compound and/or substance that can be incorporated into a polypeptide chain. In some embodiments, an amino acid has the general structure $H_2N$—C(H)(R)—COOH. In some embodiments, an amino acid is a naturally occurring amino acid. In some embodiments, an amino acid is a synthetic amino acid; in some embodiments, an amino acid is a d-amino acid; in some embodiments, an amino acid is an l-amino acid. "Standard amino acid" refers to any of the twenty standard l-amino acids commonly found in naturally occurring peptides. "Nonstandard amino acid" refers to any amino acid, other than the standard amino acids, regardless of whether it is prepared synthetically or obtained from a natural source. As used herein, "synthetic amino acid" encompasses chemically modified amino acids, including but not limited to salts, amino acid derivatives (such as amides), and/or substitutions. Amino acids, including carboxy- and/or amino-terminal amino acids in peptides, can be modified by methylation, amidation, acetylation, protecting groups, and/or substitution with other chemical groups that can change the peptide's circulating half-life without adversely affecting their activity. Amino acids may participate in a disulfide bond. Amino acids may comprise one or posttranslational modifications, such as association with one or more chemical entities (e.g., methyl groups, acetate groups, acetyl groups, phosphate groups, formyl moieties, isoprenoid groups, sulfate groups, polyethylene glycol moieties, lipid moieties, carbohydrate moieties, biotin moieties, etc.). The term "amino acid" is used interchangeably with "amino acid residue," and may refer to a free amino acid and/or to an amino acid residue of a peptide. It will be apparent from the context in which the term is used whether it refers to a free amino acid or a residue of a peptide.

Animal: As used herein, the term "animal" refers to any member of the animal kingdom. In some embodiments, "animal" refers to humans, at any stage of development. In some embodiments, "animal" refers to non-human animals, at any stage of development. In certain embodiments, the non-human animal is a mammal (e.g., a rodent, a mouse, a rat, a rabbit, a monkey, a dog, a cat, a sheep, cattle, a primate, and/or a pig). In some embodiments, animals include, but are not limited to, mammals, birds, reptiles, amphibians, fish, insects, and/or worms. In some embodiments, an animal may be a transgenic animal, genetically-engineered animal, and/or a clone.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Combining: As used herein, the term "combining" is interchangeably used with mixing or blending. Combining refers to putting together discrete LNP particles having distinct properties in the same solution, for example, combining an mRNA-LNP and an empty LNP, to obtain an mRNA-LNP composition. In some embodiments, the combining of the two LNPs is performed at a specific ratio of the components being combined. In some embodiments, the resultant composition obtained from the combining has a property distinct from any one or both of its components.

Delivery: As used herein, the term "delivery" encompasses both local and systemic delivery. For example, delivery of mRNA encompasses situations in which an mRNA is delivered to a target tissue and the encoded protein is expressed and retained within the target tissue (also referred to as "local distribution" or "local delivery"), and situations in which an mRNA is delivered to a target tissue and the encoded protein is expressed and secreted into patient's circulation system (e.g., serum) and systematically distributed and taken up by other tissues (also referred to as "systemic distribution" or "systemic delivery"). In some embodiments, delivery is pulmonary delivery, e.g., comprising nebulization.

Efficacy: As used herein, the term "efficacy," or grammatical equivalents, refers to an improvement of a biologically relevant endpoint, as related to delivery of mRNA that encodes a relevant protein or peptide. In some embodiments, the biological endpoint is protecting against an ammonium chloride challenge at certain time points after administration.

Encapsulation: As used herein, the term "encapsulation," or its grammatical equivalent, refers to the process of confining a nucleic acid molecule within a nanoparticle.

Expression: As used herein, "expression" of a nucleic acid sequence refers to translation of an mRNA into a polypeptide, assemble multiple polypeptides (e.g., heavy chain or light chain of antibody) into an intact protein (e.g., antibody) and/or post-translational modification of a polypeptide or fully assembled protein (e.g., antibody). In this application, the terms "expression" and "production," and their grammatical equivalents, are used interchangeably.

Improve, increase, or reduce: As used herein, the terms "improve," "increase" or "reduce," or grammatical equivalents, indicate values that are relative to a baseline measurement, such as a measurement in the same individual prior to initiation of the treatment described herein, or a measurement in a control subject (or multiple control subject) in the absence of the treatment described herein. A "control subject" is a subject afflicted with the same form of disease as the subject being treated, who is about the same age as the subject being treated.

Impurities: As used herein, the term "impurities" refers to substances inside a confined amount of liquid, gas, or solid, which differ from the chemical composition of the target material or compound. Impurities are also referred to as contaminants.

In Vitro: As used herein, the term "in vitro" refers to events that occur in an artificial environment, e.g., in a test tube or reaction vessel, in cell culture, etc., rather than within a multi-cellular organism.

In Vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" refers to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from about 10%, about 20%, about 30%, about 40%, about 50%, about 60%, about 70%, about 80%, about 90%, about 91%, about 92%, about 93%, about 94%, about 95%, about 96%, about 97%, about 98%, about 99%, or more than about 99% of the other components with which they were initially associated. In some embodiments, isolated agents are about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. As used herein, calculation of percent purity of isolated substances and/or entities should not include excipients (e.g., buffer, solvent, water, etc.).

Liposome: As used herein, the term "liposome" refers to any lamellar, multilamellar, or solid nanoparticle vesicle. Typically, a liposome as used herein can be formed by mixing one or more lipids or by mixing one or more lipids and polymer(s). In some embodiments, a liposome suitable for the present invention contains a cationic lipids(s) and optionally non-cationic lipid(s), optionally cholesterol-based lipid(s), and/or optionally PEG-modified lipid(s).

Local distribution or delivery: As used herein, the terms "local distribution," "local delivery," or grammatical equivalent, refer to tissue specific delivery or distribution. Typically, local distribution or delivery requires a peptide or protein (e.g., enzyme) encoded by mRNAs be translated and expressed intracellularly or with limited secretion that avoids entering the patient's circulation system.

messenger RNA (mRNA): As used herein, the term "messenger RNA (mRNA)" refers to a polynucleotide that encodes at least one peptide, polypeptide or protein. mRNA as used herein encompasses both modified and unmodified RNA. mRNA may contain one or more coding and non-coding regions. mRNA can be purified from natural sources, produced using recombinant expression systems and optionally purified, chemically synthesized, etc. Where appropriate, e.g., in the case of chemically synthesized molecules, mRNA can comprise nucleoside analogs such as analogs having chemically modified bases or sugars, backbone modifications, etc. An mRNA sequence is presented in the 5' to 3' direction unless otherwise indicated. In some embodiments, an mRNA is or comprises natural nucleosides (e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, 2-thiocytidine, pseudouridine, and 5-methylcytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

N/P Ratio: As used herein, the term "N/P ratio" refers to a molar ratio of positively charged molecular units in the cationic lipids in a lipid nanoparticle relative to negatively charged molecular units in the mRNA encapsulated within that lipid nanoparticle. As such, N/P ratio can be calculated as the ratio of moles of cationic lipids in a lipid nanoparticle relative to moles of phosphate groups in mRNA encapsulated within that lipid nanoparticle. In some embodiments in which a cationic lipid molecule includes more than one ionizable group, such as more than one amine group, N/P ratio can be calculated as the ratio of moles of ionizable groups (e.g., such as the number of amine groups) of the cationic lipids in a lipid nanoparticle relative to moles of phosphate groups in mRNA encapsulated within that lipid nanoparticle.

Nucleic acid: As used herein, the term "nucleic acid," in its broadest sense, refers to any compound and/or substance that is or can be incorporated into a polynucleotide chain. In some embodiments, a nucleic acid is a compound and/or substance that is or can be incorporated into a polynucleotide chain via a phosphodiester linkage. In some embodiments, "nucleic acid" refers to individual nucleic acid residues (e.g., nucleotides and/or nucleosides). In some embodiments, "nucleic acid" refers to a polynucleotide chain comprising individual nucleic acid residues. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery. In some embodiments, the nucleotides T and U are used interchangeably in sequence descriptions.

Patient: As used herein, the term "patient" or "subject" refers to any organism to which a provided composition may be administered, e.g., for experimental, diagnostic, prophylactic, cosmetic, and/or therapeutic purposes. Typical patients include animals (e.g., mammals such as mice, rats, rabbits, non-human primates, and/or humans). In some embodiments, a patient is a human. A human includes pre- and post-natal forms.

Pharmaceutically acceptable: The term "pharmaceutically acceptable" as used herein, refers to substances that, within the scope of sound medical judgment, are suitable for use in contact with the tissues of human beings and animals without excessive toxicity, irritation, allergic response, or other problem or complication, commensurate with a reasonable benefit/risk ratio.

Pharmaceutically acceptable salt: Pharmaceutically acceptable salts are well known in the art. For example, S. M. Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\,alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counter ions such as halide, hydroxide, carboxylate, sulfate, phosphate, nitrate, sulfonate and aryl sulfonate. Further pharmaceutically acceptable salts include salts formed from the quaternization of an amine using an appropriate electrophile, e.g., an alkyl halide, to form a quarternized alkylated amino salt.

Potency: As used herein, the term "potency," or grammatical equivalents, refers to level of expression of protein(s) or peptide(s) that the mRNA encodes and/or the resulting biological effect.

Salt: As used herein the term "salt" refers to an ionic compound that does or may result from a neutralization reaction between an acid and a base.

Systemic distribution or delivery: As used herein, the terms "systemic distribution," "systemic delivery," or grammatical equivalent, refer to a delivery or distribution mechanism or approach that affect the entire body or an entire organism. Typically, systemic distribution or delivery is accomplished via body's circulation system, e.g., blood stream. Compared to the definition of "local distribution or delivery."

Subject: As used herein, the term "subject" refers to a human or any non-human animal (e.g., mouse, rat, rabbit, dog, cat, cattle, swine, sheep, horse or primate). A human includes pre- and post-natal forms. In many embodiments, a subject is a human being. A subject can be a patient, which refers to a human presenting to a medical provider for diagnosis or treatment of a disease. The term "subject" is used herein interchangeably with "individual" or "patient." A subject can be afflicted with or is susceptible to a disease or disorder but may or may not display symptoms of the disease or disorder.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

Target tissues: As used herein, the term "target tissues" refers to any tissue that is affected by a disease to be treated. In some embodiments, target tissues include those tissues that display disease-associated pathology, symptom, or feature.

Therapeutically effective amount: As used herein, the term "therapeutically effective amount" of a therapeutic agent means an amount that is sufficient, when administered to a subject suffering from or susceptible to a disease, disorder, and/or condition, to treat, diagnose, prevent, and/or delay the onset of the symptom(s) of the disease, disorder, and/or condition. It will be appreciated by those of ordinary skill in the art that a therapeutically effective amount is typically administered via a dosing regimen comprising at least one unit dose.

Therapeutic Index: As used herein, "Therapeutic Index" is the ratio of the concentration of a drug in the blood at which it becomes toxic, and the concentration at which it is effective. The larger the therapeutic index, the safer the drug is.

Treating: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Yield: As used herein, the term "yield" refers to the percentage of mRNA recovered after encapsulation as compared to the total mRNA as starting material. In some embodiments, the term "recovery" is used interchangeably with the term "yield".

DETAILED DESCRIPTION

The present invention provides an improved process for manufacturing mRNA encapsulated in lipid nanoparticle (LNP) formulations for producing mRNA therapeutic composition, such that the composition induces significantly higher expression of the mRNA encoded protein in vivo without causing elevation in liver enzyme biomarkers of stress. In some embodiments, the invention provides compositions comprising LNP and mRNA, which when administered to a subject, induce significantly higher levels of mRNA expression in vivo, without altering the subject's tolerance or stress level. The tolerance or stress is determined by elevation of liver enzymes aspartate transaminase (AST) and/or alanine aminotransferase (ALT). In some embodiments, the specific formulations provide manufacturing advantages, such as ease of manufacturing process, e.g., utilization of common preformed LNP stock solutions, among others.

Formation of Liposomes Encapsulating mRNA—Process C

The instant application is based at least in part on the surprising discovery that when mRNA-LNPs formed by mixing mRNA with preformed empty LNPs in a step (a) were further combined with preformed LNPs in a step (b) to form a mRNA-LNP composition, the potency of the resultant composition is greatly increased compared to the mRNA-LNP of step (a). This is particularly surprising since the increased potency is observed even when the preformed LNPs are empty (i.e., do not comprise an mRNA) and comprise the same lipid components as the mRNA-LNP. Similarly, higher potency of the resultant composition is observed when the pre-formed LNP encapsulate an mRNA encoding a distinct and unrelated protein. Moreover, even in the case where the preformed LNP comprise only neutral lipids, which are known to be poor facilitators of polynucleotide transfection, an increased expression of the mRNA encoded protein is observed.

The instant application is based on yet another surprising discovery that the resultant composition from step (b) does not cause greater alteration in the tolerance or stress level in the subject than the mRNA-LNP of step (a). An alteration of tolerance, or increased stress level in a subject can be demonstrated by measuring the alteration in expression of liver enzymes Aspartate aminotransferase (AST) and Alanine aminotransferase (ALT). Typically, elevated levels of AST and/or ALT are indicative of tissue injury and liver damage, and are routinely measured to determine drug-related tolerability. Based on the method of the invention described above, the resulting mRNA-LNP composition comprises higher proportions of liposomes (or lipids) than the mRNA-LNPs processed in step (a). Although prior art reports have shown lower liver tolerability with liposomes, mRNA-LNP compositions generated by the method of the invention actually show higher liver tolerability. mRNA-LNP composition generated by the method of the invention do not cause increased alteration of AST or ALT in mice. Therefore the observed results are unexpected in view of the existing knowledge.

Therefore, the fact that increased potency of the mRNA-LNP composition is achievable without compromising the in vivo tolerability is a striking advantage of the method of the invention in terms of therapeutic design.

This aspect of the invention allows for at least two significant advantages, (i) providing for lower amount of mRNA in an mRNA therapeutic composition per dose, or lowering the dosing frequency in order to achieve the same biological effect, thereby increasing the therapeutic index of the composition; (ii) developing an easy, flexible, scalable and/or high throughput manufacturing process where one or more preformed LNPs can be prepared in bulk and made available for multiple mixing and combining steps for achieving the desired formulations as described in the invention.

The present invention provides for a process, where mRNA-LNPs prepared by mixing mRNA with preformed empty LNPs are further combined with preformed LNPs, wherein the resultant mRNA-LNP composition of the invention results in increased in vivo expression of the mRNA encoded protein. In some aspects, this process is a manufacturing process comprising the steps of (a) mixing preformed empty LNPs with mRNA under conditions that allow formation of mRNA-LNPs; (b) combining the mRNA-LNPs formed in step (a) with preformed LNPs, thereby manufacturing a composition comprising lipid nanoparticles encapsulating mRNA. In some embodiments, the lipid nanoparticles comprise at least a cationic lipid, a non-cationic lipid and a PEG-modified lipid. In some embodiments, a lipid nanoparticle may comprise a neutral lipid, with or without a cationic lipid.

In some embodiments, the mRNA encodes for a protein or a peptide.

In some embodiments, the preformed LNP in step (b) is an empty LNP. In some embodiments, the preformed LNP in step (b) comprise mRNA. In some embodiments, the preformed LNP in step (b) comprise mRNA that encodes for a protein or a peptide. In some embodiments, the preformed LNP in step (b) comprises the same mRNA encoding the same protein or polypeptide as in the mRNA-LNP formed in step (a). In some embodiments, the preformed LNP in step (b) comprises a different mRNA that encodes a different protein or polypeptide than in the mRNA-LNPs formed in step (a).

In some embodiments, the empty LNP in step (a) and the preformed LNP in step (b) are distinct, heterogeneous lipid nanoparticles. For example, the empty LNP in step (a) may comprise a cationic lipid HGT-5003 (also known as CCBene), and the preformed LNP in step (b) comprise a cationic lipid ICE. In another example, the empty LNP in step (a) may comprise a cationic lipid ICE, and the preformed LNP in step (b) comprise a cationic lipid DOTAP. In yet another example, the empty LNP in step (a) may comprise a cationic lipid HGT-4001, and the preformed LNP in step (b) comprise a cationic lipid ckk-E12 (also known as ML2). The various lipids suitable for LNPs and methods for generating the same are described in the respective section below, and any combination of the lipids to form the LNPs are contemplated herein.

In one embodiment, the mRNA-LNP composition generated in step (b) may comprise a first lipid nanoparticle and a second lipid nanoparticle; wherein the first lipid nanoparticle and the second lipid nanoparticle have identical lipid compositions, where at least some first lipid nanoparticles comprise an mRNA. In one embodiment, the mRNA-LNP composition generated in step (b) may comprise a first lipid nanoparticle and a second lipid nanoparticle; wherein the first lipid nanoparticle and the second lipid nanoparticle have distinct lipid compositions. For example, the mRNA-LNP composition may comprise a first lipid nanoparticle comprising the cationic lipid ICE and a second lipid nanoparticle that comprises the cationic lipid DOTAP. In some embodiments, the mRNA-LNP composition generated in step (b) may comprise a first lipid nanoparticle that comprises the cationic lipid C12-200 and a second lipid nanoparticle that comprises the cationic lipid DLinKC2DMA. Accordingly, any combination of the various lipids suitable for generating LNPs as described in the respective sections below are contemplated herein.

In some embodiments, either the empty LNP of step (a) or the preformed LNP of step (b) does not comprise a cationic lipid. In some embodiments, either the empty LNP or the preformed LNP comprises a neutral lipid and/or a PEG-modified lipid.

Process of Encapsulation

As used herein, a process for formation of mRNA-loaded lipid nanoparticles (mRNA-LNPs) is used interchangeably with the term "mRNA encapsulation" or grammatical variants thereof. In some embodiments, mRNA-LNPs are formed by mixing an mRNA solution with a lipid solution, wherein the mRNA solution and/or the lipid solution are heated to a pre-determined temperature greater than ambient temperature prior to mixing (see published U.S. Application No. US 2011/0244026, the disclosure of which is hereby incorporated in their entirety).

Typically, any desired lipids may be mixed at any ratios suitable for formation of the mRNA-LNPs. In some embodiments, a suitable lipid solution contains a mixture of desired lipids including cationic lipids, helper lipids (e.g. non cationic lipids and/or cholesterol lipids) and/or PEGylated lipids. In some embodiments, a suitable lipid solution contains a mixture of desired lipids including one or more cationic lipids, one or more helper lipids (e.g. non cationic lipids and/or cholesterol lipids) and one or more PEGylated lipids. In some embodiments, a suitable lipid solution contains a mixture of desired lipids including one or more neutral lipids, one or more helper lipids and one or more PEGylated lipids.

In some embodiments, an mRNA solution and a preformed lipid nanoparticle solution are mixed into a solution such that the mRNA becomes encapsulated in the lipid nanoparticle. Such a solution is also referred to as a formulation or encapsulation solution. A process for encapsulating mRNA by mixing preformed lipid nanoparticles with mRNA has been previously described in a published U.S. Application No. US 2018/0153822, which is incorporated in its entirety.

A suitable formulation or encapsulation solution includes a solvent such as ethanol. For example, a suitable formulation or encapsulation solution includes about 10% ethanol, about 15% ethanol, about 20% ethanol, about 25% ethanol, about 30% ethanol, about 35% ethanol, or about 40% ethanol. In some embodiments, a suitable formulation or encapsulation solution includes a solvent such as isopropyl alcohol. For example, a suitable formulation or encapsulation solution includes about 10% isopropyl alcohol, about 15% isopropyl alcohol, about 20% isopropyl alcohol, about 25% isopropyl alcohol, about 30% isopropyl alcohol, about 35% isopropyl alcohol, or about 40% isopropyl alcohol.

In some embodiments, a suitable formulation or encapsulation solution includes a solvent such as dimethyl sulfoxide. For example, a suitable formulation or encapsulation solution includes about 10% dimethyl sulfoxide, about 15% dimethyl sulfoxide, about 20% dimethyl sulfoxide, about 25% dimethyl sulfoxide, about 30% dimethyl sulfoxide, about 35% dimethyl sulfoxide, or about 40% dimethyl sulfoxide.

In some embodiments, a suitable formulation or encapsulation solution may also contain a buffering agent or salt. Exemplary buffering agent may include HEPES, ammonium sulfate, sodium bicarbonate, sodium citrate, sodium acetate, potassium phosphate and sodium phosphate. Exemplary salt may include sodium chloride, magnesium chloride, and potassium chloride. In some embodiments, an empty preformed lipid nanoparticle formulation used in making this novel nanoparticle formulation can be stably frozen in 10% trehalose solution.

In some embodiments, ethanol, citrate buffer, and other destabilizing agents are absent during the addition of mRNA and hence the formulation does not require any further downstream processing. In some embodiments, the lipid nanoparticle formulation prepared by this novel process consists of preformed lipid nanoparticles in trehalose solution. The lack of destabilizing agents and the stability of trehalose solution increase the ease of scaling up the formulation and production of mRNA-encapsulated lipid nanoparticles.

In some embodiments, the empty preformed lipid nanoparticles are formed by mixing lipids dissolved in ethanol with an aqueous solution (Lipid Solution). In some embodiments, the lipids contain one or more cationic lipids, one or more non-cationic lipids, and one or more PEG lipids. In some embodiments, the lipids also contain one or more cholesterol lipids. In some embodiments, the lipids are present in ethanolic stock solution. The preformed lipid nanoparticles are formed by the mixing of those lipids. Typically, in some embodiments, a lipid solution containing dissolved lipids, and an aqueous or buffer solution are mixed into a solution such that the lipids can form nanoparticles without mRNA (i.e., empty preformed lipid nanoparticles).

Lipid Solution

According to the present invention, a lipid solution contains a mixture of lipids suitable to form lipid nanoparticles for encapsulation of mRNA. In some embodiments, a suitable lipid solution is ethanol based. For example, a suitable lipid solution may contain a mixture of desired lipids dissolved in pure ethanol (i.e., 100% ethanol). In another embodiment, a suitable lipid solution is isopropyl alcohol based. In another embodiment, a suitable lipid solution is dimethylsulfoxide-based. In another embodiment, a suitable lipid solution is a mixture of suitable solvents including, but not limited to, ethanol, isopropyl alcohol and dimethylsulfoxide.

A suitable lipid solution may contain a mixture of desired lipids at various concentrations. For example, a suitable lipid solution may contain a mixture of desired lipids at a total concentration of about 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.1 mg/ml, 0.5 mg/ml, 1.0 mg/ml, 2.0 mg/ml, 3.0 mg/ml, 4.0 mg/ml, 5.0 mg/ml, 6.0 mg/ml, 7.0 mg/ml, 8.0 mg/ml, 9.0 mg/ml, 10 mg/ml, 15 mg/ml, 20 mg/ml, 30 mg/ml, 40 mg/ml, 50 mg/ml, or 100 mg/ml. In some embodiments, a suitable lipid solution may contain a mixture of desired lipids at a total concentration ranging from about 0.1-100 mg/ml, 0.5-90 mg/ml, 1.0-80 mg/ml, 1.0-70 mg/ml, 1.0-60 mg/ml, 1.0-50 mg/ml, 1.0-40 mg/ml, 1.0-30 mg/ml, 1.0-20 mg/ml, 1.0-15 mg/ml, 1.0-10 mg/ml, 1.0-9 mg/ml, 1.0-8 mg/ml, 1.0-7 mg/ml, 1.0-6 mg/ml, or 1.0-5 mg/ml. In some embodiments, a suitable lipid solution may contain a mixture of desired lipids at a total concentration up to about 100 mg/ml, 90 mg/ml, 80 mg/ml, 70 mg/ml, 60 mg/ml, 50 mg/ml, 40 mg/ml, 30 mg/ml, 20 mg/ml, or 10 mg/ml.

Any desired lipids may be mixed at any ratios suitable for encapsulating mRNAs. In some embodiments, a suitable lipid solution contains a mixture of desired lipids including cationic lipids, helper lipids (e.g. non cationic lipids and/or cholesterol lipids) and/or PEGylated lipids. In some embodiments, a suitable lipid solution contains a mixture of desired lipids including one or more cationic lipids, one or more helper lipids (e.g. non cationic lipids and/or cholesterol lipids) and one or more PEGylated lipids. In some embodiments, a suitable lipid solution contains a mixture of desired lipids including one or more neutral lipids, one or more helper lipids and one or more PEGylated lipids.

In some embodiments, an empty (i.e., absence of mRNA) preformed lipid nanoparticle formulation used in making nanoparticle formulation of the invention can be stably frozen in about 5%, about 10%, about 15%, about 20%, about 25%, about 30%, about 35%, about 40%, about 45%, or about 50% trehalose solution. In some embodiments, addition of mRNA to empty lipid nanoparticles can result in a final formulation that does not require any downstream purification or processing and can be stably stored in frozen form.

mRNA Solution mRNA may be provided in a solution to be mixed with a lipid solution such that the mRNA may be encapsulated in lipid nanoparticles. A suitable mRNA solution may be any aqueous solution containing mRNA to be encapsulated at various concentrations below 1 mg/ml. For example, a suitable mRNA solution may contain an mRNA at a concentration of or less than about 0.01 mg/ml, 0.02 mg/ml, 0.03 mg/ml, 0.04 mg/ml, 0.05 mg/ml, 0.06 mg/ml, 0.07 mg/ml, 0.08 mg/ml, 0.09 mg/ml, 0.1 mg/ml, 0.15 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, or 1.0 mg/ml.

Typically, a suitable mRNA solution may also contain a buffering agent and/or salt. Generally, buffering agents can include HEPES, ammonium sulfate, sodium bicarbonate, sodium citrate, sodium acetate, potassium phosphate and sodium phosphate. In some embodiments, suitable concentration of the buffering agent may range from about 0.1 mM to 100 mM, 0.5 mM to 90 mM, 1.0 mM to 80 mM, 2 mM to 70 mM, 3 mM to 60 mM, 4 mM to 50 mM, 5 mM to 40 mM, 6 mM to 30 mM, 7 mM to 20 mM, 8 mM to 15 mM, or 9 to 12 mM. In some embodiments, suitable concentration of the buffering agent is or greater than about 0.1 mM, 0.5 mM, 1 mM, 2 mM, 4 mM, 6 mM, 8 mM, 10 mM, 15 mM, 20 mM, 25 mM, 30 mM, 35 mM, 40 mM, 45 mM, or 50 mM.

Exemplary salts can include sodium chloride, magnesium chloride, and potassium chloride. In some embodiments, suitable concentration of salts in an mRNA solution may range from about 1 mM to 500 mM, 5 mM to 400 mM, 10 mM to 350 mM, 15 mM to 300 mM, 20 mM to 250 mM, 30 mM to 200 mM, 40 mM to 190 mM, 50 mM to 180 mM, 50 mM to 170 mM, 50 mM to 160 mM, 50 mM to 150 mM, or 50 mM to 100 mM. Salt concentration in a suitable mRNA solution is or greater than about 1 mM, 5 mM, 10 mM, 20 mM, 30 mM, 40 mM, 50 mM, 60 mM, 70 mM, 80 mM, 90 mM, or 100 mM.

In some embodiments, a suitable mRNA solution may have a pH ranging from about 3.5-6.5, 3.5-6.0, 3.5-5.5., 3.5-5.0, 3.5-4.5, 4.0-5.5, 4.0-5.0, 4.0-4.9, 4.0-4.8, 4.0-4.7, 4.0-4.6, or 4.0-4.5. In some embodiments, a suitable mRNA solution may have a pH of or no greater than about 3.5, 4.0, 4.1, 4.2, 4.3, 4.4, 4.5, 4.6, 4.7, 4.8, 4.9, 5.0, 5.2, 5.4, 5.6, 5.8, 6.0, 6.1, 6.3, and 6.5.

Various methods may be used to prepare an mRNA solution suitable for the present invention. In some embodiments, mRNA may be directly dissolved in a buffer solution described herein. In some embodiments, an mRNA solution may be generated by mixing an mRNA stock solution with a buffer solution prior to mixing with a lipid solution for encapsulation. In some embodiments, an mRNA solution may be generated by mixing an mRNA stock solution with a buffer solution immediately before mixing with a lipid solution for encapsulation. In some embodiments, a suitable mRNA stock solution may contain mRNA in water at a concentration at or greater than about 0.2 mg/ml, 0.4 mg/ml, 0.5 mg/ml, 0.6 mg/ml, 0.8 mg/ml, 1.0 mg/ml, 1.2 mg/ml, 1.4 mg/ml, 1.5 mg/ml, or 1.6 mg/ml, 2.0 mg/ml, 2.5 mg/ml, 3.0 mg/ml, 3.5 mg/ml, 4.0 mg/ml, 4.5 mg/ml, or 5.0 mg/ml.

In some embodiments, an mRNA stock solution is mixed with a buffer solution using a pump. Exemplary pumps include but are not limited to gear pumps, peristaltic pumps and centrifugal pumps.

Typically, the buffer solution is mixed at a rate greater than that of the mRNA stock solution. For example, the buffer solution may be mixed at a rate at least 1×, 2×, 3×, 4×, 5×, 6×, 7×, 8×, 9×, 10×, 15×, or 20× greater than the rate of the mRNA stock solution. In some embodiments, a process according to the present invention includes a step of first generating an mRNA solution by mixing a citrate buffer with an mRNA stock solution. In certain embodiments, a suitable citrate buffer contains about 10 mM citrate, about 150 mM NaCl, pH of about 4.5. In some embodiments, a suitable mRNA stock solution contains the mRNA at a concentration at or greater than about 1 mg/ml, about 10 mg/ml, about 50 mg/ml, or about 100 mg/ml.

In some embodiments, the citrate buffer is mixed at a flow rate ranging between about 100-300 ml/minute, 300-600 ml/minute, 600-1200 ml/minute, 1200-2400 ml/minute, 2400-3600 ml/minute, 3600-4800 ml/minute, or 4800-6000 ml/minute. In some embodiments, the citrate buffer is mixed at a flow rate of about 220 ml/minute, about 600 ml/minute, about 1200 ml/minute, about 2400 ml/minute, about 3600 ml/minute, about 4800 ml/minute, or about 6000 ml/minute.

In some embodiments, the mRNA stock solution is mixed at a flow rate ranging between about 10-30 ml/minute, about 30-60 ml/minute, about 60-120 ml/minute, about 120-240 ml/minute, about 240-360 ml/minute, about 360-480 ml/minute, or about 480-600 ml/minute. In some embodiments, the mRNA stock solution is mixed at a flow rate of about 20 ml/minute, about 40 ml/minute, about 60 ml/minute, about 80 ml/minute, about 100 ml/minute, about 200 ml/minute, about 300 ml/minute, about 400 ml/minute, about 500 ml/minute, or about 600 ml/minute.

In some embodiments, a buffer solution is mixed at a flow rate ranging between about 100-6000 ml/minute (e.g., about 100-300 ml/minute, 300-600 ml/minute, 600-1200 ml/minute, 1200-2400 ml/minute, 2400-3600 ml/minute, 3600-4800 ml/minute, 4800-6000 ml/minute, or 60-420 ml/minute). In some embodiments, a buffer solution is mixed at a flow rate of or greater than about 60 ml/minute, 100 ml/minute, 140 ml/minute, 180 ml/minute, 220 ml/minute, 260 ml/minute, 300 ml/minute, 340 ml/minute, 380 ml/minute, 420 ml/minute, 480 ml/minute, 540 ml/minute, 600 ml/minute, 1200 ml/minute, 2400 ml/minute, 3600 ml/minute, 4800 ml/minute, or 6000 ml/minute.

In some embodiments, an mRNA stock solution is mixed at a flow rate ranging between about 10-600 ml/minute (e.g., about 5-50 ml/minute, about 10-30 ml/minute, about 30-60 ml/minute, about 60-120 ml/minute, about 120-240 ml/minute, about 240-360 ml/minute, about 360-480 ml/minute, or about 480-600 ml/minute). In some embodiments, an mRNA stock solution is mixed at a flow rate of or greater than about 5 ml/minute, 10 ml/minute, 15 ml/minute, 20 ml/minute, 25 ml/minute, 30 ml/minute, 35 ml/minute, 40 ml/minute, 45 ml/minute, 50 ml/minute, 60 ml/minute, 80 ml/minute, 100 ml/minute, 200 ml/minute, 300 ml/minute, 400 ml/minute, 500 ml/minute, or 600 ml/minute.

In some embodiments, the preformed lipid nanoparticles and mRNA are mixed using a pump system. In some embodiments, the pump system comprises a pulse-less flow pump. In some embodiments, the pump system is a gear pump. In some embodiments, a suitable pump is a peristaltic pump. In some embodiments, a suitable pump is a centrifugal pump. In some embodiments, the process using a pump system is performed at large scale. For example, in some embodiments, the process includes using pumps as described herein to mix a solution of at least about 1 mg, 5 mg, 10 mg, 50 mg, 100 mg, 500 mg, or 1000 mg of mRNA with a solution of pre-formed lipid nanoparticles, to produce mRNA encapsulated in lipid nanoparticles. In some embodiments, the process of mixing mRNA with preformed lipid nanoparticles provides a composition according to the present invention that contains at least about 1 mg, 5 mg, 10 mg, 50 mg, 100 mg, 500 mg, or 1000 mg of encapsulated mRNA.

In some embodiments, the solution comprising preformed lipid nanoparticles is mixed at a flow rate ranging from about 25-75 ml/minute, about 75-200 ml/minute, about 200-350 ml/minute, about 350-500 ml/minute, about 500-650 ml/minute, about 650-850 ml/minute, or about 850-1000 ml/minute. In some embodiments, the solution comprising preformed lipid nanoparticles is mixed at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, the mRNA is mixed in a solution at a flow rate ranging from about 25-75 ml/minute, about 75-200 ml/minute, about 200-350 ml/minute, about 350-500 ml/minute, about 500-650 ml/minute, about 650-850 ml/minute, or about 850-1000 ml/minute. In some embodiments, the mRNA is mixed in a solution at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, a step of combining lipid nanoparticles encapsulating mRNA with preformed lipid particles is performed using a pump system. Such combining may be performed using a pump. In some embodiments, the mRNA-encapsulated lipid nanoparticles are mixed with preformed lipid nanoparticles are mixed at a flow rate ranging from about 25-75 ml/minute, about 75-200 ml/minute, about 200-350 ml/minute, about 350-500 ml/minute, about 500-650 ml/minute, about 650-850 ml/minute, or about 850-1000 ml/minute. In some embodiments, the mRNA is mixed in a solution at a flow rate of about 50 ml/minute, about 100 ml/minute, about 150 ml/minute, about 200 ml/minute, about 250 ml/minute, about 300 ml/minute, about 350 ml/minute, about 400 ml/minute, about 450 ml/minute, about 500 ml/minute, about 550 ml/minute, about 600 ml/minute, about 650 ml/minute, about 700 ml/minute, about 750 ml/minute, about 800 ml/minute, about 850 ml/minute, about 900 ml/minute, about 950 ml/minute, or about 1000 ml/minute.

In some embodiments, the mixing of lipid nanoparticles and mRNA is performed in absence of any pump.

In some embodiments, the process according to the present invention includes a step of heating one or more of the solutions (i.e., applying heat from a heat source to the solution) to a temperature (or to maintain at a temperature) greater than ambient temperature, the one more solutions being the solution comprising the preformed lipid nanoparticles, the solution comprising the mRNA and the mixed solution comprising the lipid nanoparticle encapsulated mRNA. In some embodiments, the process includes the step of heating one or both of the mRNA solution and the preformed lipid nanoparticle solution, prior to the mixing step. In some embodiments, the process includes heating one or more one or more of the solution comprising the preformed lipid nanoparticles, the solution comprising the mRNA and the solution comprising the lipid nanoparticle encapsulated mRNA, during the mixing step. In some embodiments, the process includes the step of heating the lipid nanoparticle encapsulated mRNA, after the mixing step. In some embodiments, the temperature to which one or more of the solutions is heated (or at which one or more of the solutions is maintained) is or is greater than about 30° C., 37° C., 40° C., 45° C., 50° C., 55° C., 60° C., 65° C., or 70° C. In some embodiments, the temperature to which one or more of the solutions is heated ranges from about 25-70° C., about 30-70° C., about 35-70° C., about 40-70° C., about 45-70° C., about 50-70° C., or about 60-70° C. In some embodiments, the temperature greater than ambient temperature to which one or more of the solutions is heated is about 65° C.

In some embodiments, the process according to the present invention includes maintaining at ambient temperature (i.e., not applying heat from a heat source to the solution) one or more of the solution comprising the preformed lipid nanoparticles, the solution comprising the mRNA and the mixed solution comprising the lipid nanoparticle encapsulated mRNA. In some embodiments, the process includes the step of maintaining at ambient temperature one or both of the mRNA solution and the preformed lipid nanoparticle solution, prior to the mixing step. In some embodiments, the process includes maintaining at ambient temperature one or more one or more of the solution comprising the preformed lipid nanoparticles, the solution comprising the mRNA and the solution comprising the lipid nanoparticle encapsulated mRNA, during the mixing step. In some embodiments, the process includes the step of maintaining the lipid nanoparticle encapsulated mRNA at ambient temperature after the mixing step. In some embodiments, the ambient temperature at which one or more of the solutions is maintained is or is less than about 35° C., 30° C., 25° C., 20° C., or 16° C. In some embodiments, the ambient temperature at which one or more of the solutions is maintained ranges from about 15-35° C., about 15-30° C., about 15-25° C., about 15-20° C., about 20-35° C., about 25-35° C., about 30-35° C., about 20-30° C., about 25-30° C. or about 20-25° C. In some embodiments, the ambient temperature at which one or more of the solutions is maintained is 20-25° C.

In some embodiments, the process according to the present invention includes performing at ambient temperature the step of mixing the solution comprising preformed lipid nanoparticles and the solution comprising mRNA to form lipid nanoparticles encapsulating mRNA.

In some embodiments, greater than about 50%, 55%, 60%, 65%, 70%, 75%, 80%, 85%, 90%, 95%, 96%, 97%, 98%, or 99% of the purified nanoparticles have a size less than about 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, substantially all of the purified nanoparticles have a size less than 150 nm (e.g., less than about 145 nm, about 140 nm, about 135 nm, about 130 nm, about 125 nm, about 120 nm, about 115 nm, about 110 nm, about 105 nm, about 100 nm, about 95 nm, about 90 nm, about 85 nm, about 80 nm, about 75 nm, about 70 nm, about 65 nm, about 60 nm, about 55 nm, or about 50 nm). In some embodiments, greater than about 70%, 75%, 80%, 85%, 90%, 95%, 96%, 97%, 98%, 99% of the purified nanoparticles have a size ranging from 50-150 nm. In some embodiments, substantially all of the purified nanoparticles have a size ranging from 50-150 nm. In some embodiments, greater than about 70%, 75%, 80%, 85%, 90%, 95%, 96%, 97%, 98%, 99% of the purified nanoparticles have a size ranging from 80-150 nm. In some embodiments, substantially all of the purified nanoparticles have a size ranging from 80-150 nm.

In some embodiments, a process according to the present invention results in an encapsulation rate of greater than about 90%, 95%, 96%, 97%, 98%, or 99%. In some embodiments, a process according to the present invention results in greater than about 60%, 65%, 70%, 75%, 80%, 85%, 90%, 95%, 96%, 97%, 98%, or 99% recovery of mRNA.

In some embodiments, lipid nanoparticles encapsulating mRNA are combined with preformed lipid particles in step (b) of the process at a ratio of 20:1, 10:1, 9:1, 8:1, 7:1, 6:1, 5:1, 4:1, 3:1, 2:1, 1:1, 1:2, 1:3, 1:4, 1:5, 1:6, 1:7, 1:8, 1:9, 1:10, or 1:20. The process of combining the lipid nanoparticles are as described above for mixing lipid nanoparticles with mRNA. In some embodiments, lipid nanoparticles encapsulating mRNA are combined with preformed lipid particles in step (b) of the process at a ratio of 20:1. In some embodiments, lipid nanoparticles encapsulating mRNA are combined with preformed lipid particles in step (b) of the process at a ratio of 19:1. In some embodiments, lipid nanoparticles encapsulating mRNA are combined with preformed lipid particles in step (b) of the process at a ratio of 15:1. In some embodiments, lipid nanoparticles encapsulating mRNA are combined with preformed lipid particles in step (b) of the process at a ratio of 10:1. In some embodiments, lipid nanoparticles encapsulating mRNA are combined with preformed lipid particles in step (b) of the process at a ratio of 9:1. In some embodiments, lipid nanoparticles encapsulating mRNA are combined with preformed lipid particles in step (b) of the process at a ratio of 8:1. In some embodiments, lipid nanoparticles encapsulating mRNA are combined with preformed lipid particles in step (b) of the process at a ratio of 7:1. In some embodiments, lipid nanoparticles encapsulating mRNA are combined with preformed lipid particles in step (b) of the process at a ratio of 6:1. In some embodiments, lipid nanoparticles encapsulating mRNA are combined with preformed lipid particles in step (b) of the process at a ratio of 5:1. In some embodiments, lipid nanoparticles encapsulating mRNA are combined with preformed lipid particles in step (b) of the process at a ratio of 4:1. In some embodiments, lipid nanoparticles encapsulating mRNA are combined with preformed lipid particles in step (b) of the process at a ratio of 3:1. In some embodiments, lipid nanoparticles encapsulating mRNA are combined with preformed lipid particles in step (b) of the process at a ratio of 2:1. In some embodiments, lipid nanoparticles encapsulating mRNA are combined with preformed lipid particles in step (b) of the process at a ratio of 1:1. In some embodiments, lipid nanoparticles encapsulating mRNA are combined with preformed lipid particles in step (b) of the process at a ratio of 1:2. In some embodiments, lipid nanoparticles encapsulating mRNA are combined with preformed lipid particles in step (b) of the process at a ratio of 1:3. In some embodiments, lipid nanoparticles encapsulating mRNA are combined with preformed lipid particles in step (b) of the process at a ratio of 1:4. In some embodiments, lipid nanoparticles encapsulating mRNA are combined with preformed lipid particles in step (b) of the process at a ratio of 1:5. In some embodiments, lipid nanoparticles encapsulating mRNA are combined with preformed lipid particles in step (b) of the process at a ratio of 1:6. In some embodiments, lipid nanoparticles encapsulating mRNA are combined with preformed lipid particles in step (b) of the process at a ratio of 1:7. In some embodiments, lipid nanoparticles encapsulating mRNA are combined with preformed lipid particles in step (b) of the process at a ratio of 1:8. In some embodiments, lipid nanoparticles encapsulating mRNA are combined with preformed lipid particles in step (b) of the process at a ratio of 1:9. In some embodiments, lipid nanoparticles encapsulating mRNA are combined with preformed lipid particles in step (b) of the process at a ratio of 1:10. In some embodiments, lipid nanoparticles encapsulating mRNA are combined with preformed lipid particles in step (b) of the process at a ratio of 1:12. In some embodiments, lipid nanoparticles encapsulating mRNA are combined with preformed lipid particles in step (b) of the process at a ratio of 1:15. In some embodiments, lipid nanoparticles encapsulating mRNA are combined with preformed lipid particles in step (b) of the process at a ratio of 1:20.

Purification

In some embodiments, the empty preformed lipid nanoparticles or mRNA-LNPs are purified and/or concentrated. Various purification methods may be used. In some embodiments, the lipid nanoparticles are purified by a Tangential Flow Filtration (TFF) process. In some embodiments, the lipid nanoparticles are purified by gravity-based normal flow filtration (NFF). In some embodiments, the lipid nanoparticles are purified by any other suitable filtration process. In some embodiments, the lipid nanoparticles are purified by centrifugation. In some embodiments, the lipid nanoparticles are purified by chromatographic methods.

Delivery Vehicles

According to the present invention, mRNA encoding a protein or a peptide (e.g., a full length, fragment, or portion of a protein or a peptide) as described herein may be delivered as naked RNA (unpackaged) or via delivery vehicles. As used herein, the terms "delivery vehicle," "transfer vehicle," "nanoparticle" or grammatical equivalent, are used interchangeably.

Delivery vehicles can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition. A particular delivery vehicle is selected based upon its ability to facilitate the transfection of a nucleic acid to a target cell.

In some embodiments, mRNAs encoding at least one protein or peptide may be delivered via a single delivery vehicle. In some embodiments, mRNAs encoding at least one protein or peptide may be delivered via one or more delivery vehicles each of a different composition. In some embodiments, the one or more mRNAs and/or are encapsulated within the same lipid nanoparticles. In some embodiments, the one or more mRNAs are encapsulated within separate lipid nanoparticles. In some embodiments, lipid nanoparticles are empty.

According to various embodiments, suitable delivery vehicles include, but are not limited to polymer based carriers, such as polyethyleneimine (PEI), lipid nanoparticles and liposomes, nanoliposomes, ceramide-containing nanoliposomes, proteoliposomes, both natural and synthetically-derived exosomes, natural, synthetic and semi-synthetic lamellar bodies, nanoparticulates, calcium phosphor-silicate nanoparticulates, calcium phosphate nanoparticulates, silicon dioxide nanoparticulates, nanocrystalline particulates, semiconductor nanoparticulates, poly (D-arginine), sol-gels, nanodendrimers, starch-based delivery systems, micelles, emulsions, niosomes, multi-domain-block polymers (vinyl polymers, polypropyl acrylic acid polymers, dynamic polyconjugates), dry powder formulations, plasmids, viruses, calcium phosphate nucleotides, aptamers, peptides and other vectorial tags. Also contemplated is the use of bionanocapsules and other viral capsid proteins assemblies as a suitable transfer vehicle. (Hum. Gene Ther. 2008 September; 19(9):887-95).

Liposomal Delivery Vehicles

In some embodiments, a suitable delivery vehicle is a liposomal delivery vehicle, e.g., a lipid nanoparticle. As used herein, liposomal delivery vehicles, e.g., lipid nanoparticles, are usually characterized as microscopic vesicles having an interior aqua space sequestered from an outer medium by a membrane of one or more bilayers. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). In the context of the present invention, a liposomal delivery vehicle typically serves to transport a desired nucleic acid (e.g., mRNA) to a target cell or tissue. In some embodiments, a nanoparticle delivery vehicle is a liposome. In some embodiments, a liposome comprises one or more cationic lipids, one or more non-cationic lipids, one or more cholesterol-based lipids, or one or more PEG-modified lipids. In some embodiments, a liposome comprises no more than four distinct lipid components. In some embodiments, a liposome comprises no more than three distinct lipid components. In some embodiments, one distinct lipid component is a sterol-based cationic lipid.

In some embodiments, the lipid nanoparticle is a liposome that comprises four distinct lipid components, namely a cationic lipid, a non-cationic lipid, cholesterol and a PEG-modified lipid. In some embodiments, the molar ratio of cationic lipid to non-cationic lipid to cholesterol to PEG-modified lipid is between about 30-60:25-35:20-30:1-15, respectively.

In some embodiments, the lipid nanoparticle is a liposome that comprises three distinct lipid components, namely a cationic lipid (typically a sterol-based cationic lipid), a non-cationic lipid, and a PEG-modified lipid. In some embodiments, the molar ratio of cationic lipid to non-cationic lipid to PEG-modified lipid is approximately 60:35:5, respectively.

In some embodiments, the non-cationic lipid is DOPE. In some embodiments, the non-cationic lipid is DEPE. In some embodiments, the PEG-modified lipid is DMG-PEG2K.

Cationic Lipids

As used herein, the phrase "cationic lipids" refers to any of a number of lipid species that have a net positive charge at a selected pH, such as physiological pH.

Suitable cationic lipids for use in the compositions and methods of the invention include the cationic lipids as described in International Patent Publication WO 2010/144740, which is incorporated herein by reference. In certain embodiments, the compositions and methods of the present invention include a cationic lipid, (6Z,9Z,28Z,31Z)-heptatriaconta-6,9,28,31-tetraen-19-yl 4-(dimethylamino) butanoate, having a compound structure of:

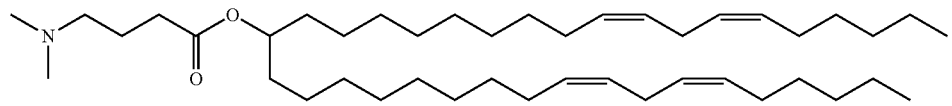 [SMILES: CCCCC/C=C\C/C=C\CCCCCCCCC(CCCCCCCC/C=C\C/C=C\CCCCC)OC(=O)CCCN(C)C]

and pharmaceutically acceptable salts thereof.

Other suitable cationic lipids for use in the compositions and methods of the present invention include ionizable cationic lipids as described in International Patent Publication WO 2013/149140, which is incorporated herein by reference. In some embodiments, the compositions and methods of the present invention include a cationic lipid of one of the following formulas:

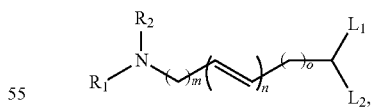

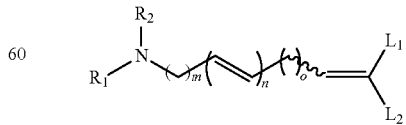

or a pharmaceutically acceptable salt thereof, wherein $R_1$ and $R_2$ are each independently selected from the group consisting of hydrogen, an optionally substituted, variably saturated or unsaturated $C_1$-$C_{20}$ alkyl and an optionally substituted, variably saturated or unsaturated $C_6$-$C_{20}$ acyl; wherein $L_1$ and $L_2$ are each independently selected from the group consisting of hydrogen, an optionally substituted $C_1$-$C_{30}$ alkyl, an optionally substituted variably unsaturated $C_1$-$C_{30}$ alkenyl, and an optionally substituted $C_1$-$C_{30}$ alkynyl; wherein m and o are each independently selected from the group consisting of zero and any positive integer (e.g., where m is three); and wherein n is zero or any positive integer (e.g., where n is one). In certain embodiments, the compositions and methods of the present invention include the cationic lipid (15Z, 18Z)—N,N-dimethyl-6-(9Z,12Z)-octadeca-9,12-dien-1-yl) tetracosa-15,18-dien-1-amine ("HGT5000"), having a compound structure of:

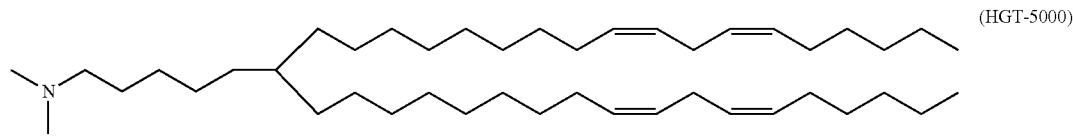 [SMILES: CCCCC/C=C\C/C=C\CCCCCCCCC(CCCCCCCC/C=C\C/C=C\CCCCC)CCCCCN(C)C]

(HGT-5000)

and pharmaceutically acceptable salts thereof. In certain embodiments, the compositions and methods of the present invention include the cationic lipid (15Z, 18Z)—N,N-dimethyl-6-((9Z,12Z)-octadeca-9,12-dien-1-yl) tetracosa-4,15,18-trien-1-amine ("HGT5001"), having a compound structure of:

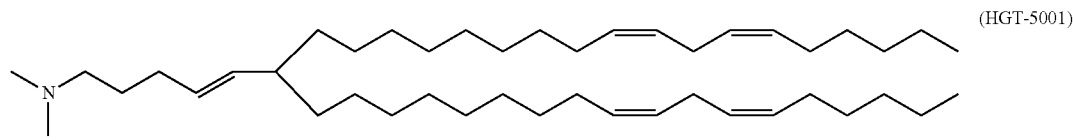

(HGT-5001)

and pharmaceutically acceptable salts thereof. In certain embodiments, the compositions and methods of the present invention include the cationic lipid and (15Z,18Z)—N,N-dimethyl-6-((9Z,12Z)-octadeca-9,12-dien-1-yl) tetracosa-5,15,18-trien-1-amine ("HGT5002"), having a compound structure of:

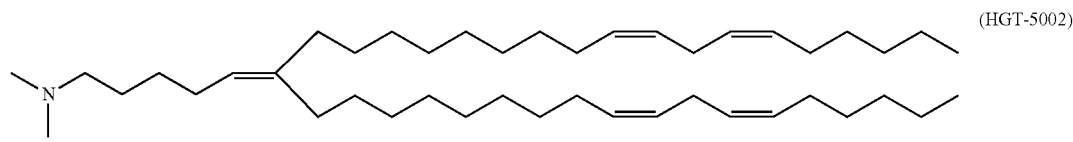

(HGT-5002)

and pharmaceutically acceptable salts thereof.

Other suitable cationic lipids for use in the compositions and methods of the invention include cationic lipids described as aminoalcohol lipidoids in International Patent Publication WO 2010/053572, which is incorporated herein by reference. In certain embodiments, the compositions and methods of the present invention include a cationic lipid having a compound structure of:

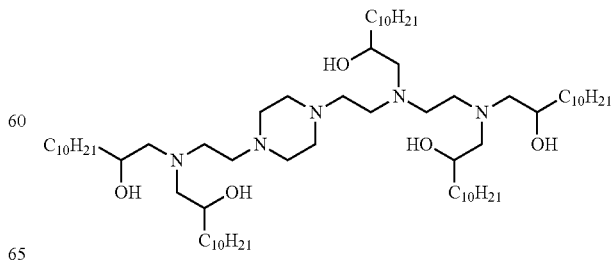

and pharmaceutically acceptable salts thereof.

Other suitable cationic lipids for use in the compositions and methods of the invention include the cationic lipids as described in International Patent Publication WO 2016/118725, which is incorporated herein by reference. In certain embodiments, the compositions and methods of the present invention include a cationic lipid having a compound structure of:

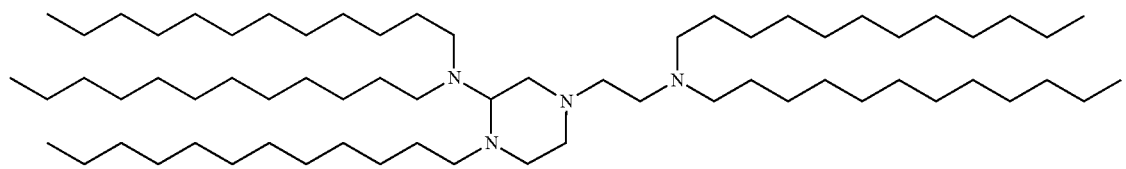 [SMILES: CCCCCCCCCCCCN(CCCCCCCCCCCC)CCN1CCN(CCCCCCCCCCCC)C(N(CCCCCCCCCCCC)CCCCCCCCCCCC)C1]

and pharmaceutically acceptable salts thereof.

Other suitable cationic lipids for use in the compositions and methods of the invention include the cationic lipids as described in International Patent Publication WO 2016/118724, which is incorporated herein by reference. In certain embodiments, the compositions and methods of the present invention include a cationic lipid having a compound structure of:

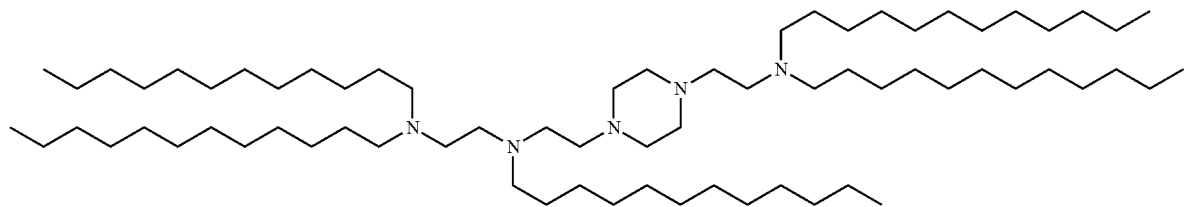 [SMILES: CCCCCCCCCCCCN(CCCCCCCCCCCC)CCN(CCCCCCCCCCCC)CCN1CCN(CCN(CCCCCCCCCCCC)CCCCCCCCCCCC)CC1]

and pharmaceutically acceptable salts thereof.

Other suitable cationic lipids for use in the compositions and methods of the invention include a cationic lipid having the formula of 14,25-ditridecyl 15,18,21,24-tetraaza-octatriacontane, and pharmaceutically acceptable salts thereof.

Other suitable cationic lipids for use in the compositions and methods of the invention include the cationic lipids as described in International Patent Publications WO 2013/063468 and WO 2016/205691, each of which are incorporated herein by reference. In some embodiments, the compositions and methods of the present invention include a cationic lipid of the following formula:

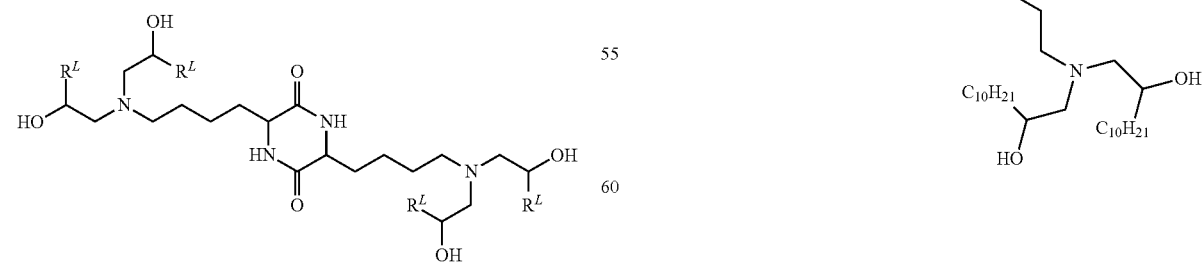

or pharmaceutically acceptable salts thereof, wherein each instance of $R^L$ is independently optionally substituted $C_6$-$C_{40}$ alkenyl. In certain embodiments, the compositions and methods of the present invention include a cationic lipid having a compound structure of:

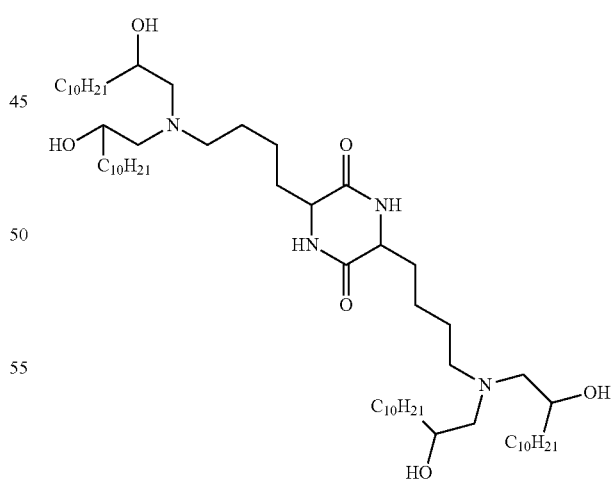

and pharmaceutically acceptable salts thereof. In certain embodiments, the compositions and methods of the present invention include a cationic lipid having a compound structure of:

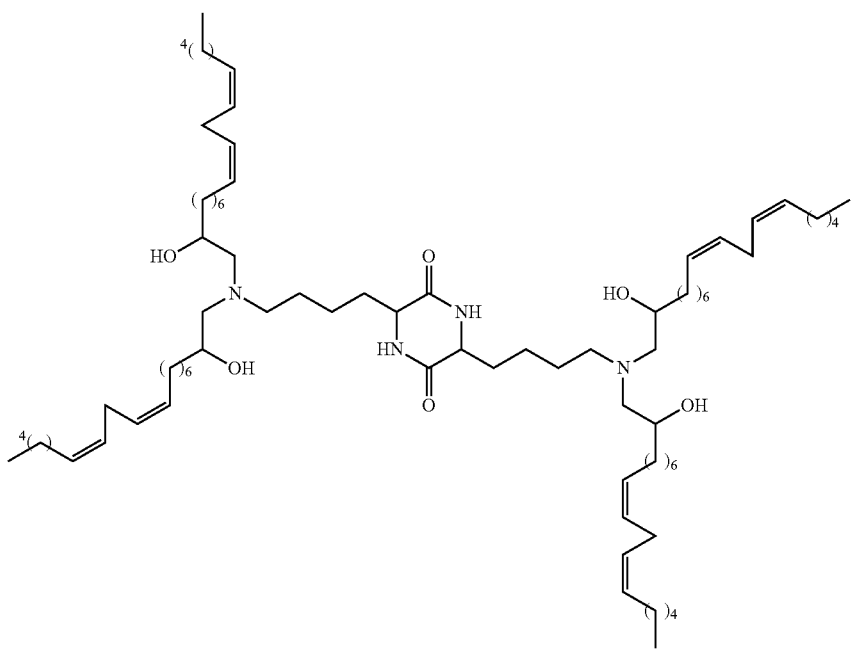

and pharmaceutically acceptable salts thereof. In certain embodiments, the compositions and methods of the present invention include a cationic lipid having a compound structure of:

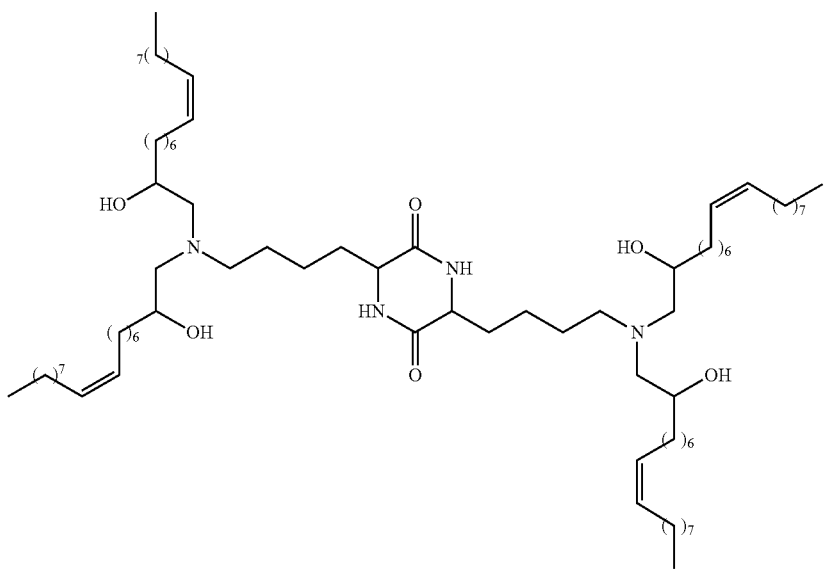

and pharmaceutically acceptable salts thereof. In certain embodiments, the compositions and methods of the present invention include a cationic lipid having a compound structure of:

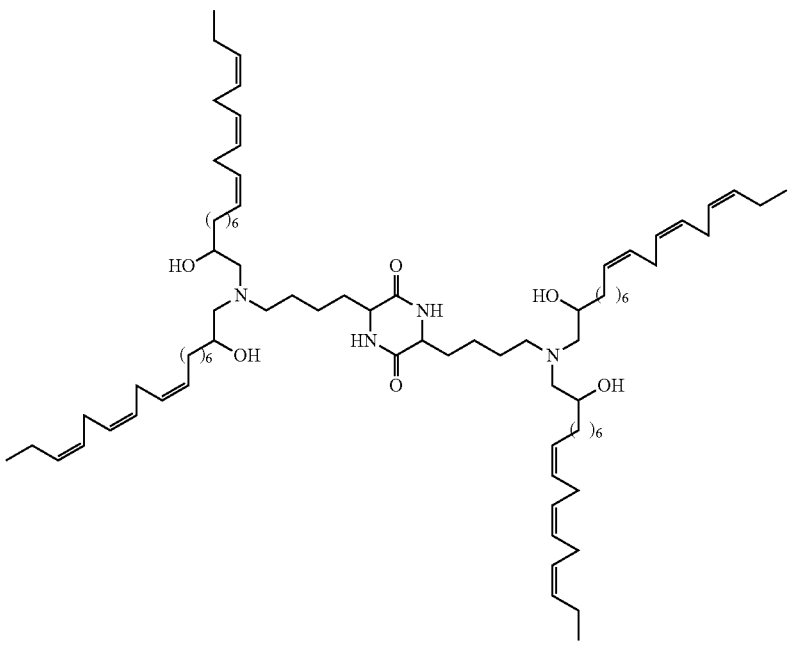

and pharmaceutically acceptable salts thereof.

Other suitable cationic lipids for use in the compositions and methods of the invention include the cationic lipids as described in International Patent Publication WO 2015/184256, which is incorporated herein by reference. In some embodiments, the compositions and methods of the present invention include a cationic lipid of the following formula:

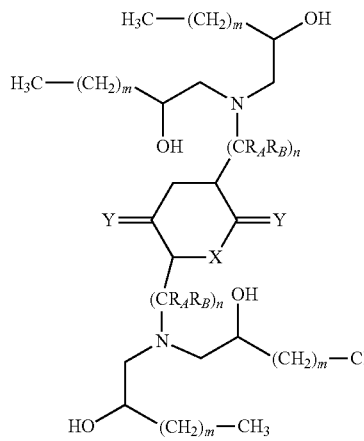

or a pharmaceutically acceptable salt thereof, wherein each X independently is O or S; each Y independently is O or S; each m independently is 0 to 20; each n independently is 1 to 6; each $R_A$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen; and each $R_B$ is independently hydrogen, optionally substituted C1-50 alkyl, optionally substituted C2-50 alkenyl, optionally substituted C2-50 alkynyl, optionally substituted C3-10 carbocyclyl, optionally substituted 3-14 membered heterocyclyl, optionally substituted C6-14 aryl, optionally substituted 5-14 membered heteroaryl or halogen. In certain embodiments, the compositions and methods of the present invention include a cationic lipid, "Target 23", having a compound structure of:

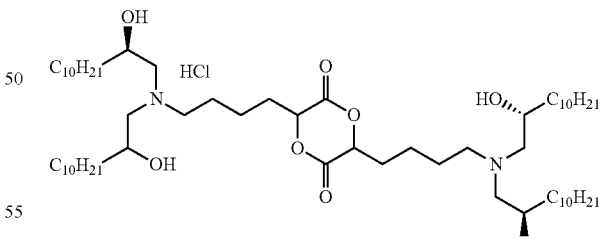

(Target 23)

and pharmaceutically acceptable salts thereof.

Other suitable cationic lipids for use in the compositions and methods of the invention include the cationic lipids as described in International Patent Publication WO 2016/004202, which is incorporated herein by reference. In some embodiments, the compositions and methods of the present invention include a cationic lipid having the compound

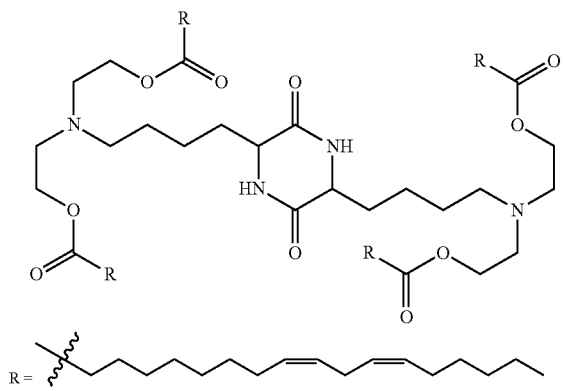

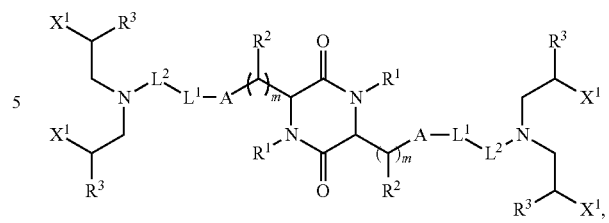

or a pharmaceutically acceptable salt thereof. In some embodiments, the compositions and methods of the present invention include a cationic lipid having the compound structure:

or a pharmaceutically acceptable salt thereof, wherein each $R^1$ and $R^2$ is independently H or $C_1$-$C_6$ aliphatic; each m is independently an integer having a value of 1 to 4; each A is independently a covalent bond or arylene; each L is independently an ester, thioester, disulfide, or anhydride group; each $L^2$ is independently $C_2$-$C_{10}$ aliphatic; each $X^1$ is independently H or OH; and each $R^3$ is independently $C_6$-$C_{20}$ aliphatic. In some embodiments, the compositions and methods of the present invention include a cationic lipid of the following formula:

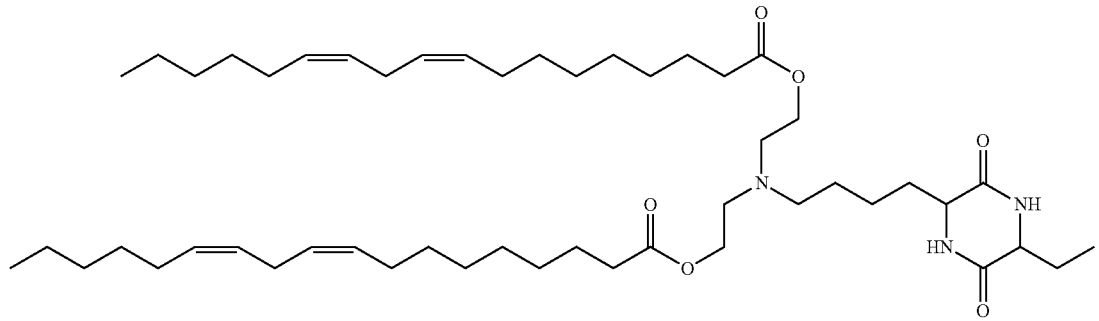 [SMILES: CCCCC/C=C\C/C=C\CCCCCCCC(=O)OCCN(CCCCC1NC(=O)C(CC)NC1=O)CCOC(=O)CCCCCCC/C=C\C/C=C\CCCCC]

or a pharmaceutically acceptable salt thereof. In some embodiments, the compositions and methods of the present invention include a cationic lipid having the compound structure:

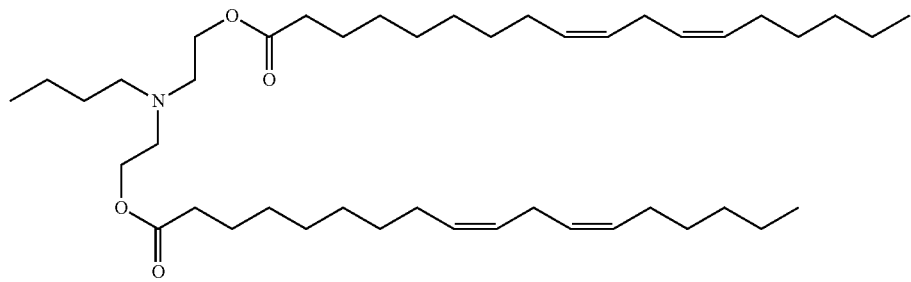 [SMILES: CCCCC/C=C\C/C=C\CCCCCCCC(=O)OCCN(CCCC)CCOC(=O)CCCCCCC/C=C\C/C=C\CCCCC]

or a pharmaceutically acceptable salt thereof.

Other suitable cationic lipids for use in the compositions and methods of the present invention include cationic lipids as described in U.S. Provisional Patent Application Ser. No. 62/758,179, which is incorporated herein by reference. In some embodiments, the compositions and methods of the present invention include a cationic lipid of the following formula:

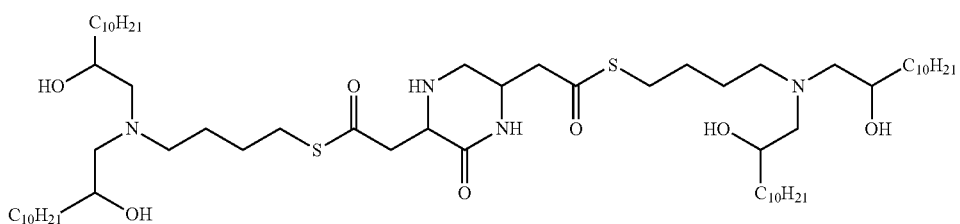

(Compound 1)

or a pharmaceutically acceptable salt thereof. In some embodiments, the compositions and methods of the present invention include a cationic lipid of the following formula:

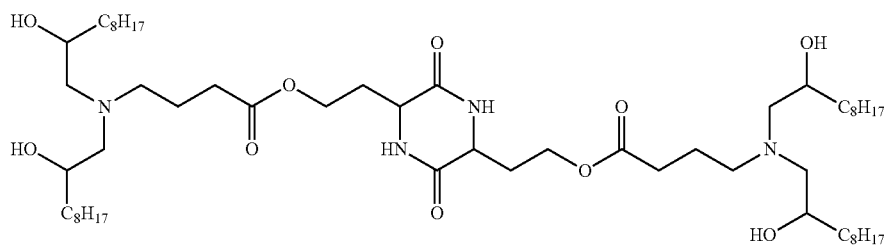

(Compound 2; cHse-E-3-E10; TBL-0098)

or a pharmaceutically acceptable salt thereof. In some embodiments, the compositions and methods of the present invention include a cationic lipid of the following formula:

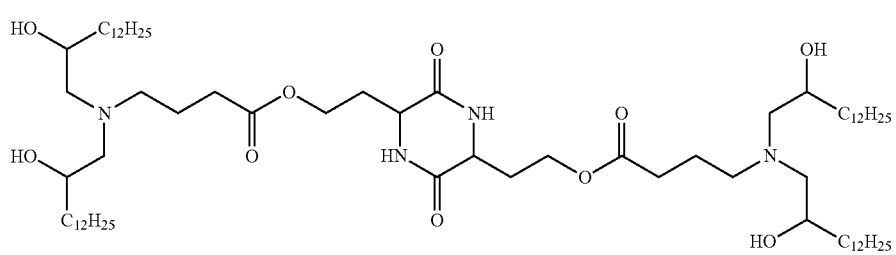

(Compound 3)

or a pharmaceutically acceptable salt thereof.

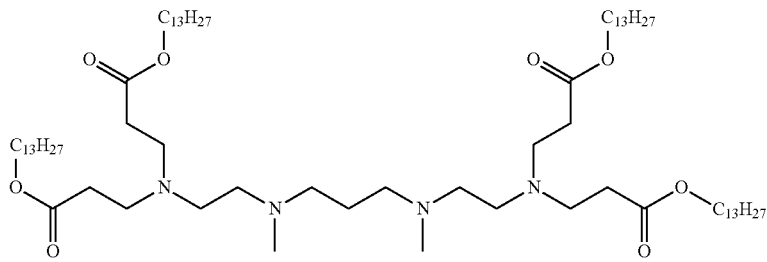

Other suitable cationic lipids for use in the compositions and methods of the present invention include the cationic lipids as described in J. McClellan, M. C. King, Cell 2010, 141, 210-217 and in Whitehead et al., Nature Communications (2014) 5:4277, which is incorporated herein by reference. In certain embodiments, the cationic lipids of the compositions and methods of the present invention include a cationic lipid having a compound structure of:

and pharmaceutically acceptable salts thereof.

Other suitable cationic lipids for use in the compositions and methods of the invention include the cationic lipids as described in International Patent Publication WO 2015/199952, which is incorporated herein by reference. In some embodiments, the compositions and methods of the present invention include a cationic lipid having the compound structure:

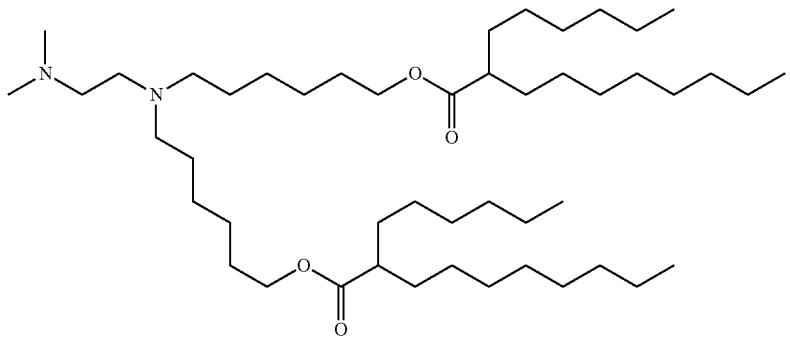 [SMILES: CCCCCCCCC(CCCCCC)C(=O)OCCCCCCN(CCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

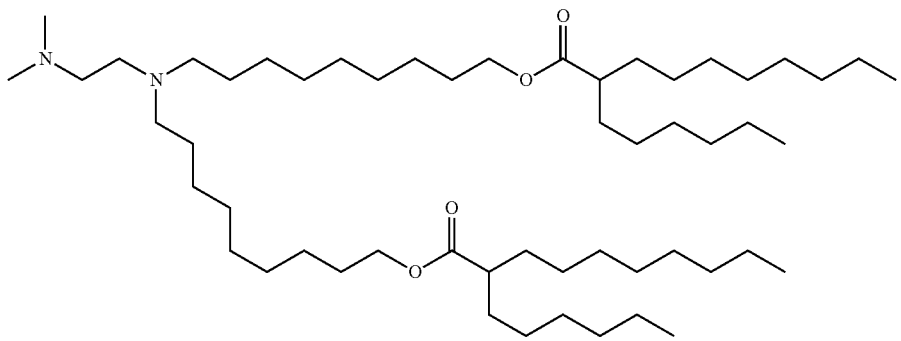 [SMILES: CCCCCCCCC(CCCCCC)C(=O)OCCCCCCCCCN(CCCCCCCCCOC(=O)C(CCCCCC)CCCCCCCC)CCN(C)C]

and pharmaceutically acceptable salts thereof. In some embodiments, the compositions and methods of the present invention include a cationic lipid having the compound structure:

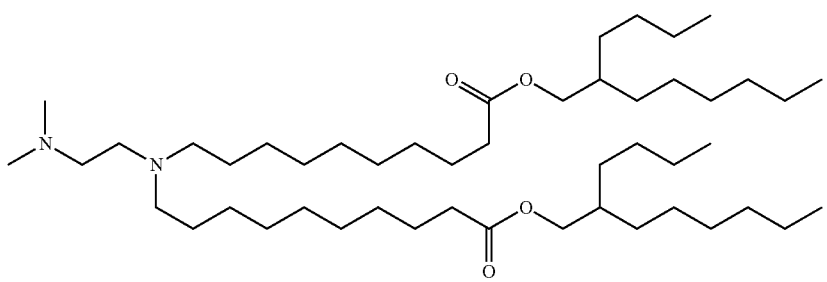 [SMILES: CCCCCCC(CCCC)COC(=O)CCCCCCCCCN(CCCCCCCCCC(=O)OCC(CCCC)CCCCCC)CCN(C)C]

and pharmaceutically acceptable salts thereof. In some embodiments, the compositions and methods of the present invention include a cationic lipid having the compound structure:

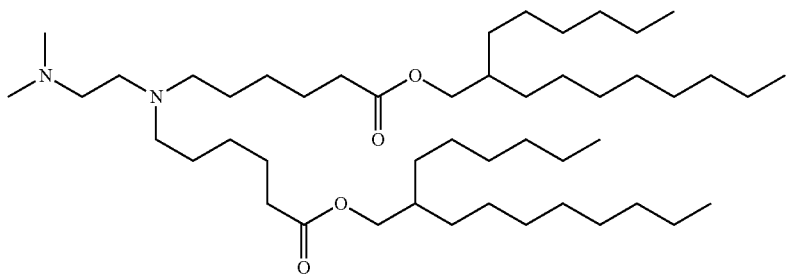 [SMILES: CCCCCCCCC(CCCCCC)COC(=O)CCCCCN(CCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

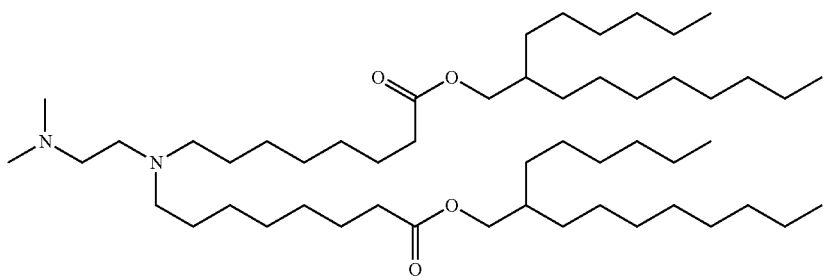 [SMILES: CCCCCCCCC(CCCCCC)COC(=O)CCCCCCCN(CCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

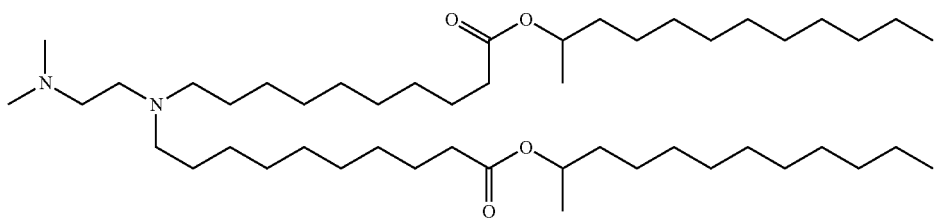 [SMILES: CCCCCCCCCCC(C)OC(=O)CCCCCCCCCN(CCCCCCCCCC(=O)OC(C)CCCCCCCCCC)CCN(C)C]

and pharmaceutically acceptable salts thereof. In some embodiments, the compositions and methods of the present invention include a cationic lipid having the compound structure:

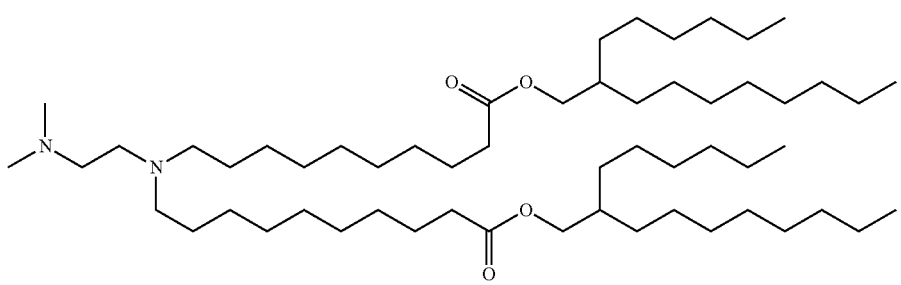 [SMILES: CCCCCCCCC(CCCCCC)COC(=O)CCCCCCCCCN(CCCCCCCCCC(=O)OCC(CCCCCC)CCCCCCCC)CCN(C)C]

and pharmaceutically acceptable salts thereof. In some embodiments, the compositions and methods of the present invention include a cationic lipid having the compound structure:

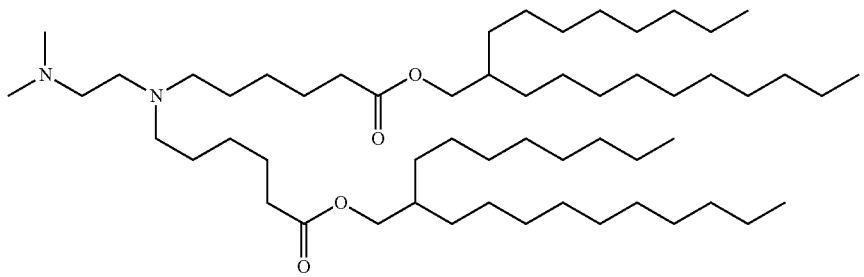 [SMILES: CCCCCCCCCCC(CCCCCCCC)COC(=O)CCCCCN(CCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

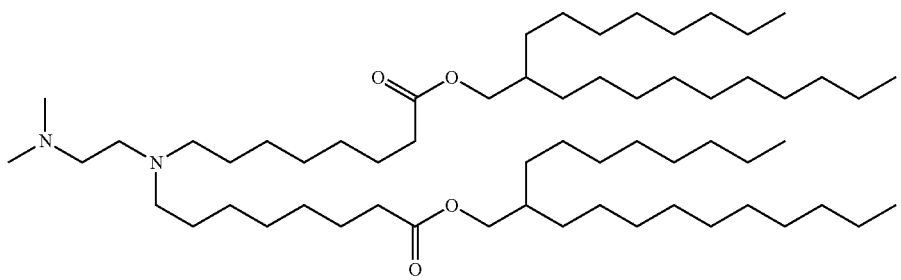 [SMILES: CCCCCCCCCCC(CCCCCCCC)COC(=O)CCCCCCCN(CCCCCCCC(=O)OCC(CCCCCCCC)CCCCCCCCCC)CCN(C)C]

and pharmaceutically acceptable salts thereof. In some embodiments, the compositions and methods of the present invention include a cationic lipid having the compound structure:

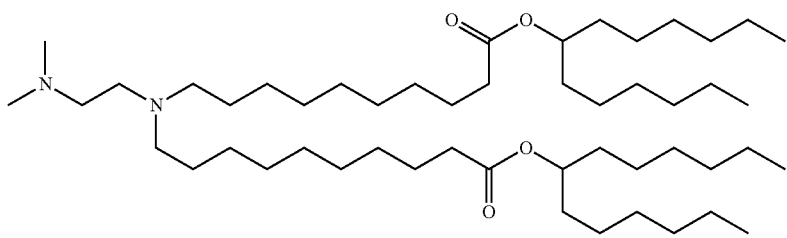 [SMILES: CCCCCCC(CCCCCC)OC(=O)CCCCCCCCCN(CCCCCCCCCC(=O)OC(CCCCCC)CCCCCC)CCN(C)C]

and pharmaceutically acceptable salts thereof. In some embodiments, the compositions and methods of the present invention include a cationic lipid having the compound structure:

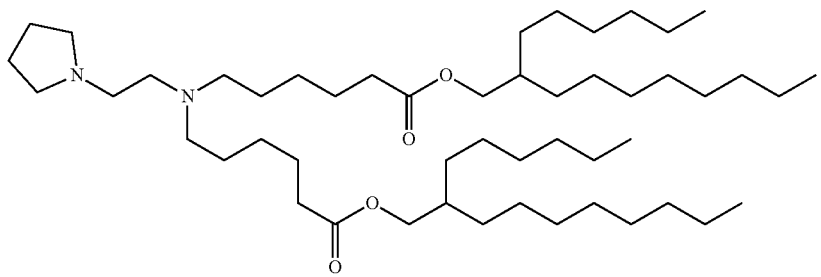 [SMILES: CCCCCCCCC(CCCCCC)COC(=O)CCCCCN(CCCCCC(=O)OCC(CCCCCC)CCCCCCCC)CCN1CCCC1]

and pharmaceutically acceptable salts thereof. In some embodiments, the compositions and methods of the present invention include a cationic lipid having the compound structure:

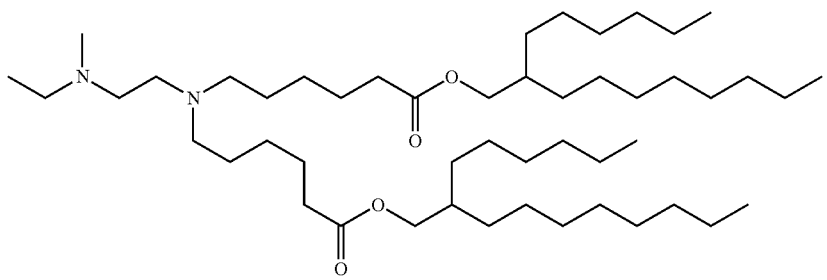 [SMILES: CCCCCCCCC(CCCCCC)COC(=O)CCCCCN(CCCCCC(=O)OCC(CCCCCC)CCCCCCCC)CCN(C)CC]

and pharmaceutically acceptable salts thereof. In some embodiments, the compositions and methods of the present invention include a cationic lipid having the compound structure:

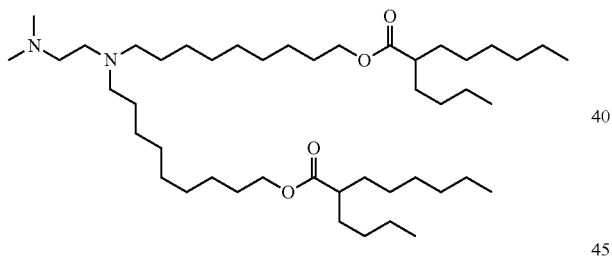

and pharmaceutically acceptable salts thereof.

Other suitable cationic lipids for use in the compositions and methods of the invention include the cationic lipids as described in International Patent Publication WO 2017/004143, which is incorporated herein by reference. In some embodiments, the compositions and methods of the present invention include a cationic lipid having the compound structure:

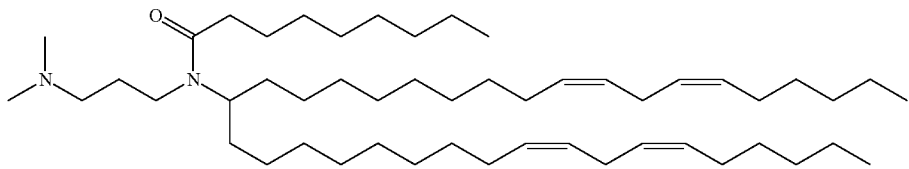 [SMILES: CCCCC/C=C\C/C=C\CCCCCCCCC(CCCCCCCC/C=C\C/C=C\CCCCC)N(CCCN(C)C)C(=O)CCCCCCCC]

and pharmaceutically acceptable salts thereof. In some embodiments, the compositions and methods of the present invention include a cationic lipid having the compound structure:

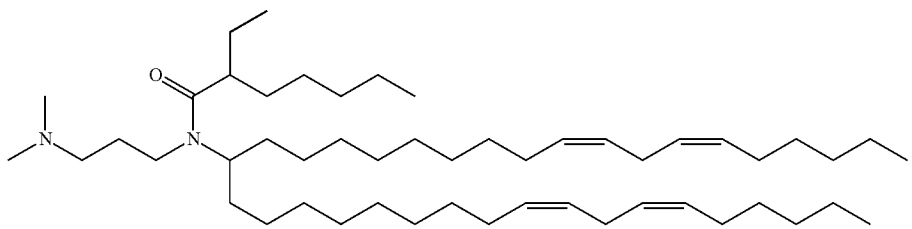 [SMILES: CCCCC/C=C\C/C=C\CCCCCCCCC(CCCCCCCC/C=C\C/C=C\CCCCC)N(CCCN(C)C)C(=O)C(CC)CCCCC]

and pharmaceutically acceptable salts thereof. In some embodiments, the compositions and methods of the present invention include a cationic lipid having the compound structure:

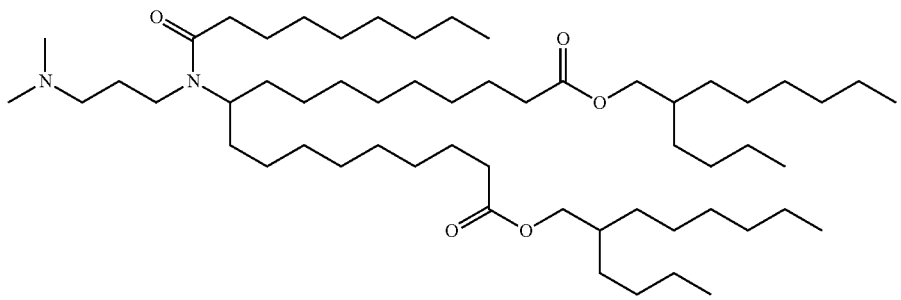 [SMILES: CCCCCCCCC(=O)N(CCCN(C)C)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

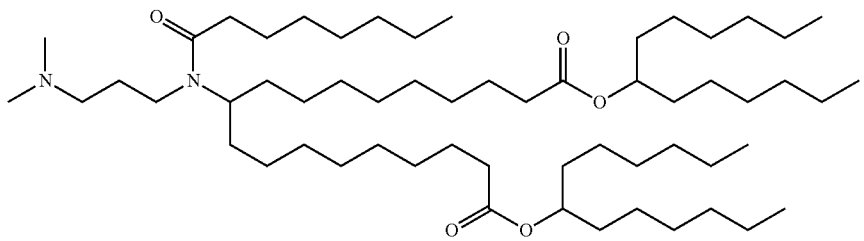 [SMILES: CCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

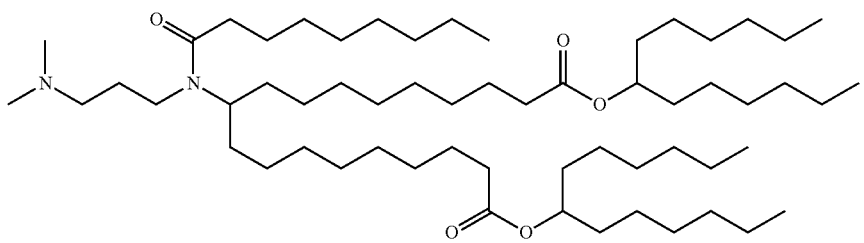 [SMILES: CCCCCCCCC(=O)N(CCCN(C)C)C(CCCCCCCCC(=O)OC(CCCCCC)CCCCCC)CCCCCCCCC(=O)OC(CCCCCC)CCCCCC]

and pharmaceutically acceptable salts thereof. In some embodiments, the compositions and methods of the present invention include a cationic lipid having the compound structure:

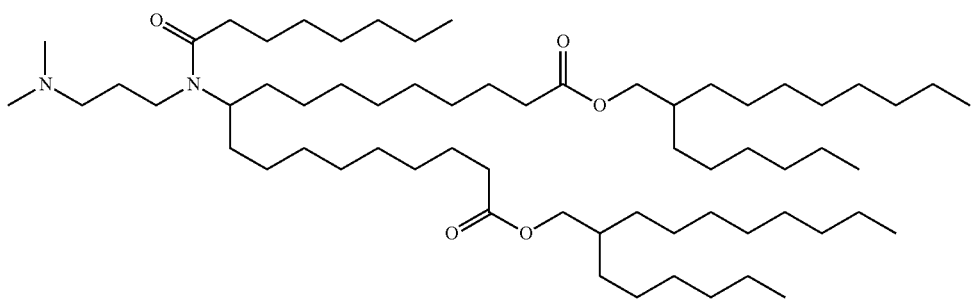 [SMILES: CCCCCCCCC(CCCCCC)COC(=O)CCCCCCCCC(CCCCCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

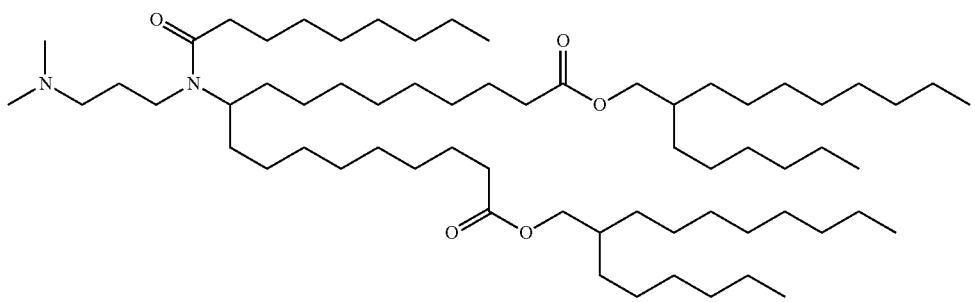 [SMILES: CCCCCCCCC(=O)N(CCCN(C)C)C(CCCCCCCCC(=O)OCC(CCCCCC)CCCCCCCC)CCCCCCCCC(=O)OCC(CCCCCC)CCCCCCCC]

and pharmaceutically acceptable salts thereof. In some embodiments, the compositions and methods of the present invention include a cationic lipid having the compound structure:

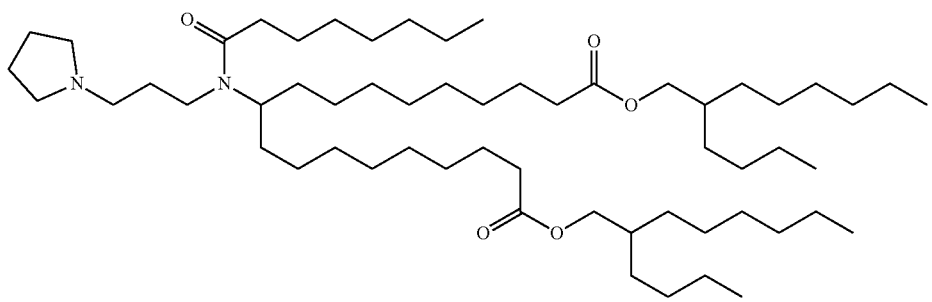 [SMILES: CCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

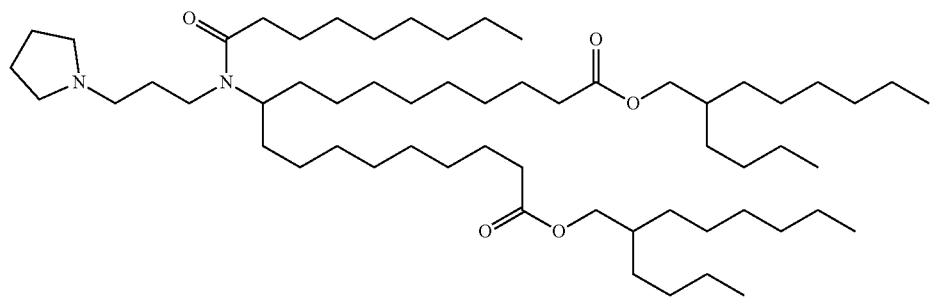 [SMILES: CCCCCCCCC(=O)N(CCCN1CCCC1)C(CCCCCCCCC(=O)OCC(CCCC)CCCCCC)CCCCCCCCC(=O)OCC(CCCC)CCCCCC]

and pharmaceutically acceptable salts thereof. In some embodiments, the compositions and methods of the present invention include a cationic lipid having the compound structure:

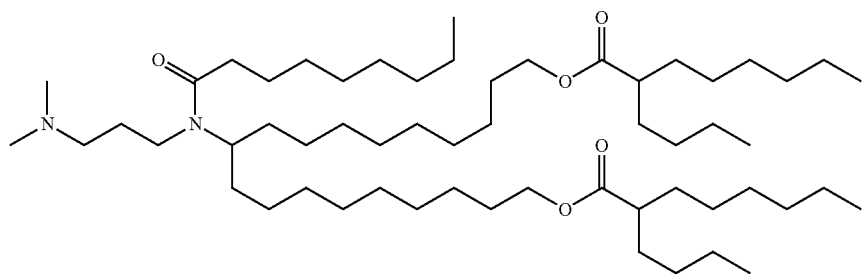 [SMILES: CCCCCCCCC(=O)N(CCCN(C)C)C(CCCCCCCCCOC(=O)C(CCCC)CCCCCC)CCCCCCCCCOC(=O)C(CCCC)CCCCCC]

and pharmaceutically acceptable salts thereof. In some embodiments, the compositions and methods of the present invention include a cationic lipid having the compound structure:

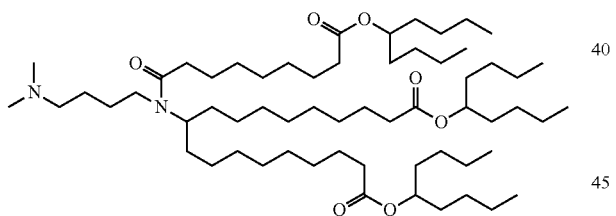

and pharmaceutically acceptable salts thereof. In some embodiments, the compositions and methods of the present invention include a cationic lipid having the compound structure:

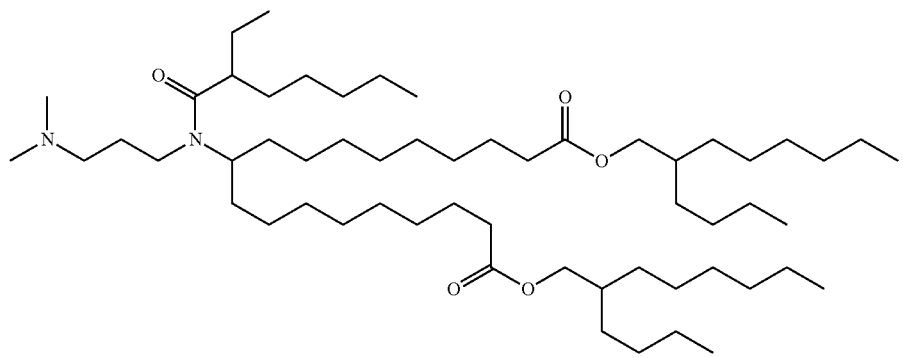 [SMILES: CCCCCCC(CCCC)COC(=O)CCCCCCCCC(CCCCCCCCC(=O)OCC(CCCC)CCCCCC)N(CCCN(C)C)C(=O)C(CC)CCCCC]

and pharmaceutically acceptable salts thereof. In some embodiments, the compositions and methods of the present invention include a cationic lipid having the compound structure:

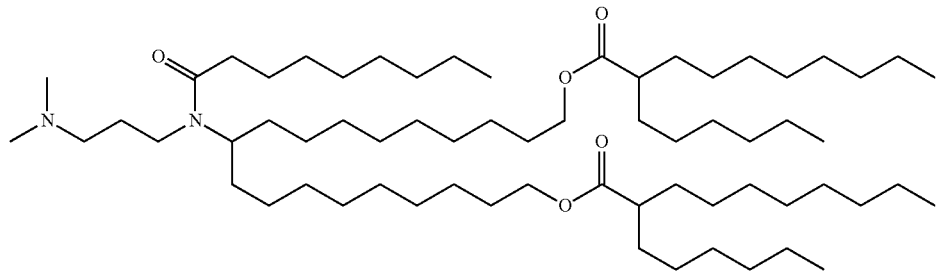 [SMILES: CCCCCCCCC(=O)N(CCCN(C)C)C(CCCCCCCCCOC(=O)C(CCCCCC)CCCCCCCC)CCCCCCCCCOC(=O)C(CCCCCC)CCCCCCCC]

and pharmaceutically acceptable salts thereof. In some embodiments, the compositions and methods of the present invention include a cationic lipid having the compound structure:

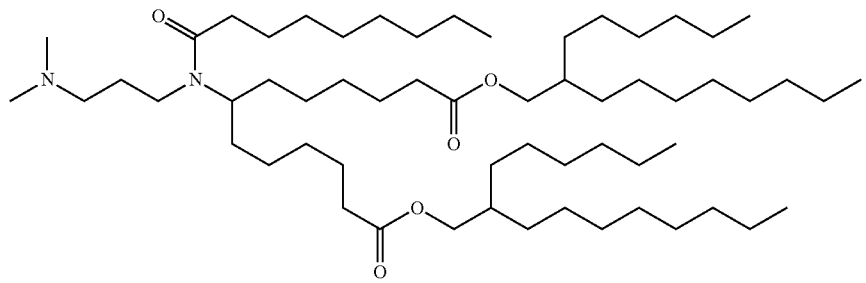 [SMILES: CCCCCCCCC(=O)N(CCCN(C)C)C(CCCCCC(=O)OCC(CCCCCC)CCCCCCCC)CCCCCC(=O)OCC(CCCCCC)CCCCCCCC]

and pharmaceutically acceptable salts thereof. In some embodiments, the compositions and methods of the present invention include a cationic lipid having the compound structure:

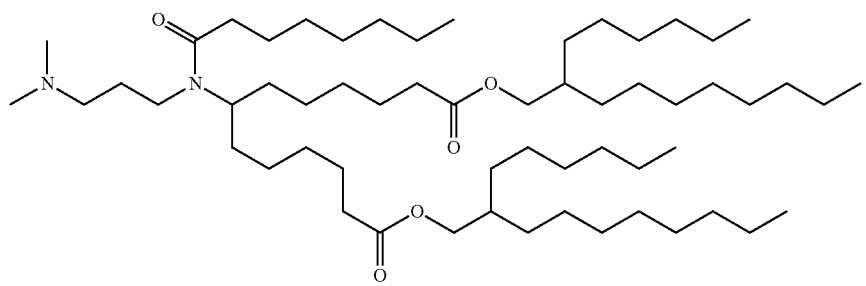 [SMILES: CCCCCCCCC(CCCCCC)COC(=O)CCCCCC(CCCCCC(=O)OCC(CCCCCC)CCCCCCCC)N(CCCN(C)C)C(=O)CCCCCCC]

and pharmaceutically acceptable salts thereof. In some embodiments, the compositions and methods of the present invention include a cationic lipid having the compound structure:

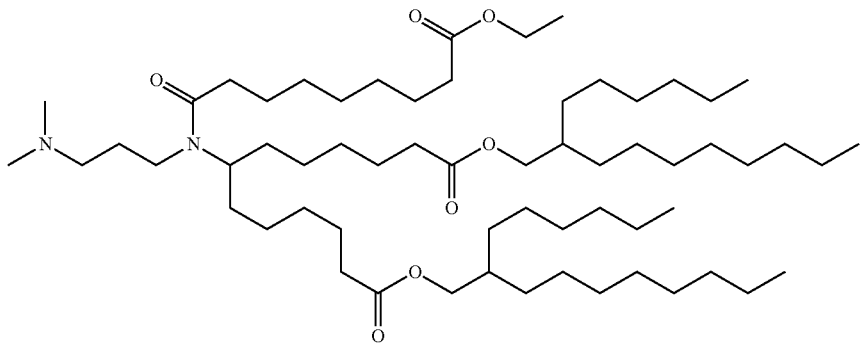 [SMILES: CCCCCCCCC(CCCCCC)COC(=O)CCCCCC(CCCCCC(=O)OCC(CCCCCC)CCCCCCCC)N(CCCN(C)C)C(=O)CCCCCCCC(=O)OCC]

and pharmaceutically acceptable salts thereof. In some embodiments, the compositions and methods of the present invention include a cationic lipid having the compound structure:

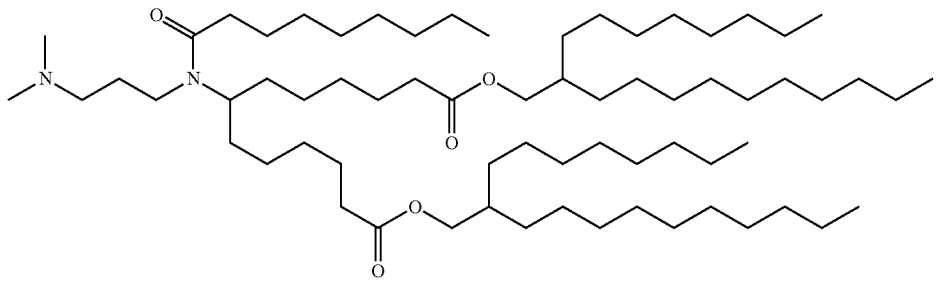 [SMILES: CCCCCCCCCCC(CCCCCCCC)COC(=O)CCCCCC(CCCCCC(=O)OCC(CCCCCCCC)CCCCCCCCCC)N(CCCN(C)C)C(=O)CCCCCCCC]

and pharmaceutically acceptable salts thereof.

Other suitable cationic lipids for use in the compositions and methods of the invention include the cationic lipids as described in International Patent Publication WO 2017/075531, which is incorporated herein by reference. In some embodiments, the compositions and methods of the present invention include a cationic lipid of the following formula:

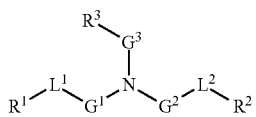

or a pharmaceutically acceptable salt thereof, wherein one of $L^1$ or $L^2$ is —O(C=O)—, —(C=O)O—, —C(=O)—, —O—, —S(O)$_x$, —S—S—, —C(=O)S—, —SC(=O)—, —NR$^a$C(=O)—, —C(=O)NR$^a$—, NR$^a$C(=O)NR$^a$—, —OC(=O)NR$^a$—, or —NR$^a$C(=O)O—; and the other of $L^1$ or $L^2$ is —O(C=O)—, —(C=O)O—, —C(=O)—, —O—, —S(O)$_x$, —S—S—, —C(=O)S—, SC(=O)—, —NR$^a$C(=O)—, —C(=O)NR$^a$—, NR$^a$C(=O)NR$^a$—, —OC(=O)NR$^a$— or —NR$^a$C(=O)O— or a direct bond; $G^1$ and $G^2$ are each independently unsubstituted $C_1$-$C_{12}$ alkylene or $C_1$-$C_{12}$ alkenylene; $G^3$ is $C_1$-$C_{24}$ alkylene, $C_1$-$C_{24}$ alkenylene, $C_3$-$C_8$ cycloalkylene, $C_3$-$C_8$ cycloalkenylene; $R^a$ is H or $C_1$-$C_{12}$ alkyl; $R^1$ and $R^2$ are each independently $C_6$-$C_{24}$ alkyl or $C_6$-$C_{24}$ alkenyl; $R^3$ is H, OR$^5$, CN, —C(=O)OR$^4$, —OC(=O)R$^4$ or —NR$^5$C(=O)R$^4$; $R^4$ is $C_1$-$C_{12}$ alkyl; $R^5$ is H or $C_1$-$C_6$ alkyl; and x is 0, 1 or 2.

Other suitable cationic lipids for use in the compositions and methods of the invention include the cationic lipids as described in International Patent Publication WO 2017/117528, which is incorporated herein by reference. In some embodiments, the compositions and methods of the present invention include a cationic lipid having the compound structure:

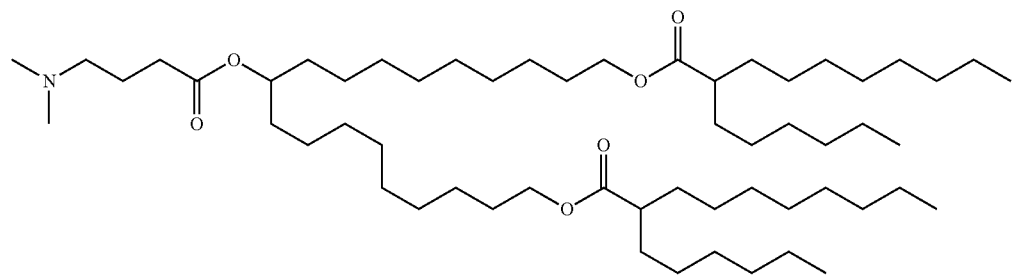 [SMILES: CCCCCCCCC(CCCCCC)C(=O)OCCCCCCCCCC(CCCCCCCCCOC(=O)C(CCCCCC)CCCCCCCC)OC(=O)CCCN(C)C]

and pharmaceutically acceptable salts thereof. In some embodiments, the compositions and methods of the present invention include a cationic lipid having the compound structure:

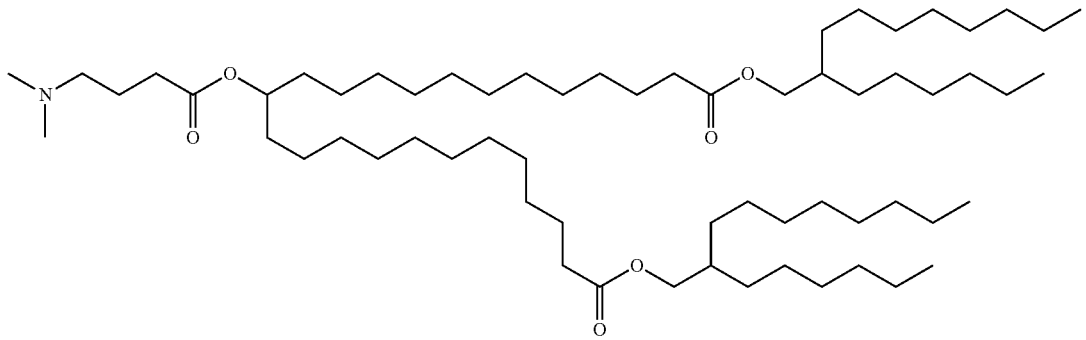 [SMILES: CCCCCCCCC(CCCCCC)COC(=O)CCCCCCCCCCCC(CCCCCCCCCCCC(=O)OCC(CCCCCC)CCCCCCCC)OC(=O)CCCN(C)C]

and pharmaceutically acceptable salts thereof. In some embodiments, the compositions and methods of the present invention include a cationic lipid having the compound structure:

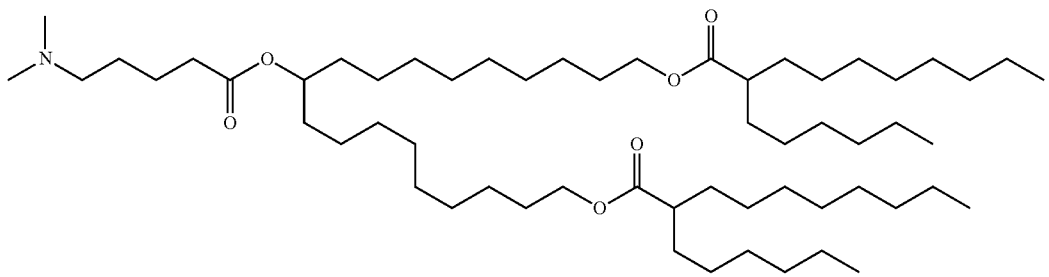 [SMILES: CCCCCCCCC(CCCCCC)C(=O)OCCCCCCCCCC(CCCCCCCCCOC(=O)C(CCCCCC)CCCCCCCC)OC(=O)CCCCN(C)C]

and pharmaceutically acceptable salts thereof.

Other suitable cationic lipids for use in the compositions and methods of the invention include the cationic lipids as described in International Patent Publication WO 2017/049245, which is incorporated herein by reference. In some embodiments, the cationic lipids of the compositions and methods of the present invention include a compound of one of the following formulas:

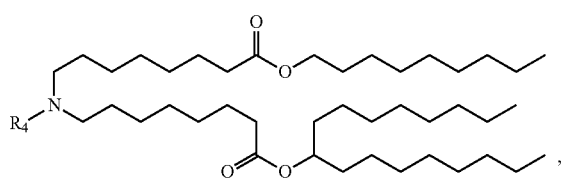

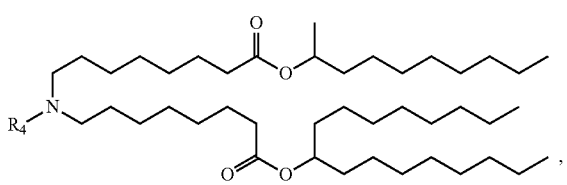

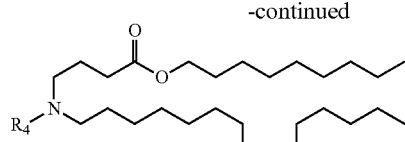

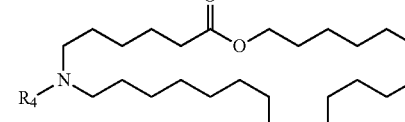

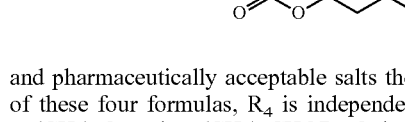

and pharmaceutically acceptable salts thereof. For any one of these four formulas, $R_4$ is independently selected from $-(CH_2)_nQ$ and $-(CH_2)_nCHQR$; Q is selected from the group consisting of $-OR$, $-OH$, $-O(CH_2)_nN(R)_2$, $-OC(O)R$, $-CX_3$, $-CN$, $-N(R)C(O)R$, $-N(H)C(O)R$, $-N(R)S(O)_2R$, $-N(H)S(O)_2R$, $-N(R)C(O)N(R)_2$, $-N(H)C(O)N(R)_2$, $-N(H)C(O)N(H)(R)$, $-N(R)C(S)N(R)_2$, $-N(H)C(S)N(R)_2$, $-N(H)C(S)N(H)(R)$, and a heterocycle; and n is 1, 2, or 3. In certain embodiments, the compositions and methods of the present invention include a cationic lipid having a compound structure of:

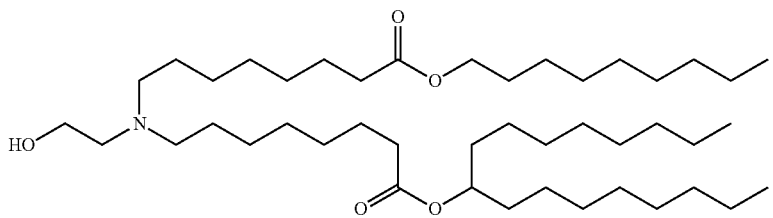 [SMILES: CCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

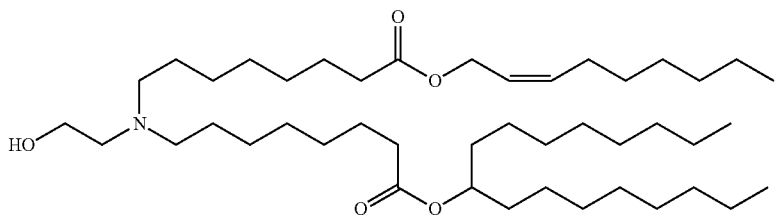 [SMILES: CCCCCC/C=C\COC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

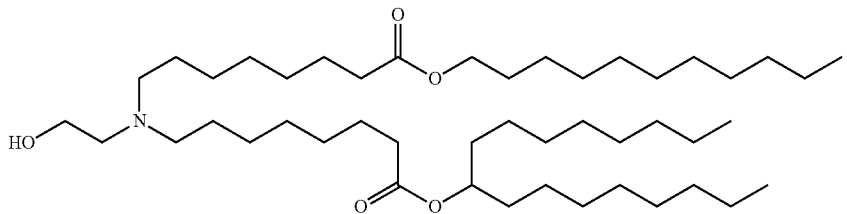 [SMILES: CCCCCCCCCCCOC(=O)CCCCCCCN(CCO)CCCCCCCC(=O)OC(CCCCCCCC)CCCCCCCC]

and pharmaceutically acceptable salts thereof. In certain embodiments, the compositions and methods of the present invention include a cationic lipid having a compound structure of:

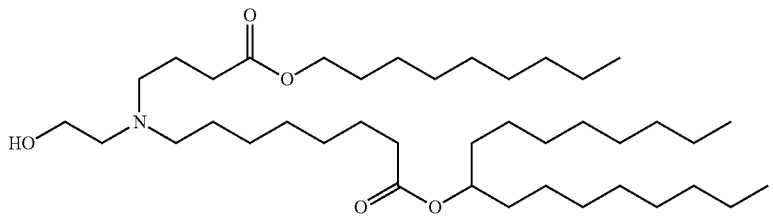 [SMILES: CCCCCCCCCOC(=O)CCCN(CCO)CCCCCCCC(=O)OC(CCCCCCCC)CCCCCCCC]

and pharmaceutically acceptable salts thereof.

Other suitable cationic lipids for use in the compositions and methods of the invention include the cationic lipids as described in International Patent Publication WO 2017/173054 and WO 2015/095340, each of which is incorporated herein by reference. In certain embodiments, the compositions and methods of the present invention include a cationic lipid having a compound structure of:

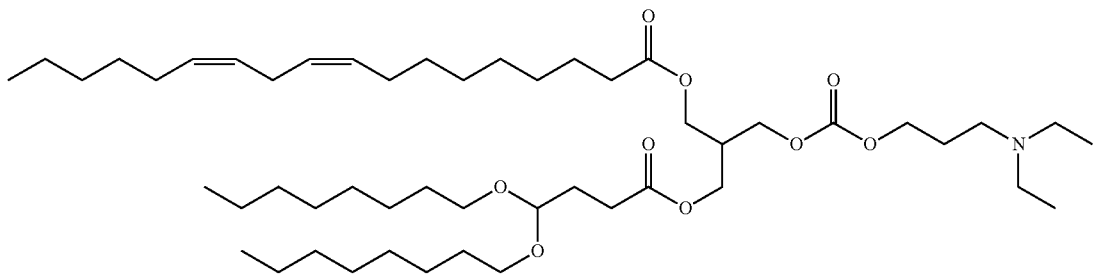

and pharmaceutically acceptable salts thereof. In certain embodiments, the compositions and methods of the present invention include a cationic lipid having a compound structure of:

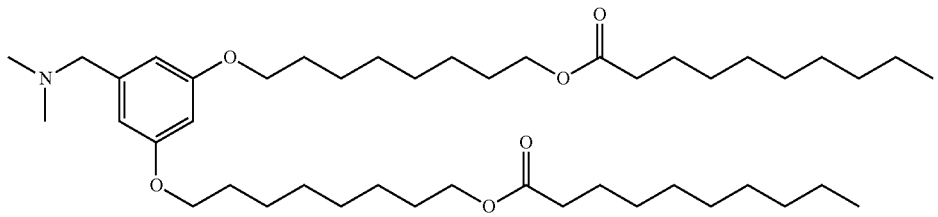 [SMILES: CCCCCCCCCC(=O)OCCCCCCCCOc1cc(CN(C)C)cc(OCCCCCCCCOC(=O)CCCCCCCCC)c1]

and pharmaceutically acceptable salts thereof. In certain embodiments, the compositions and methods of the present invention include a cationic lipid having a compound structure of:

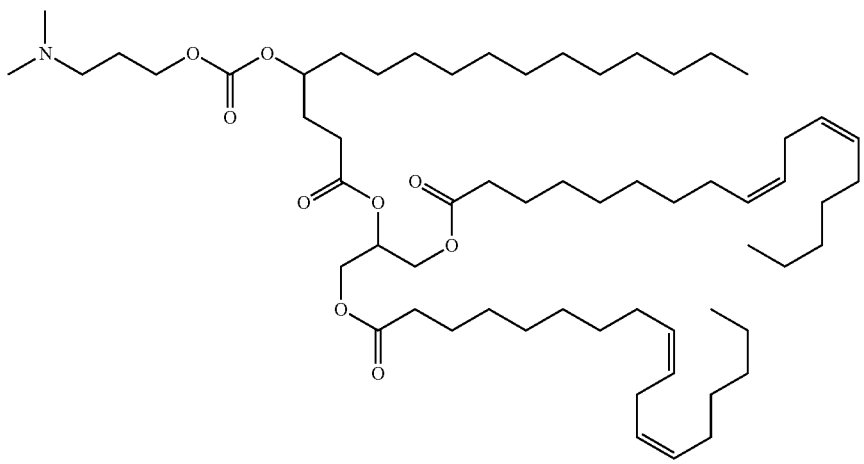 [SMILES: CCCCC/C=C\C/C=C\CCCCCCCC(=O)OCC(COC(=O)CCCCCCC/C=C\C/C=C\CCCCC)OC(=O)CCC(CCCCCCCCCCCC)OC(=O)OCCCN(C)C]

and pharmaceutically acceptable salts thereof. In certain embodiments, the compositions and methods of the present invention include a cationic lipid having a compound structure of:

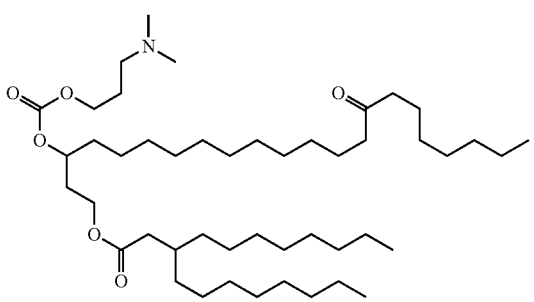 [SMILES: CCCCCCCCC(CCCCCCCC)CC(=O)OCCC(CCCCCCCCCCCC(=O)CCCCCCC)OC(=O)OCCCN(C)C]

and pharmaceutically acceptable salts thereof.

Other suitable cationic lipids for use in the compositions and methods of the present invention include cleavable cationic lipids as described in International Patent Publication WO 2012/170889, which is incorporated herein by reference. In some embodiments, the compositions and methods of the present invention include a cationic lipid of the following formula:

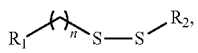

wherein $R_1$ is selected from the group consisting of imidazole, guanidinium, amino, imine, enamine, an optionally-substituted alkyl amino (e.g., an alkyl amino such as dimethylamino) and pyridyl; wherein $R_2$ is selected from the group consisting of one of the following two formulas:

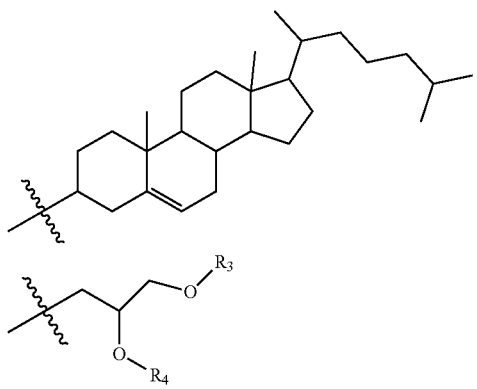

and wherein $R_3$ and $R_4$ are each independently selected from the group consisting of an optionally substituted, variably saturated or unsaturated $C_6$-$C_{20}$ alkyl and an optionally substituted, variably saturated or unsaturated $C_6$-$C_{20}$ acyl; and wherein n is zero or any positive integer (e.g., one, two, three, four, five, six, seven, eight, nine, ten, eleven, twelve, thirteen, fourteen, fifteen, sixteen, seventeen, eighteen, nineteen, twenty or more). In certain embodiments, the compositions and methods of the present invention include a cationic lipid, "HGT4001", having a compound structure of:

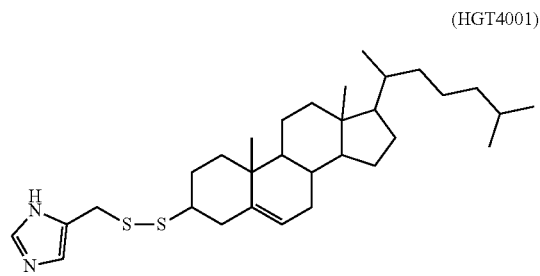 [SMILES: CC(C)CCCC(C)C1CCC2C3CC=C4CC(SSCc5cnc[nH]5)CCC4(C)C3CCC12C]

(HGT4001)

and pharmaceutically acceptable salts thereof. In certain embodiments, the compositions and methods of the present invention include a cationic lipid, "HGT4002," having a compound structure of:

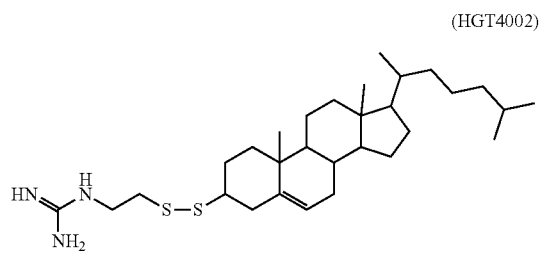 [SMILES: CC(C)CCCC(C)C1CCC2C3CC=C4CC(SSCCNC(=N)N)CCC4(C)C3CCC12C]

(HGT4002)

and pharmaceutically acceptable salts thereof. In certain embodiments, the compositions and methods of the present invention include a cationic lipid, "HGT4003," having a compound structure of:

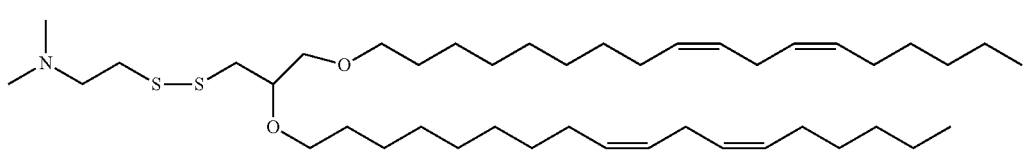

(HGT4003)

and pharmaceutically acceptable salts thereof. In certain embodiments, the compositions and methods of the present invention include a cationic lipid, "HGT4004," having a compound structure of:

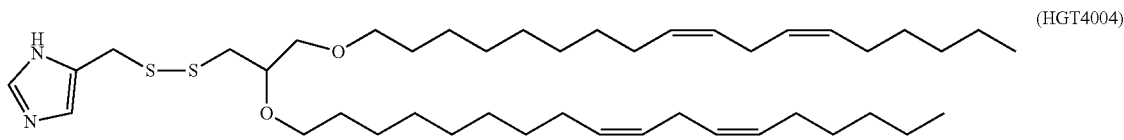 [SMILES: CCCCC/C=C\C/C=C\CCCCCCCCOCC(CSSCc1cnc[nH]1)OCCCCCCCC/C=C\C/C=C\CCCCC]
(HGT4004)

and pharmaceutically acceptable salts thereof. In certain embodiments, the compositions and methods of the present invention include a cationic lipid "HGT4005," having a compound structure of:

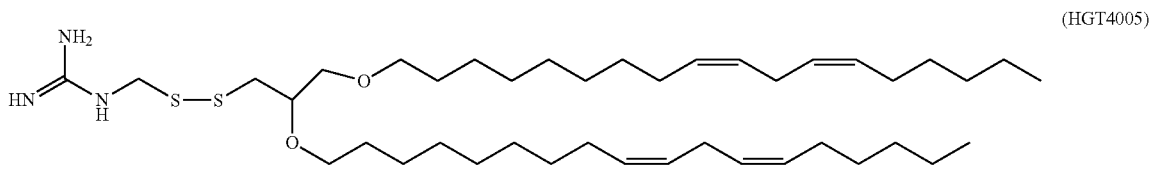 [SMILES: CCCCC/C=C\C/C=C\CCCCCCCCOCC(CSSCNC(=N)N)OCCCCCCCC/C=C\C/C=C\CCCCC]
(HGT4005)

and pharmaceutically acceptable salts thereof.

Other suitable cationic lipids for use in the compositions and methods of the present invention include cleavable cationic lipids as described in International Application No. PCT/US2019/032522, and incorporated herein by reference. In certain embodiments, the compositions and methods of the present invention include a cationic lipid that is any of general formulas or any of structures (1a)-(21a) and (1b)-(21b) and (22)-(237) described in International Application No. PCT/US2019/032522. In certain embodiments, the compositions and methods of the present invention include a cationic lipid that has a structure according to Formula (I'),

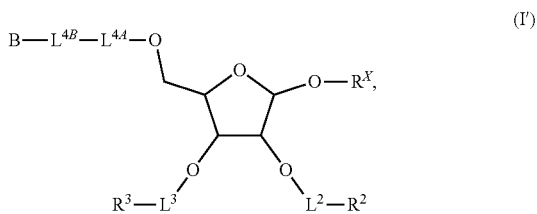
(I')

wherein:
$R^X$ is independently —H, -$L^1$-$R^1$, or -$L^{5A}$-$L^{5B}$-B';
each of $L^1$, $L^2$, and $L^3$ is independently a covalent bond, —C(O)—, —C(O)O—, —C(O)S—, or —C(O)NR$^L$—;
each $L^{4A}$ and $L^{5A}$ is independently —C(O)—, —C(O)O—, or —C(O)NR$^L$—;
each $L^{4B}$ and $L^{5B}$ is independently $C_1$-$C_{20}$ alkylene; $C_2$-$C_{20}$ alkenylene; or $C_2$-$C_{20}$ alkynylene;
each B and B' is NR$^4$R$^5$ or a 5- to 10-membered nitrogen-containing heteroaryl;
each $R^1$, $R^2$, and $R^3$ is independently $C_6$-$C_{30}$ alkyl, $C_6$-$C_{30}$ alkenyl, or $C_6$-$C_{30}$ alkynyl;
each $R^4$ and $R^5$ is independently hydrogen, $C_1$-$C_{10}$ alkyl; $C_2$-$C_{10}$ alkenyl; or $C_2$-$C_{10}$ alkynyl; and
each $R^L$ is independently hydrogen, $C_1$-$C_{20}$ alkyl, $C_2$-$C_{20}$ alkenyl, or $C_2$-$C_{20}$ alkynyl.

In certain embodiments, the compositions and methods of the present invention include a cationic lipid that is Compound (139) of International Application No. PCT/US2019/032522, having a compound structure of:

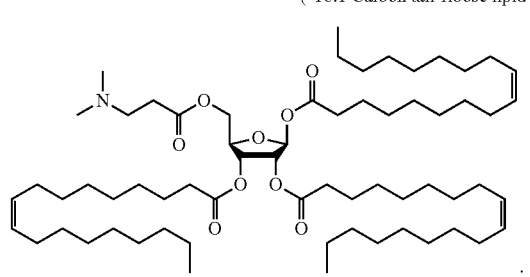
("18:1 Carbon tail-ribose lipid")

In some embodiments, the compositions and methods of the present invention include the cationic lipid, N-[1-(2,3-dioleyloxy)propyl]-N,N,N-trimethylammonium chloride ("DOTMA"). (Feigner et al. (Proc. Nat'l Acad. Sci. 84, 7413 (1987); U.S. Pat. No. 4,897,355, which is incorporated herein by reference). Other cationic lipids suitable for the compositions and methods of the present invention include, for example, 5-carboxyspermylglycinedioctadecylamide ("DOGS"); 2,3-dioleyloxy-N-[2(spermine-carboxamido) ethyl]-N,N-dimethyl-1-propanaminium ("DOSPA") (Behr et al. Proc. Nat.'l Acad. Sci. 86, 6982 (1989), U.S. Pat. Nos. 5,171,678; 5,334,761); 1,2-Dioleoyl-3-Dimethylammonium-Propane ("DODAP"); 1,2-Dioleoyl-3-Trimethylammonium-Propane ("DOTAP").

Additional exemplary cationic lipids suitable for the compositions and methods of the present invention also include: 1,2-distearyloxy-N,N-dimethyl-3-aminopropane ("DSDMA"); 1,2-dioleyloxy-N,N-dimethyl-3-aminopropane ("DODMA"); 1,2-dilinoleyloxy-N,N-dimethyl-3-aminopropane ("DLinDMA"); 1,2-dilinolenyloxy-N,N-dimethyl-3-aminopropane ("DLenDMA"); N-dioleyl-N,N-dimethylammonium chloride ("DODAC"); N,N-distearyl-N,N-dimethylammonium bromide ("DDAB"); N-(1,2-dimyristyloxyprop-3-yl)-N,N-dimethyl-N-hydroxyethyl ammonium bromide ("DMRIE"); 3-dimethylamino-2-(cholest-5-en-3-beta-oxybutan-4-oxy)-1-(cis,cis-9,12-octadecadienoxy)propane ("CLinDMA"); 2-[5'-(cholest-5-en-3-beta-oxy)-3'-oxapentoxy)-3-dimethyl-1-(cis,cis-9',1-2'-octadecadienoxy)propane ("CpLinDMA"); N,N-dimethyl-3,4-dioleyloxybenzylamine ("DMOBA"); 1,2-N,N'- dioleylcarbamyl-3-dimethylaminopropane ("DOcarbDAP"); 2,3-Dilinoleoyloxy-N,N-dimethylpropylamine ("DLinDAP"); 1,2-N,N'-Dilinoleylcarbamyl-3-dimethylaminopropane ("DLincarbDAP"); 1,2-Dilinoleoyl-carbamyl-3-dimethylaminopropane ("DLinCDAP"); 2,2-dilinoleyl-4-dimethylaminomethyl-[1,3]-dioxolane ("DLin-K-DMA"); 2-((8-[(3P)-cholest-5-en-3-yloxy]octyl)oxy)-N,N-dimethyl-3-[(9Z, 12Z)-octadeca-9, 12-dien-1-yloxy]propane-1-amine ("Octyl-CLinDMA"); (2R)-2-((8-[(3beta)-cholest-5-en-3-yloxy]octyl)oxy)-N, N-dimethyl-3-[(9Z, 12Z)-octadeca-9, 12-dien-1-yloxy]propan-1-amine ("Octyl-CLinDMA (2R)"); (2S)-2-((8-[(3P)-cholest-5-en-3-yloxy]octyl)oxy)-N, fsl-dimethyh3-[(9Z, 12Z)-octadeca-9, 12-dien-1-yloxy]propan-1-amine ("Octyl-CLinDMA (2S)"); 2,2-dilinoleyl-4-dimethylaminoethyl-[1,3]-dioxolane ("DLin-K-XTC2-DMA"); and 2-(2,2-di((9Z,12Z)-octadeca-9,12-dien-1-yl)-1,3-dioxolan-4-yl)-N,N-dimethylethanamine ("DLin-KC2-DMA") (see, WO 2010/042877, which is incorporated herein by reference; Semple et al., Nature Biotech. 28: 172-176 (2010)). (Heyes, J., et al., J Controlled Release 107: 276-287 (2005); Morrissey, D V., et al., Nat. Biotechnol. 23(8): 1003-1007 (2005); International Patent Publication WO 2005/121348). In some embodiments, one or more of the cationic lipids comprise at least one of an imidazole, dialkylamino, or guanidinium moiety.

In some embodiments, one or more cationic lipids suitable for the compositions and methods of the present invention include 2,2-Dilinoleyl-4-dimethylaminoethyl-[1,3]-dioxolane ("XTC"); (3aR,5s,6aS)—N,N-dimethyl-2,2-di((9Z, 12Z)-octadeca-9,12-dienyl)tetrahydro-3aH-cyclopenta[d][1,3]dioxol-5-amine ("ALNY-100") and/or 4,7,13-tris(3-oxo-3-(undecylamino)propyl)-N1,N16-diundecyl-4,7,10,13-tetraazahexadecane-1,16-diamide ("NC98-5").

In some embodiments, the compositions of the present invention include one or more cationic lipids that constitute at least about 5%, 10%, 20%, 30%, 35%, 40%, 45%, 50%, 55%, 60%, 65%, or 70%, measured by weight, of the total lipid content in the composition, e.g., a lipid nanoparticle. In some embodiments, the compositions of the present invention include one or more cationic lipids that constitute at least about 5%, 10%, 20%, 30%, 35%, 40%, 45%, 50%, 55%, 60%, 65%, or 70%, measured as a mol %, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured by weight, of the total lipid content in the composition, e.g., a lipid nanoparticle. In some embodiments, the compositions of the present invention include one or more cationic lipids that constitute about 30-70% (e.g., about 30-65%, about 30-60%, about 30-55%, about 30-50%, about 30-45%, about 30-40%, about 35-50%, about 35-45%, or about 35-40%), measured as mol %, of the total lipid content in the composition, e.g., a lipid nanoparticle.

Non-Cationic/Helper Lipids

In some embodiments, the liposomes contain one or more non-cationic ("helper") lipids. As used herein, the phrase "non-cationic lipid" refers to any neutral, zwitterionic or anionic lipid. As used herein, the phrase "anionic lipid" refers to any of a number of lipid species that carry a net negative charge at a selected pH, such as physiological pH. Non-cationic lipids include, but are not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoylphosphatidylcholine (POPC), palmitoyloleoyl-phosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidylethanolamine (DSPE), phosphatidylserine, sphingolipids, cerebrosides, gangliosides, 16-O-monomethyl PE, 16-O-dimethyl PE, 18-1-trans PE,1-stearoyl-2-oleoyl-phosphatidyethanolamine (SOPE), or a mixture thereof.

In some embodiments, a non-cationic lipid is a neutral lipid, i.e., a lipid that does not carry a net charge in the conditions under which the composition is formulated and/or administered.

In some embodiments, such non-cationic lipids may be used alone, but are preferably used in combination with other lipids, for example, cationic lipids.

In some embodiments, a non-cationic lipid may be present in a molar ratio (mol %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, total non-cationic lipids may be present in a molar ratio (mol %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, the percentage of non-cationic lipid in a liposome may be greater than about 5 mol %, greater than about 10 mol %, greater than about 20 mol %, greater than about 30 mol %, or greater than about 40 mol %. In some embodiments, the percentage total non-cationic lipids in a liposome may be greater than about 5 mol %, greater than about 10 mol %, greater than about 20 mol %, greater than about 30 mol %, or greater than about 40 mol %. In some embodiments, the percentage of non-cationic lipid in a liposome is no more than about 5 mol %, no more than about 10 mol %, no more than about 20 mol %, no more than about 30 mol %, or no more than about 40 mol %. In some embodiments, the percentage total non-cationic lipids in a liposome may be no more than about 5 mol %, no more than about 10 mol %, no more than about 20 mol %, or no more than about 30 mol %, or no more than about 40 mol %.

In some embodiments, a non-cationic lipid may be present in a weight ratio (wt %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, total non-cationic lipids may be present in a weight ratio (wt %) of about 5% to about 90%, about 5% to about 70%, about 5% to about 50%, about 5% to about 40%, about 5% to about 30%, about 10% to about 70%, about 10% to about 50%, or about 10% to about 40% of the total lipids present in a composition. In some embodiments, the percentage of non-cationic lipid in a liposome may be greater than about 5 wt %, greater than about 10 wt %, greater than about 20 wt %, greater than about 30 wt %, or greater than about 40 wt %. In some embodiments, the percentage total non-cationic lipids in a liposome may be greater than about 5 wt %, greater than about 10 wt %, greater than about 20 wt %, greater than about 30 wt %, or greater than about 40 wt %. In some embodiments, the percentage of non-cationic lipid in a liposome is no more than about 5 wt %, no more than about 10 wt %, no more than about 20 wt %, no more than about 30 wt %, or no more than about 40 wt %. In some embodiments, the percentage total non-cationic lipids in a liposome may be no more than about 5 wt %, no more than about 10 wt %, no more than about 20 wt %, no more than about 30 wt %, or no more than about 40 wt %.

Cholesterol-Based Lipids

In some embodiments, the liposomes comprise one or more cholesterol-based lipids. For example, suitable cholesterol-based cationic lipids include, for example, DC-Choi (N,N-dimethyl-N-ethylcarboxamidocholesterol),1,4-bis(3-N-oleylamino-propyl)piperazine (Gao, et al. Biochem. Biophys. Res. Comm. 179, 280 (1991); Wolf et al. BioTechniques 23, 139 (1997); U.S. Pat. No. 5,744,335), or imidazole cholesterol ester (ICE), which has the following structure,

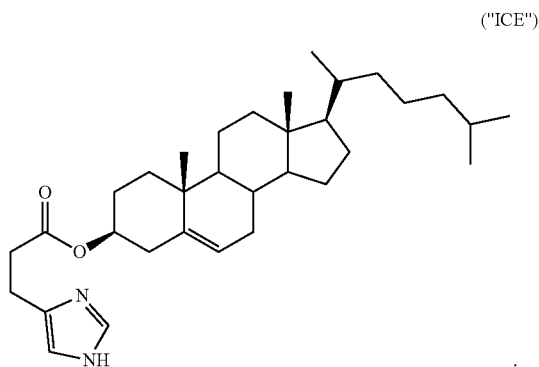 [SMILES: CC(C)CCCC(C)[C@H]1CCC2C3CC=C4C[C@@H](OC(=O)CCc5c[nH]cn5)CC[C@]4(C)C3CC[C@@]21C]

("ICE")

In embodiments, a cholesterol-based lipid is cholesterol.

In some embodiments, the cholesterol-based lipid may comprise a molar ratio (mol %) of about 1% to about 30%, or about 5% to about 20% of the total lipids present in a liposome. In some embodiments, the percentage of cholesterol-based lipid in the lipid nanoparticle may be greater than about 5 mol %, greater than about 10 mol %, greater than about 20 mol %, greater than about 30 mol %, or greater than about 40 mol %. In some embodiments, the percentage of cholesterol-based lipid in the lipid nanoparticle may be no more than about 5 mol %, no more than about 10 mol %, no more than about 20 mol %, no more than about 30 mol %, or no more than about 40 mol %.

In some embodiments, a cholesterol-based lipid may be present in a weight ratio (wt %) of about 1% to about 30%, or about 5% to about 20% of the total lipids present in a liposome. In some embodiments, the percentage of cholesterol-based lipid in the lipid nanoparticle may be greater than about 5 wt %, greater than about 10 wt %, greater than about 20 wt %, greater than about 30 wt %, or greater than about 40 wt %. In some embodiments, the percentage of cholesterol-based lipid in the lipid nanoparticle may be no more than about 5 wt %, no more than about 10 wt %, no more than about 20 wt %, no more than about 30 wt %, or no more than about 40 wt %.

PEG-Modified Lipids

In some embodiments, the liposome comprises one or more PEGylated lipids.

For example, the use of polyethylene glycol (PEG)-modified phospholipids and derivatized lipids such as derivatized ceramides (PEG-CER), including N-Octanoyl-Sphingosine-1-[Succinyl(Methoxy Polyethylene Glycol)-2000] (C8 PEG-2000 ceramide) is also contemplated by the present invention, either alone or preferably in combination with other lipid formulations together which comprise the transfer vehicle (e.g., a lipid nanoparticle).

Contemplated PEG-modified lipids include, but are not limited to, a polyethylene glycol chain of up to 5 kDa in length covalently attached to a lipid with alkyl chain(s) of $C_6$-$C_{20}$ length. In some embodiments, a PEG-modified or PEGylated lipid is PEGylated cholesterol or PEG-2K. The addition of such components may prevent complex aggregation and may also provide a means for increasing circulation lifetime and increasing the delivery of the lipid-nucleic acid composition to the target tissues, (Klibanov et al. (1990) FEBS Letters, 268 (1): 235-237), or they may be selected to rapidly exchange out of the formulation in vivo (see U.S. Pat. No. 5,885,613). Particularly useful exchangeable lipids are PEG-ceramides having shorter acyl chains (e.g., $C_{14}$ or $C_{18}$).

The PEG-modified phospholipid and derivitized lipids of the present invention may comprise a molar ratio from about 0% to about 20%, about 0.5% to about 20%, about 1% to about 15%, about 4% to about 10%, or about 2% of the total lipid present in the liposomal transfer vehicle. In some embodiments, one or more PEG-modified lipids constitute about 4% of the total lipids by molar ratio. In some embodiments, one or more PEG-modified lipids constitute about 5% of the total lipids by molar ratio. In some embodiments, one or more PEG-modified lipids constitute about 6% of the total lipids by molar ratio.

Amphiphilic Block Copolymers

In some embodiments, a suitable delivery vehicle contains amphiphilic block copolymers (e.g., poloxamers).

Various amphiphilic block copolymers may be used to practice the present invention. In some embodiments, an amphiphilic block copolymer is also referred to as a surfactant or a non-ionic surfactant.

In some embodiments, an amphiphilic polymer suitable for the invention is selected from poloxamers (Pluronic®), poloxamines (Tetronic®), polyoxyethylene glycol sorbitan alkyl esters (polysorbates) and polyvinyl pyrrolidones (PVPs).

Poloxamers

In some embodiments, a suitable amphiphilic polymer is a poloxamer. For example, a suitable poloxamer is of the following structure:

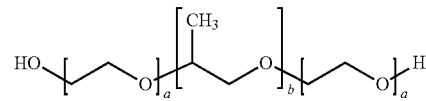

wherein a is an integer between 10 and 150 and b is an integer between 20 and 60. For example, a is about 12 and b is about 20, or a is about 80 and b is about 27, or a is about 64 and b is about 37, or a is about 141 and b is about 44, or a is about 101 and b is about 56.

In some embodiments, a poloxamer suitable for the invention has ethylene oxide units from about 10 to about 150. In some embodiments, a poloxamer has ethylene oxide units from about 10 to about 100.

In some embodiments, a suitable poloxamer is poloxamer 84. In some embodiments, a suitable poloxamer is poloxamer 101. In some embodiments, a suitable poloxamer is poloxamer 105. In some embodiments, a suitable poloxamer is poloxamer 108. In some embodiments, a suitable poloxamer is poloxamer 122. In some embodiments, t a suitable poloxamer is poloxamer 123. In some embodiments, a suitable poloxamer is poloxamer 124. In some embodiments, a suitable poloxamer is poloxamer 181. In some embodiments, a suitable poloxamer is poloxamer 182. In some embodiments, a suitable poloxamer is poloxamer 183. In some embodiments, a suitable poloxamer is poloxamer 184. In some embodiments, a suitable poloxamer is poloxamer 185. In some embodiments, a suitable poloxamer is poloxamer 188. In some embodiments, a suitable poloxamer is poloxamer 212. In some embodiments, a suitable poloxamer is poloxamer 215. In some embodiments, a suitable poloxamer is poloxamer 217. In some embodiments, a suitable poloxamer is poloxamer 231. In some embodiments, a suitable poloxamer is poloxamer 234. In some embodiments, a suitable poloxamer is poloxamer 235. In some embodiments, a suitable poloxamer is poloxamer 237. In some embodiments, a suitable poloxamer is poloxamer 238. In some embodiments, a suitable poloxamer is poloxamer 282. In some embodiments, a suitable poloxamer is poloxamer 284. In some embodiments, a suitable poloxamer is poloxamer 288. In some embodiments, a suitable poloxamer is poloxamer 304. In some embodiments, a suitable poloxamer is poloxamer 331. In some embodiments, a suitable poloxamer is poloxamer 333. In some embodiments, a suitable poloxamer is poloxamer 334. In some embodiments, a suitable poloxamer is poloxamer 335. In some embodiments, a suitable poloxamer is poloxamer 338. In some embodiments, a suitable poloxamer is poloxamer 401. In some embodiments, a suitable poloxamer is poloxamer 402. In some embodiments, a suitable poloxamer is poloxamer 403. In some embodiments, a suitable poloxamer is poloxamer 407. In some embodiments, a suitable poloxamer is a combination thereof.

In some embodiments, a suitable poloxamer has an average molecular weight of about 4,000 g/mol to about 20,000 g/mol. In some embodiments, a suitable poloxamer has an average molecular weight of about 1,000 g/mol to about 50,000 g/mol. In some embodiments, a suitable poloxamer has an average molecular weight of about 1,000 g/mol. In some embodiments, a suitable poloxamer has an average molecular weight of about 2,000 g/mol. In some embodiments, a suitable poloxamer has an average molecular weight of about 3,000 g/mol. In some embodiments, a suitable poloxamer has an average molecular weight of about 4,000 g/mol. In some embodiments, a suitable poloxamer has an average molecular weight of about 5,000 g/mol. In some embodiments, a suitable poloxamer has an average molecular weight of about 6,000 g/mol. In some embodiments, a suitable poloxamer has an average molecular weight of about 7,000 g/mol. In some embodiments, a suitable poloxamer has an average molecular weight of about 8,000 g/mol. In some embodiments, a suitable poloxamer has an average molecular weight of about 9,000 g/mol. In some embodiments, a suitable poloxamer has an average molecular weight of about 10,000 g/mol. In some embodiments, a suitable poloxamer has an average molecular weight of about 20,000 g/mol. In some embodiments, a suitable poloxamer has an average molecular weight of about 25,000 g/mol. In some embodiments, a suitable poloxamer has an average molecular weight of about 30,000 g/mol. In some embodiments, a suitable poloxamer has an average molecular weight of about 40,000 g/mol. In some embodiments, a suitable poloxamer has an average molecular weight of about 50,000 g/mol.

Other Amphiphilic Polymers

In some embodiments, an amphiphilic polymer is a poloxamine, e.g., tetronic 304 or tetronic 904.

In some embodiments, an amphiphilic polymer is a polyvinylpyrrolidone (PVP), such as PVP with molecular weight of 3 kDa, 10 kDa, or 29 kDa.

In some embodiments, an amphiphilic polymer is a polyethylene glycol ether (Brij), polysorbate, sorbitan, and derivatives thereof. In some embodiments, an amphiphilic polymer is a polysorbate, such as PS 20.

In some embodiments, an amphiphilic polymer is polyethylene glycol ether (Brij), poloxamer, polysorbate, sorbitan, or derivatives thereof.

In some embodiments, an amphiphilic polymer is a polyethylene glycol ether. In some embodiments, a suitable polyethylene glycol ether is a compound of Formula (S-1):

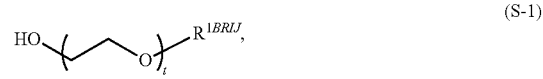

(S-1)

or a salt or isomer thereof, wherein:

t is an integer between 1 and 100;

$R^{1BRU}$ independently is $C_{10-40}$ alkyl, $C_{10-40}$ alkenyl, or $C_{10-40}$ alkynyl; and optionally one or more methylene groups of $R^{5PEG}$ are independently replaced with $C_{3-10}$ carbocyclylene, 4 to 10 membered heterocyclylene, $C_{6-10}$ arylene, 4 to 10 membered heteroarylene, —N($R^N$)—, —S—, —C(O)—, —C(O)N($R^N$)—, —N$R^N$C(O)—, —NRC(O)N(R)—, —C(O)O— —OC(O)—, —OC(O)O— —OC(O)N($R^N$)—, —N$R^N$C(O)O— —C(O)S— —SC(O)—, —C(=N$R^N$)—, C(=NR)N(R), —NRNC(=N$R^N$)— —N$R^N$C(=N$R^N$)N($R^N$)—, —C(S)—, —C(S)N($R^N$)—, —N$R^N$C(S)—, —N$R^N$C(S)N($R^N$), —S(O)—, —OS(O)—, —S(O)O— —OS(O)O— —OS(O)$_2$— —S(O)$_2$O— —OS(O)$_2$O— —N($R^N$)S(O)—, —S(O)N($R^N$)— —N($R^N$)S(O)N($R^N$)— —OS(O)N($R^N$)— —N($R^N$)S(O)O— —S(O)$_2$— —N($R^N$)S(O)$_2$— —S(O)$_2$N($R^N$)— —N($R^N$)S(O)$_2$N($R^N$)— —OS(O)$_2$N($R^N$)— or —N($R^N$)S(O)$_2$O—; and each instance of $R^N$ is independently hydrogen, $C_{1-6}$ alkyl, or a nitrogen protecting group.

In some embodiment, $R^{1BRU}$ is C is alkyl. For example, the polyethylene glycol ether is a compound of Formula (S-1a):

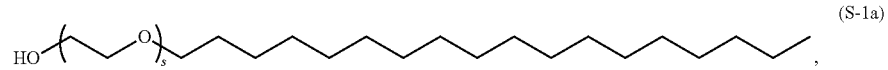

(S-1a)

or a salt or isomer thereof, wherein s is an integer between 1 and 100.

In some embodiments, $R^{1BRU}$ is C is alkenyl. For example, a suitable polyethylene glycol ether is a compound of Formula (S-1b):

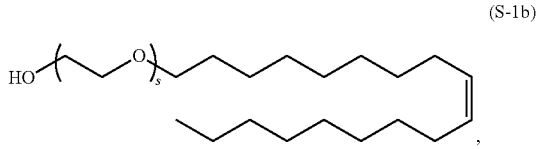

(S-1b)

or a salt or isomer thereof, wherein s is an integer between 1 and 100.

Typically, an amphiphilic polymer (e.g., a poloxamer) is present in a formulation at an amount lower than its critical micelle concentration (CMC). In some embodiments, an amphiphilic polymer (e.g., a poloxamer) is present in the mixture at an amount about 1%, about 2%, about 3%, about 4%, about 5%, about 6%, about 7%, about 8%, about 9%, about 10%, about 15%, about 20%, about 25%, about 30%, about 35%, about 40%, about 45%, or about 50% lower than its CMC. In some embodiments, an amphiphilic polymer (e.g., a poloxamer) is present in the mixture at an amount about 0.9%, 0.8%, 0.7%, 0.6%, 0.5%, 0.4%, 0.3%, 0.2%, 0.1% lower than its CMC. In some embodiments, an amphiphilic polymer (e.g., a poloxamer) is present in the mixture at an amount about 55%, 60%, 65%, 70%, 75%, 80%, 90%, or 95% lower than its CMC.

In some embodiments, less than about 0.1%, 0.09%, 0.08%, 0.07%, 0.06%, 0.05%, 0.04%, 0.03%, 0.02%, or 0.01% of the original amount of the amphiphilic polymer (e.g., the poloxamer) present in the formulation remains upon removal. In some embodiments, a residual amount of the amphiphilic polymer (e.g., the poloxamer) remains in a formulation upon removal. As used herein, a residual amount means a remaining amount after substantially all of the substance (an amphiphilic polymer described herein such as a poloxamer) in a composition is removed. A residual amount may be detectable using a known technique qualitatively or quantitatively. A residual amount may not be detectable using a known technique.

In some embodiments, a suitable delivery vehicle comprises less than 5% amphiphilic block copolymers (e.g., poloxamers). In some embodiments, a suitable delivery vehicle comprises less than 3% amphiphilic block copolymers (e.g., poloxamers). In some embodiments, a suitable delivery vehicle comprises less than 2.5% amphiphilic block copolymers (e.g., poloxamers). In some embodiments, suitable delivery vehicle comprises less than 2% amphiphilic block copolymers (e.g., poloxamers). In some embodiments, a suitable delivery vehicle comprises less than 1.5% amphiphilic block copolymers (e.g., poloxamers). In some embodiments, a suitable delivery vehicle comprises less than 1% amphiphilic block copolymers (e.g., poloxamers). In some embodiments, a suitable delivery vehicle comprises less than 0.5% (e.g., less than 0.4%, 0.3%, 0.2%, 0.1%) amphiphilic block copolymers (e.g., poloxamers). In some embodiments, a suitable delivery vehicle comprises less than 0.09%, 0.08%, 0.07%, 0.06%, 0.05%, 0.04%, 0.03%, 0.02%, or 0.01% amphiphilic block copolymers (e.g., poloxamers). In some embodiments, a suitable delivery vehicle comprises less than 0.01% amphiphilic block copolymers (e.g., poloxamers). In some embodiments, a suitable delivery vehicle contains a residual amount of amphiphilic polymers (e.g., poloxamers). As used herein, a residual amount means a remaining amount after substantially all of the substance (an amphiphilic polymer described herein such as a poloxamer) in a composition is removed. A residual amount may be detectable using a known technique qualitatively or quantitatively. A residual amount may not be detectable using a known technique.

Polymers

In some embodiments, a suitable delivery vehicle is formulated using a polymer as a carrier, alone or in combination with other carriers including various lipids described herein. Thus, in some embodiments, liposomal delivery vehicles, as used herein, also encompass nanoparticles comprising polymers. Suitable polymers may include, for example, polyacrylates, polyalkycyanoacrylates, polylactide, polylactide-polyglycolide copolymers, polycaprolactones, dextran, albumin, gelatin, alginate, collagen, chitosan, cyclodextrins, protamine, PEGylated protamine, PLL, PEGylated PLL and polyethylenimine (PEI). When PEI is present, it may be branched PEI of a molecular weight ranging from 10 to 40 kDa, e.g., 25 kDa branched PEI (Sigma #408727).

According to various embodiments, the selection of cationic lipids, non-cationic lipids, PEG-modified lipids, cholesterol-based lipids, and/or amphiphilic block copolymers which comprise the lipid nanoparticle, as well as the relative molar ratio of such components (lipids) to each other, is based upon the characteristics of the selected lipid(s), the nature of the intended target cells, the characteristics of the nucleic acid to be delivered. Additional considerations include, for example, the saturation of the alkyl chain, as well as the size, charge, pH, pKa, fusogenicity and tolerability of the selected lipid(s). Thus the molar ratios may be adjusted accordingly.

Ratio of Distinct Lipid Components

A suitable liposome for the present invention may include one or more of any of the cationic lipids, non-cationic lipids, cholesterol lipids, PEG-modified lipids, amphiphilic block copolymers and/or polymers described herein at various ratios. In some embodiments, a lipid nanoparticle comprises five and no more than five distinct components of nanoparticle. In some embodiments, a lipid nanoparticle comprises four and no more than four distinct components of nanoparticle. In some embodiments, a lipid nanoparticle comprises three and no more than three distinct components of nanoparticle. As non-limiting examples, a suitable liposome formulation may include a combination selected from cKK-E12 (also known as ML2), DOPE, cholesterol and DMG-PEG2K; C12-200, DOPE, cholesterol and DMG-PEG2K; HGT4003, DOPE, cholesterol and DMG-PEG2K; ICE, DOPE, cholesterol and DMG-PEG2K; or ICE, DOPE, and DMG-PEG2K.

In various embodiments, cationic lipids (e.g., cKK-E12, C12-200, ICE, and/or HGT4003) constitute about 30-60% (e.g., about 30-55%, about 30-50%, about 30-45%, about 30-40%, about 35-50%, about 35-45%, or about 35-40%) of the liposome by molar ratio. In some embodiments, the percentage of cationic lipids (e.g., cKK-E12, C12-200, ICE, and/or HGT4003) is or greater than about 30%, about 35%, about 40%, about 45%, about 50%, about 55%, or about 60% of the liposome by molar ratio.

In some embodiments, the ratio of cationic lipid(s) to non-cationic lipid(s) to cholesterol-based lipid(s) to PEG-modified lipid(s) may be between about 30-60:25-35:20-30:1-15, respectively. In some embodiments, the ratio of cationic lipid(s) to non-cationic lipid(s) to cholesterol-based lipid(s) to PEG-modified lipid(s) is approximately 40:30:20:10, respectively. In some embodiments, the ratio of cationic lipid(s) to non-cationic lipid(s) to cholesterol-based lipid(s) to PEG-modified lipid(s) is approximately 40:30:25:5, respectively. In some embodiments, the ratio of cationic lipid(s) to non-cationic lipid(s) to cholesterol-based lipid(s)

to PEG-modified lipid(s) is approximately 40:32:25:3, respectively. In some embodiments, the ratio of cationic lipid(s) to non-cationic lipid(s) to cholesterol-based lipid(s) to PEG-modified lipid(s) is approximately 50:25:20:5.

In embodiments where a lipid nanoparticle comprises three and no more than three distinct components of lipids, the ratio of total lipid content (i.e., the ratio of lipid component (1):lipid component (2):lipid component (3)) can be represented as x:y:z, wherein $(y+z)=100-x.$ In some embodiments, each of "x," "y," and "z" represents molar percentages of the three distinct components of lipids, and the ratio is a molar ratio.

In some embodiments, each of "x," "y," and "z" represents weight percentages of the three distinct components of lipids, and the ratio is a weight ratio.

In some embodiments, lipid component (1), represented by variable "x," is a sterol-based cationic lipid.

In some embodiments, lipid component (2), represented by variable "y," is a helper lipid.

In some embodiments, lipid component (3), represented by variable "z" is a PEG lipid.

In some embodiments, variable "x," representing the molar percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

In some embodiments, variable "x," representing the molar percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the molar percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "x," representing the weight percentage of lipid component (1) (e.g., a sterol-based cationic lipid), is at least about 10%, about 20%, about 30%, about 40%, about 50%, about 55%, about 60%, about 65%, about 70%, about 75%, about 80%, about 85%, about 90%, or about 95%.

94 In some embodiments, variable "x," representing the weight percentage of lipid component (1) (e.g., a sterol-based cationic lipid), is no more than about 95%, about 90%, about 85%, about 80%, about 75%, about 70%, about 65%, about 60%, about 55%, about 50%, about 40%, about 30%, about 20%, or about 10%. In embodiments, variable "x" is no more than about 65%, about 60%, about 55%, about 50%, about 40%.

In some embodiments, variable "x," representing the weight percentage of lipid component (1) (e.g., a sterol-based cationic lipid), is: at least about 50% but less than about 95%; at least about 50% but less than about 90%; at least about 50% but less than about 85%; at least about 50% but less than about 80%; at least about 50% but less than about 75%; at least about 50% but less than about 70%; at least about 50% but less than about 65%; or at least about 50% but less than about 60%. In embodiments, variable "x" is at least about 50% but less than about 70%; at least about 50% but less than about 65%; or at least about 50% but less than about 60%.

In some embodiments, variable "z," representing the molar percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the molar percentage of lipid component (3) (e.g., a PEG lipid) is about 1%, 2%, 3%, 4%, 5%, 6%, 7%, 8%, 9%, 10%. In embodiments, variable "z," representing the molar percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

In some embodiments, variable "z," representing the weight percentage of lipid component (3) (e.g., a PEG lipid) is no more than about 1%, 2%, 3%, 4%, 5%, 6%, 7%, 8%, 9%, 10%, 15%, 20%, or 25%. In embodiments, variable "z," representing the weight percentage of lipid component (3) (e.g., a PEG lipid) is about 1%, 2%, 3%, 4%, 5%, 6%, 7%, 8%, 9%, 10%. In embodiments, variable "z," representing the weight percentage of lipid component (3) (e.g., a PEG lipid) is about 1% to about 10%, about 2% to about 10%, about 3% to about 10%, about 4% to about 10%, about 1% to about 7.5%, about 2.5% to about 10%, about 2.5% to about 7.5%, about 2.5% to about 5%, about 5% to about 7.5%, or about 5% to about 10%.

For compositions having three and only three distinct lipid components, variables "x," "y," and "z" may be in any combination so long as the total of the three variables sums to 100% of the total lipid content.

mRNA Synthesis mRNAs according to the present invention may be synthesized according to any of a variety of known methods. Various methods are described in published U.S. Application No. US 2018/0258423, and can be used to practice the present invention, all of which are incorporated herein by reference. For example, mRNAs according to the present invention may be synthesized via in vitro transcription (IVT). Briefly, IVT is typically performed with a linear or circular DNA template containing a promoter, a pool of ribonucleotide triphosphates, a buffer system that may include DTT and magnesium ions, and an appropriate RNA polymerase (e.g., T3, T7, or SP6 RNA polymerase), DNAse I, pyrophosphatase, and/or RNAse inhibitor. The exact conditions will vary according to the specific application.

In some embodiments, a suitable mRNA sequence is an mRNA sequence encoding a protein or a peptide. In some embodiments, a suitable mRNA sequence is codon optimized for efficient expression human cells. In some embodiments, a suitable mRNA sequence is naturally-occurring or a wild-type sequence. In some embodiments, a suitable mRNA sequence encodes a protein or a peptide that contains one or mutations in amino acid sequence.

The present invention may be used to deliver mRNAs of a variety of lengths. In some embodiments, the present invention may be used to deliver in vitro synthesized mRNA of or greater than about 0.5 kb, 1 kb, 1.5 kb, 2 kb, 2.5 kb, 3 kb, 3.5 kb, 4 kb, 4.5 kb, 5 kb 6 kb, 7 kb, 8 kb, 9 kb, 10 kb, 11 kb, 12 kb, 13 kb, 14 kb, 15 kb, 20 kb, 30 kb, 40 kb, or 50 kb in length. In some embodiments, the present invention may be used to deliver in vitro synthesized mRNA ranging from about 1-20 kb, about 1-15 kb, about 1-10 kb, about 5-20 kb, about 5-15 kb, about 5-12 kb, about 5-10 kb, about 8-20 kb, or about 8-50 kb in length.

In some embodiments, for the preparation of mRNA according to the invention, a DNA template is transcribed in vitro. A suitable DNA template typically has a promoter, for example a T3, T7 or SP6 promoter, for in vitro transcription, followed by desired nucleotide sequence for desired mRNA and a termination signal.

Nucleotides

Various naturally-occurring or modified nucleosides may be used to produce mRNA according to the present invention. In some embodiments, an mRNA is or comprises naturally-occurring nucleosides (or unmodified nucleotides; e.g., adenosine, guanosine, cytidine, uridine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, pseudouridine, (e.g., N-1-methyl-pseudouridine), 2-thiouridine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

In some embodiments, a suitable mRNA may contain backbone modifications, sugar modifications and/or base modifications. For example, modified nucleotides may include, but not be limited to, modified purines (adenine (A), guanine (G)) or pyrimidines (thymine (T), cytosine (C), uracil (U)), and as modified nucleotides analogues or derivatives of purines and pyrimidines, such as e.g. 1-methyl-adenine, 2-methyl-adenine, 2-methylthio-N-6-isopentenyl-adenine, N6-methyl-adenine, N6-isopentenyl-adenine, 2-thio-cytosine, 3-methyl-cytosine, 4-acetyl-cytosine, 5-methyl-cytosine, 2,6-diaminopurine, 1-methyl-guanine, 2-methyl-guanine, 2,2-dimethyl-guanine, 7-methyl-guanine, inosine, 1-methyl-inosine, pseudouracil (5-uracil), dihydro-uracil, 2-thio-uracil, 4-thio-uracil, 5-carboxymethylaminomethyl-2-thio-uracil, 5-(carboxyhydroxymethyl)-uracil, 5-fluoro-uracil, 5-bromo-uracil, 5-carboxymethyl-aminomethyl-uracil, 5-methyl-2-thio-uracil, 5-methyl-uracil, N-uracil-5-oxyacetic acid methyl ester, 5-methylaminomethyl-uracil, 5-methoxyaminomethyl-2-thio-uracil, 5'-methoxycarbonylmethyl-uracil, 5-methoxy-uracil, uracil-5-oxyacetic acid methyl ester, uracil-5-oxyacetic acid (v), 1-methyl-pseudouracil, queosine, .beta.-D-mannosyl-queosine, wybutoxosine, and phosphoramidates, phosphorothioates, peptide nucleotides, methylphosphonates, 7-deazaguanosine, 5-methylcytosine and inosine. The preparation of such analogues is known to a person skilled in the art e.g., from the U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642, the disclosures of which are incorporated by reference in their entirety.

In some embodiments, the mRNA comprises one or more nonstandard nucleotide residues. The nonstandard nucleotide residues may include, e.g., 5-methyl-cytidine ("5mC"), pseudouridine ("ΨU"), and/or 2-thio-uridine ("2sU"). See, e.g., U.S. Pat. No. 8,278,036 or WO 2011/012316 for a discussion of such residues and their incorporation into mRNA. The mRNA may be RNA, which is defined as RNA in which 25% of U residues are 2-thio-uridine and 25% of C residues are 5-methylcytidine. Teachings for the use of RNA are disclosed US Patent Publication US 2012/0195936 and international publication WO 2011/012316, both of which are hereby incorporated by reference in their entirety. The presence of nonstandard nucleotide residues may render an mRNA more stable and/or less immunogenic than a control mRNA with the same sequence but containing only standard residues. In further embodiments, the mRNA may comprise one or more nonstandard nucleotide residues chosen from isocytosine, pseudoisocytosine, 5-bromouracil, 5-propynyluracil, 6-aminopurine, 2-aminopurine, inosine, diaminopurine and 2-chloro-6-aminopurine cytosine, as well as combinations of these modifications and other nucleobase modifications. Some embodiments may further include additional modifications to the furanose ring or nucleobase. Additional modifications may include, for example, sugar modifications or substitutions (e.g., one or more of a 2'-O-alkyl modification, a locked nucleic acid (LNA)). In some embodiments, the RNAs may be complexed or hybridized with additional polynucleotides and/or peptide polynucleotides (PNA). In some embodiments where the sugar modification is a 2'-O-alkyl modification, such modification may include, but are not limited to a 2'-deoxy-2'-fluoro modification, a 2'-O-methyl modification, a 2'-O-methoxyethyl modification and a 2'-deoxy modification. In some embodiments, any of these modifications may be present in 0-100% of the nucleotides—for example, more than 0%, 1%, 10%, 25%, 50%, 75%, 85%, 90%, 95%, or 100% of the constituent nucleotides individually or in combination.

In some embodiments, mRNAs may contain RNA backbone modifications. Typically, a backbone modification is a modification in which the phosphates of the backbone of the nucleotides contained in the RNA are modified chemically. Exemplary backbone modifications typically include, but are not limited to, modifications from the group consisting of methylphosphonates, methylphosphoramidates, phosphoramidates, phosphorothioates (e.g., cytidine 5'-O-(1-thiophosphate)), boranophosphates, positively charged guanidinium groups etc., which means by replacing the phosphodiester linkage by other anionic, cationic or neutral groups.

In some embodiments, mRNAs may contain sugar modifications. A typical sugar modification is a chemical modification of the sugar of the nucleotides it contains including, but not limited to, sugar modifications chosen from the group consisting of 2'-deoxy-2'-fluoro-oligoribonucleotide (2'-fluoro-2'-deoxycytidine 5'-triphosphate, 2'-fluoro-2'-deoxyuridine 5'-triphosphate), 2'-deoxy-2'-deamine-oligoribonucleotide (2'-amino-2'-deoxycytidine 5'-triphosphate, 2'-amino-2'-deoxyuridine 5'-triphosphate), 2'-O-alkyloligoribonucleotide, 2'-deoxy-2'-C-alkyloligoribonucleotide (2'-O-methylcytidine 5'-triphosphate, 2'-methyluridine 5'-triphosphate), 2'-C-alkyloligoribonucleotide, and isomers thereof (2'-aracytidine 5'-triphosphate, 2'-arauridine 5'-triphosphate), or azidotriphosphates (2'-azido-2'-deoxycytidine 5'-triphosphate, 2'-azido-2'-deoxyuridine 5'-triphosphate).

Post-Synthesis Processing

Typically, a 5' cap and/or a 3' tail may be added after the synthesis. The presence of the cap is important in providing resistance to nucleases found in most eukaryotic cells. The presence of a "tail" serves to protect the mRNA from exonuclease degradation.

A 5' cap is typically added as follows: first, an RNA terminal phosphatase removes one of the terminal phosphate groups from the 5' nucleotide, leaving two terminal phosphates; guanosine triphosphate (GTP) is then added to the terminal phosphates via a guanylyl transferase, producing a 5'5'5 triphosphate linkage; and the 7-nitrogen of guanine is then methylated by a methyltransferase. Examples of cap structures include, but are not limited to, m7G(5')ppp (5'(A, G(5')ppp(5')A and G(5')ppp(5')G. Additional cap structures are described in published U.S. Application No. US 2016/0032356 and published U.S. Application No. US 2018/0125989, which are incorporated herein by reference.

Typically, a tail structure includes a poly(A) and/or poly (C) tail. A poly-A or poly-C tail on the 3' terminus of mRNA typically includes at least 50 adenosine or cytosine nucleotides, at least 150 adenosine or cytosine nucleotides, at least 200 adenosine or cytosine nucleotides, at least 250 adenosine or cytosine nucleotides, at least 300 adenosine or cytosine nucleotides, at least 350 adenosine or cytosine nucleotides, at least 400 adenosine or cytosine nucleotides, at least 450 adenosine or cytosine nucleotides, at least 500 adenosine or cytosine nucleotides, at least 550 adenosine or cytosine nucleotides, at least 600 adenosine or cytosine nucleotides, at least 650 adenosine or cytosine nucleotides, at least 700 adenosine or cytosine nucleotides, at least 750 adenosine or cytosine nucleotides, at least 800 adenosine or cytosine nucleotides, at least 850 adenosine or cytosine nucleotides, at least 900 adenosine or cytosine nucleotides, or at least 1 kb adenosine or cytosine nucleotides, respectively. In some embodiments, a poly A or poly C tail may be about 10 to 800 adenosine or cytosine nucleotides (e.g., about 10 to 200 adenosine or cytosine nucleotides, about 10 to 300 adenosine or cytosine nucleotides, about 10 to 400 adenosine or cytosine nucleotides, about 10 to 500 adenosine or cytosine nucleotides, about 10 to 550 adenosine or cytosine nucleotides, about 10 to 600 adenosine or cytosine nucleotides, about 50 to 600 adenosine or cytosine nucleotides, about 100 to 600 adenosine or cytosine nucleotides, about 150 to 600 adenosine or cytosine nucleotides, about 200 to 600 adenosine or cytosine nucleotides, about 250 to 600 adenosine or cytosine nucleotides, about 300 to 600 adenosine or cytosine nucleotides, about 350 to 600 adenosine or cytosine nucleotides, about 400 to 600 adenosine or cytosine nucleotides, about 450 to 600 adenosine or cytosine nucleotides, about 500 to 600 adenosine or cytosine nucleotides, about 10 to 150 adenosine or cytosine nucleotides, about 10 to 100 adenosine or cytosine nucleotides, about 20 to 70 adenosine or cytosine nucleotides, or about 20 to 60 adenosine or cytosine nucleotides) respectively. In some embodiments, a tail structure includes is a combination of poly (A) and poly (C) tails with various lengths described herein. In some embodiments, a tail structure includes at least 50%, 55%, 65%, 70%, 75%, 80%, 85%, 90%, 92%, 94%, 95%, 96%, 97%, 98%, or 99% adenosine nucleotides. In some embodiments, a tail structure includes at least 50%, 55%, 65%, 70%, 75%, 80%, 85%, 90%, 92%, 94%, 95%, 96%, 97%, 98%, or 99% cytosine nucleotides.

As described herein, the addition of the 5' cap and/or the 3' tail facilitates the detection of abortive transcripts generated during in vitro synthesis because without capping and/or tailing, the size of those prematurely aborted mRNA transcripts can be too small to be detected. Thus, in some embodiments, the 5' cap and/or the 3' tail are added to the synthesized mRNA before the mRNA is tested for purity (e.g., the level of abortive transcripts present in the mRNA). In some embodiments, the 5' cap and/or the 3' tail are added to the synthesized mRNA before the mRNA is purified as described herein. In other embodiments, the 5' cap and/or the 3' tail are added to the synthesized mRNA after the mRNA is purified as described herein.

mRNA synthesized according to the present invention may be used without further purification. In particular, mRNA synthesized according to the present invention may be used without a step of removing shortmers. In some embodiments, mRNA synthesized according to the present invention may be further purified. Various methods may be used to purify mRNA synthesized according to the present invention. For example, purification of mRNA can be performed using centrifugation, filtration and/or chromatographic methods. In some embodiments, the synthesized mRNA is purified by ethanol precipitation or filtration or chromatography, or gel purification or any other suitable means. In some embodiments, the mRNA is purified by HPLC. In some embodiments, the mRNA is extracted in a standard phenol:chloroform:isoamyl alcohol solution, well known to one of skill in the art. In some embodiments, the mRNA is purified using Tangential Flow Filtration. Suitable purification methods include those described in published U.S. Application No. US 2016/0040154, published U.S. Application No. US 2015/0376220, published U.S. Application No. US 2018/0251755, published U.S. Application No. US 2018/0251754, U.S. Provisional Application No. 62/757,612 filed on Nov. 8, 2018, and U.S. Provisional Application No. 62/891,781 filed on Aug. 26, 2019, all of which are incorporated by reference herein and may be used to practice the present invention.

In some embodiments, the mRNA is purified before capping and tailing. In some embodiments, the mRNA is purified after capping and tailing. In some embodiments, the mRNA is purified both before and after capping and tailing.

In some embodiments, the mRNA is purified either before or after or both before and after capping and tailing, by centrifugation.

In some embodiments, the mRNA is purified either before or after or both before and after capping and tailing, by filtration.

In some embodiments, the mRNA is purified either before or after or both before and after capping and tailing, by Tangential Flow Filtration (TFF).

In some embodiments, the mRNA is purified either before or after or both before and after capping and tailing by chromatography.

Characterization of Purified mRNA

The mRNA composition described herein is substantially free of contaminants comprising short abortive RNA species, long abortive RNA species, double-stranded RNA (dsRNA), residual plasmid DNA, residual in vitro transcription enzymes, residual solvent and/or residual salt.

The mRNA composition described herein has a purity of about between 60% and about 100%. Accordingly, in some embodiments, the purified mRNA has a purity of about 60%. In some embodiments, the purified mRNA has a purity of about 65%. In some embodiments, the purified mRNA has a purity of about 70%. In some embodiments, the purified mRNA has a purity of about 75%. In some embodiments, the purified mRNA has a purity of about 80%. In some embodiments, the purified mRNA has a purity of about 85%. In some embodiments, the purified mRNA has a purity of about 90%. In some embodiments, the purified mRNA has a purity of about 91%. In some embodiments, the purified mRNA has a purity of about 92%. In some embodiments, the purified mRNA has a purity of about 93%. In some embodiments, the purified mRNA has a purity of about 94%. In some embodiments, the purified mRNA has a purity of about 95%. In some embodiments, the purified mRNA has a purity of about 96%. In some embodiments, the purified mRNA has a purity of about 97%. In some embodiments, the purified mRNA has a purity of about 98%. In some embodiments, the purified mRNA has a purity of about 99%. In some embodiments, the purified mRNA has a purity of about 100%.

In some embodiments, the mRNA composition described herein has less than 10%, less than 9%, less than 8%, less than 7%, less than 6%, less than 5%, less than 4%, less than 3%, less than 2%, less than 1%, less than 0.5%, and/or less than 0.1% impurities other than full-length mRNA. The impurities include IVT contaminants, e.g., proteins, enzymes, DNA templates, free nucleotides, residual solvent, residual salt, double-stranded RNA (dsRNA), prematurely aborted RNA sequences ("shortmers" or "short abortive RNA species"), and/or long abortive RNA species. In some embodiments, the purified mRNA is substantially free of process enzymes.

In some embodiments, the residual plasmid DNA in the purified mRNA of the present invention is less than about 1 pg/mg, less than about 2 pg/mg, less than about 3 pg/mg, less than about 4 pg/mg, less than about 5 pg/mg, less than about 6 pg/mg, less than about 7 pg/mg, less than about 8 pg/mg, less than about 9 pg/mg, less than about 10 pg/mg, less than about 11 pg/mg, or less than about 12 pg/mg. Accordingly, the residual plasmid DNA in the purified mRNA is less than about 1 pg/mg. In some embodiments, the residual plasmid DNA in the purified mRNA is less than about 2 pg/mg. In some embodiments, the residual plasmid DNA in the purified mRNA is less than about 3 pg/mg. In some embodiments, the residual plasmid DNA in the purified mRNA is less than about 4 pg/mg. In some embodiments, the residual plasmid DNA in the purified mRNA is less than about 5 pg/mg. In some embodiments, the residual plasmid DNA in the purified mRNA is less than about 6 pg/mg. In some embodiments, the residual plasmid DNA in the purified mRNA is less than about 7 pg/mg. In some embodiments, the residual plasmid DNA in the purified mRNA is less than about 8 pg/mg. In some embodiments, the residual plasmid DNA in the purified mRNA is less than about 9 pg/mg. In some embodiments, the residual plasmid DNA in the purified mRNA is less than about 10 pg/mg. In some embodiments, the residual plasmid DNA in the purified mRNA is less than about 11 pg/mg. In some embodiments, the residual plasmid DNA in the purified mRNA is less than about 12 pg/mg.

In some embodiments, a method according to the invention removes more than about 90%, 95%, 96%, 97%, 98%, 99% or substantially all prematurely aborted RNA sequences (also known as "shortmers"). In some embodiments, mRNA composition is substantially free of prematurely aborted RNA sequences. In some embodiments, mRNA composition contains less than about 5% (e.g., less than about 4%, 3%, 2%, or 1%) of prematurely aborted RNA sequences. In some embodiments, mRNA composition contains less than about 1% (e.g., less than about 0.9%, 0.8%, 0.7%, 0.6%, 0.5%, 0.4%, 0.3%, 0.2%, or 0.1%) of prematurely aborted RNA sequences. In some embodiments, mRNA composition undetectable prematurely aborted RNA sequences as determined by, e.g., high-performance liquid chromatography (HPLC) (e.g., shoulders or separate peaks), ethidium bromide, Coomassie staining, capillary electrophoresis or Glyoxal gel electrophoresis (e.g., presence of separate lower band). As used herein, the term "shortmers", "short abortive RNA species", "prematurely aborted RNA sequences" or "long abortive RNA species" refers to any transcripts that are less than full-length. In some embodiments, "shortmers", "short abortive RNA species", or "prematurely aborted RNA sequences" are less than 100 nucleotides in length, less than 90, less than 80, less than 70, less than 60, less than 50, less than 40, less than 30, less than 20, or less than 10 nucleotides in length. In some embodiments, shortmers are detected or quantified after adding a 5'-cap, and/or a 3'-poly A tail. In some embodiments, prematurely aborted RNA transcripts comprise less than 15 bases (e.g., less than 14, 13, 12, 11, 10, 9, 8, 7, 6, 5, 4, or 3 bases). In some embodiments, the prematurely aborted RNA transcripts contain about 8-15, 8-14, 8-13, 8-12, 8-11, or 8-10 bases.

In some embodiments, a purified mRNA of the present invention is substantially free of enzyme reagents used in in vitro synthesis including, but not limited to, T7 RNA polymerase, DNAse I, pyrophosphatase, and/or RNAse inhibitor. In some embodiments, a purified mRNA according to the present invention contains less than about 5% (e.g., less than about 4%, 3%, 2%, or 1%) of enzyme reagents used in in vitro synthesis including. In some embodiments, a purified mRNA contains less than about 1% (e.g., less than about 0.9%, 0.8%, 0.7%, 0.6%, 0.5%, 0.4%, 0.3%, 0.2%, or 0.1%) of enzyme reagents used in in vitro synthesis including. In some embodiments, a purified mRNA contains undetectable enzyme reagents used in in vitro synthesis including as determined by, e.g., silver stain, gel electrophoresis, high-performance liquid chromatography (HPLC), ultra-performance liquid chromatography (UPLC), and/or capillary electrophoresis, ethidium bromide and/or Coomassie staining.

In various embodiments, a purified mRNA of the present invention maintains high degree of integrity. As used herein, the term "mRNA integrity" generally refers to the quality of mRNA after purification. mRNA integrity may be determined using methods well known in the art, for example, by RNA agarose gel electrophoresis. In some embodiments, mRNA integrity may be determined by banding patterns of RNA agarose gel electrophoresis. In some embodiments, a purified mRNA of the present invention shows little or no banding compared to reference band of RNA agarose gel electrophoresis. In some embodiments, a purified mRNA of the present invention has an integrity greater than about 95% (e.g., greater than about 96%, 97%, 98%, 99% or more). In some embodiments, a purified mRNA of the present invention has an integrity greater than 98%. In some embodiments, a purified mRNA of the present invention has an integrity greater than 99%. In some embodiments, a purified mRNA of the present invention has an integrity of approximately 100%.

In some embodiments, the purified mRNA is assessed for one or more of the following characteristics: appearance, identity, quantity, concentration, presence of impurities, microbiological assessment, pH level and activity. In some embodiments, acceptable appearance includes a clear, colorless solution, essentially free of visible particulates. In some embodiments, the identity of the mRNA is assessed by sequencing methods. In some embodiments, the concentration is assessed by a suitable method, such as UV spectrophotometry. In some embodiments, a suitable concentration is between about 90% and 110% nominal (0.9-1.1 mg/mL).

In some embodiments, assessing the purity of the mRNA includes assessment of mRNA integrity, assessment of residual plasmid DNA, and assessment of residual solvent. In some embodiments, acceptable levels of mRNA integrity are assessed by agarose gel electrophoresis. The gels are analyzed to determine whether the banding pattern and apparent nucleotide length is consistent with an analytical reference standard. Additional methods to assess RNA integrity include, for example, assessment of the purified mRNA using capillary gel electrophoresis (CGE). In some embodiments, acceptable purity of the purified mRNA as determined by CGE is that the purified mRNA composition has no greater than about 55% long abortive/degraded species. In some embodiments, residual plasmid DNA is assessed by methods in the art, for example by the use of qPCR. In some embodiments, less than 10 pg/mg (e.g., less than 10 pg/mg, less than 9 pg/mg, less than 8 pg/mg, less than 7 pg/mg, less than 6 pg/mg, less than 5 pg/mg, less than 4 pg/mg, less than 3 pg/mg, less than 2 pg/mg, or less than 1 pg/mg) is an acceptable level of residual plasmid DNA. In some embodiments, acceptable residual solvent levels are not more than 10,000 ppm, 9,000 ppm, 8,000 ppm, 7,000 ppm, 6,000 ppm, 5,000 ppm, 4,000 ppm, 3,000 ppm, 2,000 ppm, 1,000 ppm. Accordingly, in some embodiments, acceptable residual solvent levels are not more than 10,000 ppm. In some embodiments, acceptable residual solvent levels are not more than 9,000 ppm. In some embodiments, acceptable residual solvent levels are not more than 8,000 ppm. In some embodiments, acceptable residual solvent levels are not more than 7,000 ppm. In some embodiments, acceptable residual solvent levels are not more than 6,000 ppm. In some embodiments, acceptable residual solvent levels are not more than 5,000 ppm. In some embodiments, acceptable residual solvent levels are not more than 4,000 ppm. In some embodiments, acceptable residual solvent levels are not more than 3,000 ppm. In some embodiments, acceptable residual solvent levels are not more than 2,000 ppm. In some embodiments, acceptable residual solvent levels are not more than 1,000 ppm.

In some embodiments, microbiological tests are performed on the purified mRNA, which include, for example, assessment of bacterial endotoxins. In some embodiments, bacterial endotoxins are <0.5 EU/mL, <0.4 EU/mL, <0.3 EU/mL, <0.2 EU/mL or <0.1 EU/mL. Accordingly, in some embodiments, bacterial endotoxins in the purified mRNA are <0.5 EU/mL. In some embodiments, bacterial endotoxins in the purified mRNA are <0.4 EU/mL. In some embodiments, bacterial endotoxins in the purified mRNA are <0.3 EU/mL. In some embodiments, bacterial endotoxins in the purified mRNA are <0.2 EU/mL. In some embodiments, bacterial endotoxins in the purified mRNA are <0.2 EU/mL. In some embodiments, bacterial endotoxins in the purified mRNA are <0.1 EU/mL. In some embodiments, the purified mRNA has not more than 1 CFU/10 mL, 1 CFU/25 mL, 1 CFU/50 mL, 1 CFU/75 mL, or not more than 1 CFU/100 mL. Accordingly, in some embodiments, the purified mRNA has not more than 1 CFU/10 mL. In some embodiments, the purified mRNA has not more than 1 CFU/25 mL. In some embodiments, the purified mRNA has not more than 1 CFU/50 mL. In some embodiments, the purified mRNA has not more than 1 CFR/75 mL. In some embodiments, the purified mRNA has 1 CFU/100 mL.

In some embodiments, the pH of the purified mRNA is assessed. In some embodiments, acceptable pH of the purified mRNA is between 5 and 8. Accordingly, in some embodiments, the purified mRNA has a pH of about 5. In some embodiments, the purified mRNA has a pH of about 6. In some embodiments, the purified mRNA has a pH of about 7. In some embodiments, the purified mRNA has a pH of about 7. In some embodiments, the purified mRNA has a pH of about 8.

In some embodiments, the translational fidelity of the purified mRNA is assessed. The translational fidelity can be assessed by various methods and include, for example, transfection and Western blot analysis. Acceptable characteristics of the purified mRNA includes banding pattern on a Western blot that migrates at a similar molecular weight as a reference standard.

In some embodiments, the purified mRNA is assessed for conductance. In some embodiments, acceptable characteristics of the purified mRNA include a conductance of between about 50% and 150% of a reference standard.

The purified mRNA is also assessed for Cap percentage and for PolyA tail length. In some embodiments, an acceptable Cap percentage includes Cap1, % Area: NLT90. In some embodiments, an acceptable PolyA tail length is about 100-1500 nucleotides (e.g., 100, 150, 200, 250, 300, 350, 400, 450, 500, 550, 600, 650, 700, 750, 800, 850, 900, 950, and 1000, 1100, 1200, 1300, 1400, or 1500 nucleotides).

In some embodiments, the purified mRNA is also assessed for any residual PEG. In some embodiments, the purified mRNA has less than between 10 ng PEG/mg of purified mRNA and 1000 ng PEG/mg of mRNA. Accordingly, in some embodiments, the purified mRNA has less than about 10 ng PEG/mg of purified mRNA. In some embodiments, the purified mRNA has less than about 100 ng PEG/mg of purified mRNA. In some embodiments, the purified mRNA has less than about 250 ng PEG/mg of purified mRNA. In some embodiments, the purified mRNA has less than about 500 ng PEG/mg of purified mRNA. In some embodiments, the purified mRNA has less than about 750 ng PEG/mg of purified mRNA. In some embodiments, the purified mRNA has less than about 1000 ng PEG/mg of purified mRNA.

Various methods of detecting and quantifying mRNA purity are known in the art. For example, such methods include, blotting, capillary electrophoresis, chromatography, fluorescence, gel electrophoresis, HPLC, silver stain, spectroscopy, ultraviolet (UV), or UPLC, or a combination thereof. In some embodiments, mRNA is first denatured by a Glyoxal dye before gel electrophoresis ("Glyoxal gel electrophoresis"). In some embodiments, synthesized mRNA is characterized before capping or tailing. In some embodiments, synthesized mRNA is characterized after capping and tailing.

Therapeutic Use of Compositions

To facilitate expression of mRNA in vivo, delivery vehicles such as liposomes can be formulated in combination with one or more additional nucleic acids, carriers, targeting ligands or stabilizing reagents, or in pharmacological compositions where it is mixed with suitable excipients. Techniques for formulation and administration of drugs may be found in "Remington's Pharmaceutical Sciences," Mack Publishing Co., Easton, Pa., latest edition.

In some embodiments, a composition comprises mRNA encapsulated or complexed with a delivery vehicle. In some embodiments, the delivery vehicle is selected from the group consisting of liposomes, lipid nanoparticles, solid-lipid nanoparticles, polymers, viruses, sol-gels, and nanogels.

Provided mRNA-loaded nanoparticles, and compositions containing the same, may be administered and dosed in accordance with current medical practice, taking into account the clinical condition of the subject, the site and method of administration, the scheduling of administration, the subject's age, sex, body weight and other factors relevant to clinicians of ordinary skill in the art. The "effective amount" for the purposes herein may be determined by such relevant considerations as are known to those of ordinary skill in experimental clinical research, pharmacological, clinical, and medical arts. In some embodiments, the amount administered is effective to achieve at least some stabilization, improvement or elimination of symptoms and other indicators as are selected as appropriate measures of disease progress, regression or improvement by those of skill in the art. For example, a suitable amount and dosing regimen is one that causes at least transient protein (e.g., enzyme) production.

The present invention provides methods of delivering mRNA for in vivo protein production, comprising administering mRNA to a subject in need of delivery. In some embodiments, mRNA is administered via a route of delivery selected from the group consisting of intravenous delivery, subcutaneous delivery, oral delivery, subdermal delivery, ocular delivery, intratracheal injection pulmonary delivery (e.g. nebulization), intramuscular delivery, intrathecal delivery, or intraarticular delivery.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal. In some embodiments, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Additional teaching of pulmonary delivery and nebulization are described in published U.S. Application No. US 2018/0125989 and published U.S. Application No. US 2018/0333457, each of which is incorporated by reference in its entirety.

Alternatively or additionally, mRNA-loaded nanoparticles and compositions of the invention may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present invention can be inhaled (for nasal, tracheal, or bronchial delivery); compositions of the present invention can be injected into the site of injury, disease manifestation, or pain, for example; compositions can be provided in lozenges for oral, tracheal, or esophageal application; can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Provided methods of the present invention contemplate single as well as multiple administrations of a therapeutically effective amount of the therapeutic agents (e.g., mRNA) described herein. Therapeutic agents can be administered at regular intervals, depending on the nature, severity and extent of the subject's condition. In some embodiments, a therapeutically effective amount of the therapeutic agents (e.g., mRNA) of the present invention may be administered intrathecally periodically at regular intervals (e.g., once every year, once every six-months, once every five-months, once every three-months, bimonthly (once every two-months), monthly (once every month), biweekly (once every two-weeks), twice a month, once every 30-days, once every 28-days, once every 14-days, once every 10-days, once every 7-days, weekly, twice a week, daily, or continuously).

In some embodiments, provided liposomes and/or compositions are formulated such that they are suitable for extended-release of the mRNA contained therein. Such extended-release compositions may be conveniently administered to a subject at extended dosing intervals. For example, in one embodiment, the compositions of the present invention are administered to a subject twice a day, daily, or every other day. In a preferred embodiment, the compositions of the present invention are administered to a subject twice a week, once a week, once every 7-days, once every 10-days, once every 14-days, once every 28-days, once every 30-days, once every two-weeks, once every three-weeks, or more-preferably once every four-weeks, once-a-month, twice-a-month, once every six-weeks, once every eight-weeks, once every other month, once every three-months, once every four-months, once every six-months, once every eight-months, once every nine-months, or annually. Also contemplated are compositions and liposomes that are formulated for depot administration (e.g., intramuscularly, subcutaneously, intravitreally) to either deliver or release therapeutic agent (e.g., mRNA) over extended periods of time. Preferably, the extended-release means employed are combined with modifications made to the mRNA to enhance stability.

As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating a disease or disorder). For example, a therapeutically effective amount may be an amount sufficient to achieve a desired therapeutic and/or prophylactic effect. Generally, the amount of a therapeutic agent (e.g., mRNA) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

A therapeutically effective amount is commonly administered in a dosing regimen that may comprise multiple unit doses. For any particular therapeutic protein, a therapeutically effective amount (and/or an appropriate unit dose within an effective dosing regimen) may vary, for example, depending on route of administration, on combination with other pharmaceutical agents. Also, the specific therapeutically effective amount (and/or unit dose) for any particular patient may depend upon a variety of factors including the disorder being treated and the severity of the disorder; the activity of the specific pharmaceutical agent employed; the specific composition employed; the age, body weight, general health, sex and diet of the patient; the time of administration, route of administration, and/or rate of excretion or metabolism of the specific protein employed; the duration of the treatment; and like factors as is well known in the medical arts.

In some embodiments, the therapeutically effective dose ranges from about 0.005 mg/kg body weight to 500 mg/kg body weight, e.g., from about 0.005 mg/kg body weight to 400 mg/kg body weight, from about 0.005 mg/kg body weight to 300 mg/kg body weight, from about 0.005 mg/kg body weight to 200 mg/kg body weight, from about 0.005 mg/kg body weight to 100 mg/kg body weight, from about 0.005 mg/kg body weight to 90 mg/kg body weight, from about 0.005 mg/kg body weight to 80 mg/kg body weight, from about 0.005 mg/kg body weight to 70 mg/kg body weight, from about 0.005 mg/kg body weight to 60 mg/kg body weight, from about 0.005 mg/kg body weight to 50 mg/kg body weight, from about 0.005 mg/kg body weight to 40 mg/kg body weight, from about 0.005 mg/kg body weight to 30 mg/kg body weight, from about 0.005 mg/kg body weight to 25 mg/kg body weight, from about 0.005 mg/kg body weight to 20 mg/kg body weight, from about 0.005 mg/kg body weight to 15 mg/kg body weight, from about 0.005 mg/kg body weight to 10 mg/kg body weight.

In some embodiments, the therapeutically effective dose is greater than about 0.1 mg/kg body weight, greater than about 0.5 mg/kg body weight, greater than about 1.0 mg/kg body weight, greater than about 3 mg/kg body weight, greater than about 5 mg/kg body weight, greater than about 10 mg/kg body weight, greater than about 15 mg/kg body weight, greater than about 20 mg/kg body weight, greater than about 30 mg/kg body weight, greater than about 40 mg/kg body weight, greater than about 50 mg/kg body weight, greater than about 60 mg/kg body weight, greater than about 70 mg/kg body weight, greater than about 80 mg/kg body weight, greater than about 90 mg/kg body weight, greater than about 100 mg/kg body weight, greater than about 150 mg/kg body weight, greater than about 200 mg/kg body weight, greater than about 250 mg/kg body weight, greater than about 300 mg/kg body weight, greater than about 350 mg/kg body weight, greater than about 400 mg/kg body weight, greater than about 450 mg/kg body weight, greater than about 500 mg/kg body weight. In a particular embodiment, the therapeutically effective dose is 1.0 mg/kg. In some embodiments, the therapeutically effective dose of 1.0 mg/kg is administered intramuscularly or intravenously.

Also contemplated herein are lyophilized pharmaceutical compositions comprising one or more of the liposomes disclosed herein and related methods for the use of such compositions as disclosed for example, in U.S. Provisional Application No. 61/494,882, filed Jun. 8, 2011, the teachings of which are incorporated herein by reference in their entirety. For example, lyophilized pharmaceutical compositions according to the invention may be reconstituted prior to administration or can be reconstituted in vivo. For example, a lyophilized pharmaceutical composition can be formulated in an appropriate dosage form (e.g., an intradermal dosage form such as a disk, rod or membrane) and administered such that the dosage form is rehydrated over time in vivo by the individual's bodily fluids.

Provided liposomes and compositions may be administered to any desired tissue. In some embodiments, the mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

In some embodiments, administering the provided composition results in an increased mRNA expression level in a biological sample from a subject as compared to a baseline expression level before treatment. Typically, the baseline level is measured immediately before treatment. Biological samples include, for example, whole blood, serum, plasma, urine and tissue samples (e.g., muscle, liver, skin fibroblasts). In some embodiments, administering the provided composition results in an increased mRNA expression level by at least about 10%, 20%, 30%, 40%, 50%, 60%, 70%, 80%, 90%, or 95% as compared to the baseline level immediately before treatment. In some embodiments, administering the provided composition results in an increased mRNA expression level as compared to an mRNA expression level in subjects who are not treated According to various embodiments, the timing of expression of delivered mRNA can be tuned to suit a particular medical need. In some embodiments, the expression of the protein encoded by delivered mRNA is detectable 1, 2, 3, 6, 12, 24, 48, 72, and/or 96 hours after administration of provided liposomes and/or compositions. In some embodiments, the expression of the protein encoded by delivered mRNA is detectable one-week, two-weeks, and/or one-month after administration.

The present invention also provides delivering a composition having mRNA molecules encoding a peptide or polypeptide of interest for use in the treatment of a subject, e.g., a human subject or a cell of a human subject or a cell that is treated and delivered to a human subject.

EXAMPLES

While certain compounds, compositions and methods of the present invention have been described with specificity in accordance with certain embodiments, the following examples serve only to illustrate the invention and are not intended to limit the same. While certain compounds, compositions and methods of the present invention have been described with specificity in accordance with certain embodiments, the following examples serve only to illustrate the invention and are not intended to limit the same.

Example 1 Lipid Nanoparticle Formulation Process for Composition #1

This example illustrates an exemplary lipid nanoparticle formulation process for encapsulating mRNA. The process of forming mRNA-loaded lipid nanoparticle composition of high potency and tolerability is graphically represented in FIG. 1, referred to as Process C. Process C comprises a step of encapsulating mRNA by mixing mRNA with preformed empty lipid nanoparticles in Step (a) (also referred to as "Process B" hereinafter); and combining the mRNA-LNP of Step (a) with preformed (empty) LNPs in Step (b). Therefore, completion of both Process B (step (a)) and step (b) results in Process C.

Generation of Lipid Nanoparticles by Process C

Step (a). Preparation of mRNA Lipid Nanoparticles: This step involves the process of encapsulating messenger RNA (mRNA) by mixing preformed lipid nanoparticles with mRNA. Step (a) of Process C is also known as Process B, which refers to a process of encapsulating mRNA by mixing pre-formed lipid nanoparticles with mRNA, as described in US 2018/0153822, which is incorporated by reference in its entirety. Different conditions, such as varying temperatures (i.e., heating or not heating the mixture), buffers, and concentrations, may be employed in Process B. An aliquot from the resulting suspension of preformed empty lipid nanoparticles from step (a) was mixed with mRNA using a pump system. For certain cationic lipids, heating the solution post-mixing resulted in a higher percentage of lipid nanoparticles containing mRNA and a higher total yield of mRNA. The resulting nanoparticle suspension was filtered using 10% trehalose, concentrated and stored at −80° C. In this example, mRNA encoding EPO was encapsulated into lipid nanoparticles comprising ML2, DOPE, Cholesterol, and DMG-PEG2K.

Step (b). Preparation of the mRNA-LNP composition: In this step, the mRNA-LNPs from step (a) (Process B products) are then mixed with additional empty lipid nanoparticles from a stock prepared prior to step (a). In this example, three different empty lipid nanoparticles were prepared: (1) ML2, DOPE, Cholesterol, and DMG-PEG2K; (2) CCBene, DOPE, Cholesterol, and DMG-PEG2K; (3) DPPC, DOPE, Cholesterol, and DMG-PEG2K. The size and PDI of empty LNPs are shown in Table 1. The resulting composition comprises mRNA-LNPs and empty LNPs, as depicted in FIG. 1 and their characteristics are shown in Table 2.

TABLE 1

Characteristics of Empty Lipid Nanoparticles (LNPs)

| LNP | Size (nm) | PDI |
|---|---|---|
| Empty ML2 | 71 | 0.12 |
| Empty CCBene | 69 | 0.13 |
| Empty DPPC | 97 | 0.19 |

TABLE 2

Characteristics of mRNA-LNPs prepared by Process C

| LNP | Size (nm) | PDI | % encapsulation |
|---|---|---|---|
| ML2-Process B | 93 | 0.09 | 92.55 |
| ML2-Process C with empty ML2 LNPs | 86 | 0.13 | 88.02 |
| ML2-Process C with empty CCBene LNPs | 89 | 0.11 | 86.42 |
| ML2-Process C with empty DPPC LNPs | 98 | 0.11 | 86.92 |

Example 2. In Vivo Expression of the mRNA-LNP

This example illustrates that mRNA delivered by lipid nanoparticles produced by the process of the invention, Process C, had unexpectedly high in vivo expression than mRNA-LNPs formed by Process B.

Figure 2:
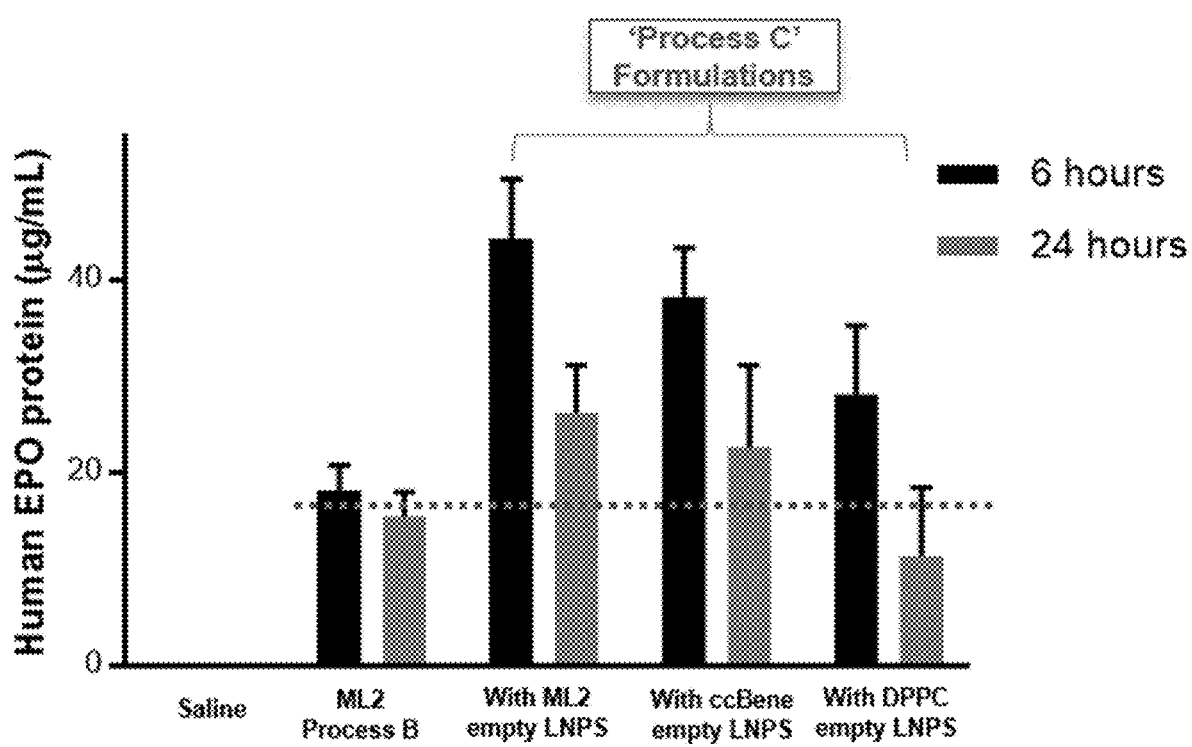
FIG. 2 is an exemplary graph that compares in vivo potency of mRNA-LNPs prepared by Process B and Process C. Human EPO expression in serum of mice was measured at 6 and 24 hours after the administration of mRNA-LNPs prepared by the Process B or Process C. For mRNA-LNPs prepared by Process C, the lipid component of empty LNPs is indicated.

In this example, mice were administered a single intravenous dose of human EPO mRNA encapsulated in lipid nanoparticles prepared by Process B or Process C in Example 1. Serum was collected from these mice at 6 hours and 24 hours after the administration and analyzed for human EPO protein levels. As shown in FIG. 2, mRNA-LNPs prepared by Process C produced higher EPO expression at both 6 and 24 hours compared to that produced by Process B. Additionally, these findings were consistent across different LNPs, irrespective of whether the empty LNP comprises cationic lipid ML2, or CCBene, or whether the empty LNPs comprise neutral lipid DPPC (FIG. 2).

More surprisingly, the formulation comprising neutral DPPC (without cationic lipids) which are known to result in very weak delivery and expression in vivo, showed greater level of EPO expression than the formulation in Process B. These data indicate higher expression of the mRNA-encoded protein in vivo when the mRNA-LNP compositions were formed by Process C of the present invention. Additionally it shows that a variety of empty lipid nanoparticles, with either the same of different lipid constituents, can result in enhanced expression of mRNA-encoded protein.

Example 3. Tolerability of the mRNA-LNP

This example shows that mRNA-LNPs made according to the present invention provides an increased in vivo tolerability. Liver aspartate transaminase (AST) and aminotransferase (ALT) levels are typically measured as determinants for tolerability in response to a drug; the higher the expression is in the liver, the lower the level of tolerability.

Figure 3:
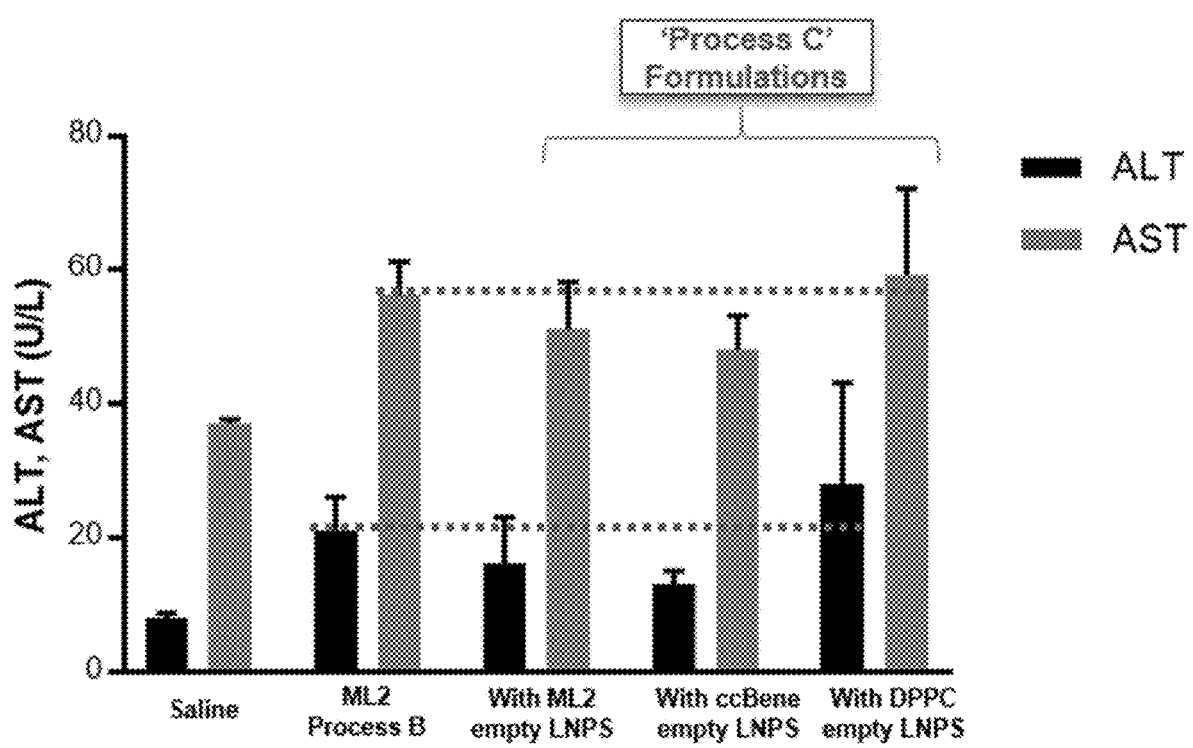
FIG. 3 is an exemplary graph that compares the tolerability of mRNA-LNPs prepared by Process B and Process C. The level of liver enzymes, AST and ALT, were measured at 24 hours after the administration of mRNA-LNPs prepared by the Process B or Process C. For mRNA-LNPs prepared by Process C, the lipid component of empty LNPs is indicated.

In this example, mice were administered a single intravenous dose of hEPO mRNA encapsulated in lipid nanoparticles prepared by Process B or C, as described in Example 2. Mice were sacrificed at 24 hours post-administration and levels of liver enzymes AST and ALT were determined. As shown in FIG. 3, AST levels of mice administered with mRNA-LNPs prepared by Process C were lower than that of mice administered with mRNA-LNPs prepared by Process B, when the empty LNPs of Process C comprise cationic lipids. The AST level of mice administered with mRNA-LNPs with DPPC empty LNPs prepared by Process C was comparable to that of mice administered with mRNA-LNPs prepared by Process B. The same trend was observed for the ALT levels. Of note, LNPs prepared by Process C have higher lipid:mRNA content (i.e. N/P ratio) than LNPs prepared by Process B. These data indicate that the mRNA-LNPs prepared by Process C are better or comparable in terms of tolerability to that of Process B despite the higher lipid content, while resulting in higher expression of the mRNA-encoded protein.

Example 4. Comparison of mRNA-LNP Formed by Process B and Process C by mRNA or Lipid Content In this example, the doses of mRNA-LNPs administered to mice were adjusted such that equal amounts of total lipid or mRNA was administered for comparison.

Three groups of mice were administered an intravenous dose of hEPO mRNA encapsulated in lipid nanoparticles prepared by either step (a) alone (Process B) or upon completion of step (b) (Process C). The composition of mRNA-LNPs are as indicated in Table 3. As Process C comprises a step of adding empty LNPs, mRNA-LNPs prepared by Process C comprise higher lipid content (Group 1 vs 2 in Table 3), even though they contain the same amount of mRNA.

TABLE 3

Characteristics of hEPO-mRNA LNPs

| Group | Process | LNP composition (Molar ratio) | Lipid/mRNA ratio (mg/mg) |
|---|---|---|---|
| 1 | Process C | DMG-PEG2000:ML2:Cholesterol:DOPE (5:40:25:30) | 25.42 |
| 2 | Process B | | 12.71 |
| 3 | Process B | | 25.42 |

Figure 4A:
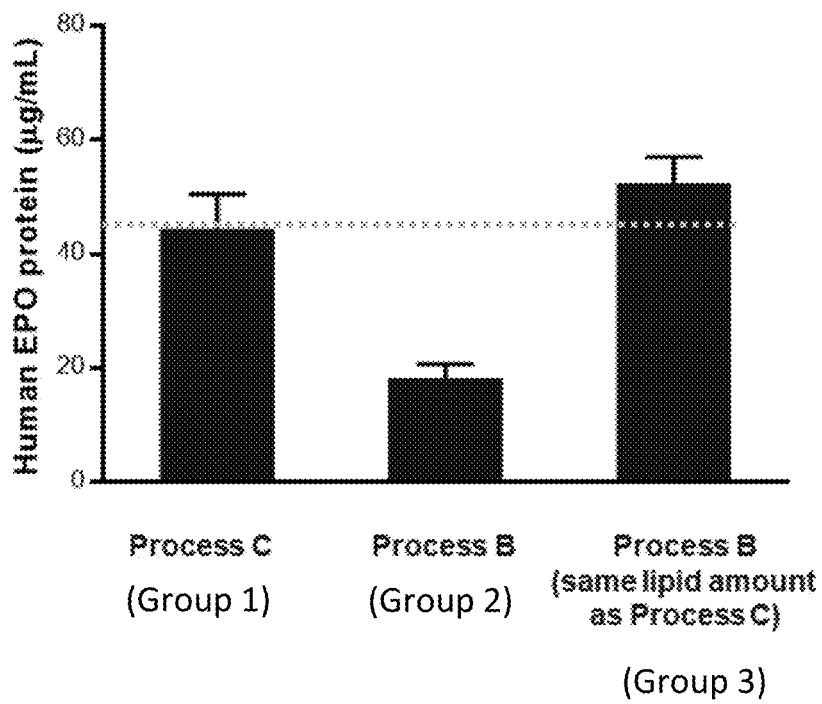
FIG. 4A is an exemplary graph that compares in vivo potency of mRNA-LNPs prepared by Process B and Process C. Human EPO expression in serum of mice was measured at 24 hours after the administration of mRNA-LNPs. To compare potency of mRNA-LNPs prepared by Process B versus Process C, the amount of mRNA-LNP administered to mice was adjusted by the amount of mRNA or lipids.

To examine whether the higher lipid content has an impact in vivo, Group 1 mice received hEPO mRNA-LNPs formed by Process C, and Group 2 mice received hEPO mRNA-LNPs prepared by Process B; equal amount of mRNA was administered to each group. Group 3 mice received hEPO mRNA-LNPs prepared by Process B, where the mRNA-LNP was adjusted such that Group 1 and Group 3 mice received equal amounts of the total lipid in the mRNA-LNPs prepared by Process C and Process B, respectively. Therefore, Group 3 mice received higher dose of mRNA as compared to Group 1. The expression levels of human EPO in the serum were measured at 24 hours post administration. As shown in FIG. 4A, Group 1 mice exhibited higher human EPO levels serum compared to Group 2 mice, in agreement with results shown in the preceding example. This meant that even though Group 1 and Group 2 mice received the same amount of mRNA, the mRNA-LNP prepared by Process C was more potent than that by Process B for in vivo expression of the mRNA. On the other hand, Group 3 mice showed comparable, even marginally higher expression of hEPO protein as compared to Group 1 mice. As shown in Table 3, Group 3 received higher amount of mRNA as compared to Group 1.

Figure 4B:
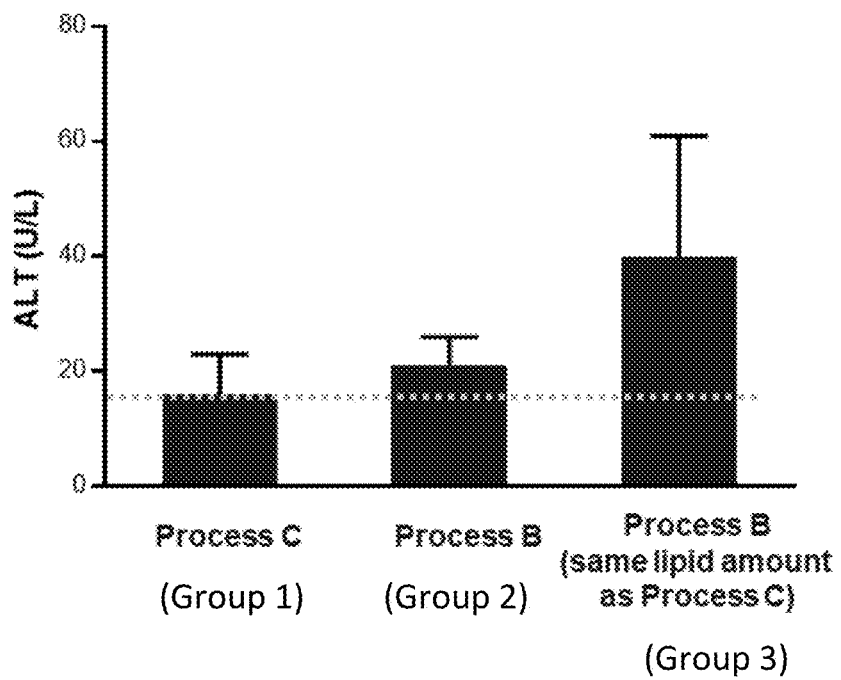
FIG. 4B is an exemplary graph that compares the tolerability of mRNA-LNPs prepared by Process B and Process C. To compare tolerability of mRNA-LNPs prepared by Process B versus Process C, the amount of mRNA-LNP administered to mice was adjusted by the amount of mRNA or lipids.

Liver enzyme ALT was measured in the same groups of mice at 6 hours after administration of the mRNA-LNPs (FIG. 4B). As shown previously, Group 1 and Group 2 mice showed slightly lower levels of ALT expression, even though Group 1 mice received higher levels of liposomal components in the mRNA-LNP composition than Group 2 mice. Surprisingly, Group 1 mice exhibited significantly lower ALT than Group 3 mice, in spite of the fact that both groups received mRNA-LNPs comprising the same amount of total lipids. Notably the lipid components of Group 1 and Group 3 mice were also identical.

Taken together, the data in these Examples show that there can be substantial advantages in using the mRNA-LNP composition prepared by the present invention (Process C). The mRNA-LNPs made by Process C shows higher potency and higher or comparable tolerability than mRNA-LNPs made by Process B.

Example 5. Higher Potency mRNA-LNP Formed by Process C as Compared to Process B with No Corresponding Loss of Tolerability This example shows that mRNA-LNPs made according to the present invention using Process C provides higher in vivo expression and higher potency with comparable in vivo tolerability. Liver aspartate transaminase (AST) and aminotransferase (ALT) levels are typically measured as determinants for tolerability in response to a drug; the higher the expression is in the liver, the lower the level of tolerability.

Figure 5A:
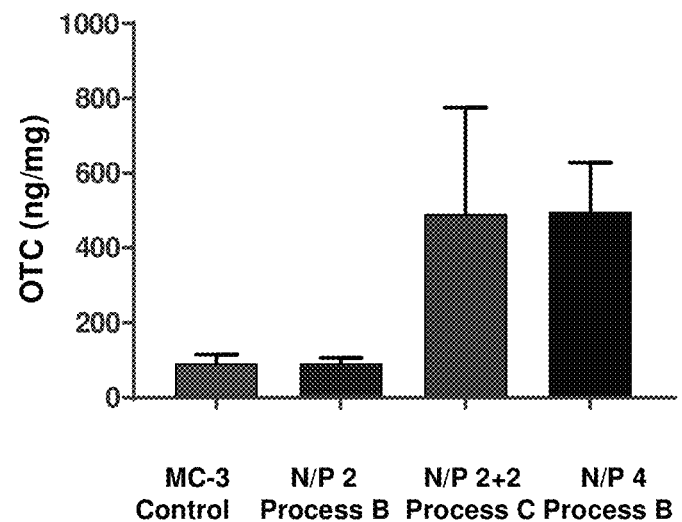
FIG. 5A is an exemplary graph that compares in vivo potency of mRNA-LNPs prepared by Process B and Process C. Human OTC expression in serum of mice was measured after the administration of mRNA LNPs at comparable amounts of mRNA and lipid.

In this example, mice were administered a single intravenous dose of human OTC mRNA encapsulated in lipid nanoparticles prepared by Process B or C, as described in Example 1. Liver homogenate and serum were collected from these mice at 24 hours and analyzed for human OTC protein levels and ALT/AST levels, respectively. As shown in FIG. 5A, mRNA-LNPs prepared by Process C produced higher OTC expression compared to that produced by Process B. Specifically, a lipid:mRNA content i.e. N/P ratio of N/P 2+2 Process C (whereby "N/P 2+2" refers to the cumulative N/P ratio of LNPs at the end of step (a) (N/P ratio=2) and step (b) (N/P ratio=4) of FIG. 1 as a result of adding more "N" in the form of empty LNPs), there was higher expression than at an N/P ratio of 2 ("N/P 2") Process B (N/P ratio of LNPs from step (a) only of FIG. 1). This is surprising because the N/P 2+2 Process C preparation contains the same amount of mRNA as the N/P 2 Process B preparation. In other words, merely by adding additional empty LNPs, the same amount of total mRNA resulted in more protein being expressed. The expression of OTC at N/P 2+2 Process C was comparable to N/P 4 Process B, but as explained below, there was no corresponding loss in tolerability with N/P 2+2 Process C as seen in N/P Process B. Thus, although both formulations contained the same amount of lipids (and mRNA), adding part of the lipids as empty LNPs improved tolerability without affecting potency.

Figure 5B:
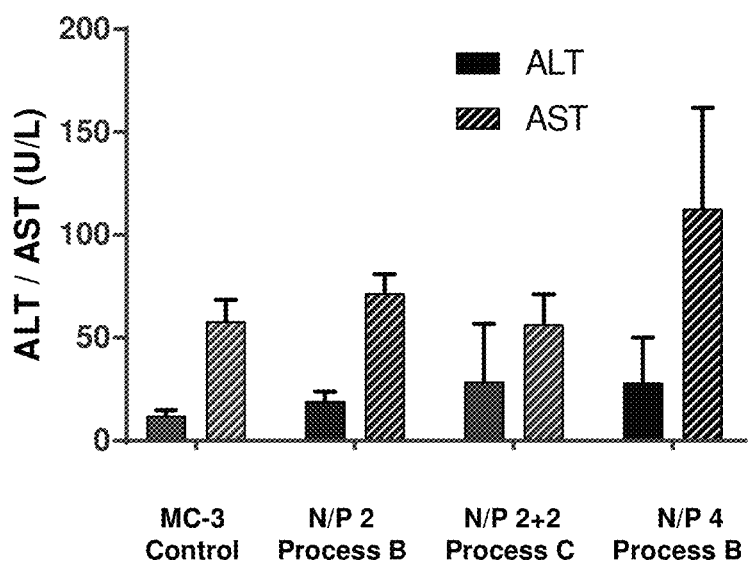
FIG. 5B is an exemplary graph that compares in vivo tolerability of mRNA-LNPs prepared by Process B and Process C. The level of liver enzymes, AST and ALT, were measured after the administration of mRNA-LNPs prepared by the Process B or Process C at comparable amounts of mRNA and lipid.

Mice were sacrificed at 24 hours post-administration and levels of liver enzymes AST and ALT were determined. As shown in FIG. 5B, AST levels in mice administered with mRNA-LNPs prepared by Process C were lower than that in mice administered with mRNA-LNPs prepared by Process B as demonstrated by a comparison between N/P 2+2 Process C and N/P 4 Process B. The AST level in mice administered with mRNA-LNPs with the cationic lipid cHSe prepared at a cumulative N/P ratio of 4 (2+2) by Process C was comparable to the AST levels induced by (i) LNPs with the same cationic lipid at a N/P ratio of 2 prepared by Process B and (ii) MC-3 control LNPs. Of note, LNPs prepared by Process C at a cumulative N/P ratio of 4 (2+2) showed higher tolerability (i.e. lower AST levels) than LNPs prepared by Process B at an N/P ratio of 4. These data indicate that the mRNA-LNPs prepared by Process C are better or comparable in terms of tolerability to that of Process B, while resulting in higher expression of the mRNA-encoded protein.

These data indicate higher expression of the mRNA-encoded protein in vivo when the mRNA-LNP compositions were formed by Process C of the present invention.

Example 6. High Potency mRNA-LNP with High Tolerability Formed by Process C as Compared to Process B This example shows that mRNA-LNPs made according to the present invention using Process C provides higher in vivo expression and higher potency with high in vivo tolerability. Liver aspartate transaminase (AST) and aminotransferase (ALT) levels are typically measured as determinants for tolerability in response to a drug; the higher the expression is in the liver, the lower the level of tolerability.

Figure 6A:
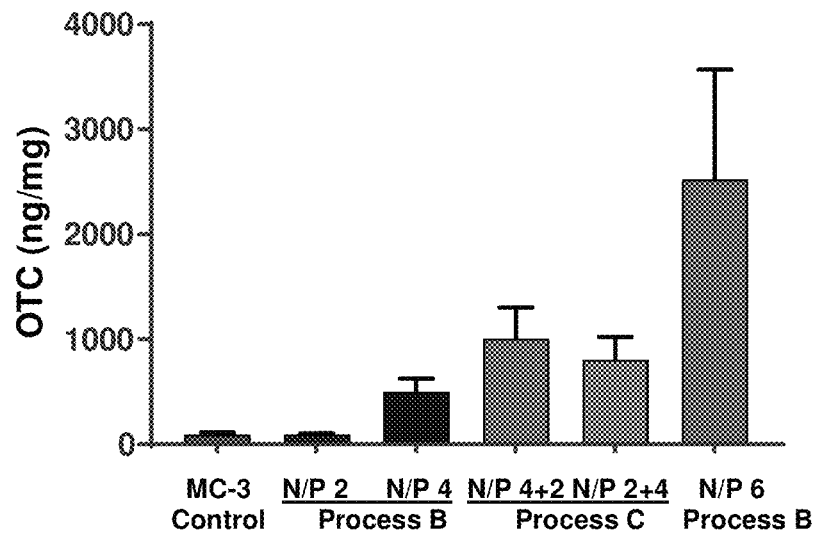
FIG. 6A is an exemplary graph that compares in vivo potency of mRNA-LNPs prepared by Process B and Process C at comparable lipid:mRNA ratios. A comparison is also provided between Process C-derived LNPs that achieved an equivalent cumulative lipid to mRNA ratio (N/P ratio) through preparations with interchangeable lipid to mRNA content derived from either step (a) or step (b) of FIG. 1.

In this example, mice were administered a single intravenous dose of human OTC mRNA encapsulated in lipid nanoparticles prepared by Process B or C, as described in Example 1. The mRNA LNPs were prepared comprising varying proportions of lipid:mRNA content i.e. N/P ratios. Liver homogenate and serum were collected from these mice at 24 hours and analyzed for human OTC protein levels and ALT/AST levels, respectively. As shown in FIG. 6A, mRNA-LNPs prepared by Process C resulted in higher OTC expression compared to LNPs produced by Process B at comparable N/P ratios.

It is observed that OTC mRNA expression increases as the N/P ratio is increased from 2 to 4 to 6 with a Process B preparation (i.e., as more lipid is added while keeping the amount of mRNA the same). In a Process C preparation, an N/P ratio of 4 (in step (a) of FIG. 1) and an N/P ratio of 2 (in step (b) of FIG. 1) resulted in higher OTC expression as compared to Process B preparations at an N/P ratio of 2 or an N/P ratio of 4. Similarly, a Process C preparation with an N/P of 2 (in step (a) of FIG. 1) and an N/P of 4 (in step (b) of FIG. 1) also resulted in higher OTC expression as compared to Process B preparations at N/P 2 or 4. The cumulative N/P ratio of the Process C preparations was 6, and both preparations achieved comparable levels of mRNA expression. Thus, a cumulative N/P ratio of 6 achieved in a Process C preparation either by N/P 4+2 or by N/P 2+4 resulted in higher mRNA expression than achieved by LNPs prepared by Process B at N/P of 2 or 4. Interestingly, neither Process C preparation achieved mRNA expression levels as high as an N/P of 6 prepared by Process B, suggesting that in some instances optimizing the N/P ratio during mixing of empty LNPs with mRNA can result in LNPs formulations with increased potency. Without wishing to be bound by any particular theory, this could be due to an excess of empty LNPs resulting from the chosen N/P ratio. In other words, the resulting LNP formulation may be somewhat similar in composition to LNP formulations prepared by process C, although seemingly without the advantages in tolerability (see below).

Figure 6B:
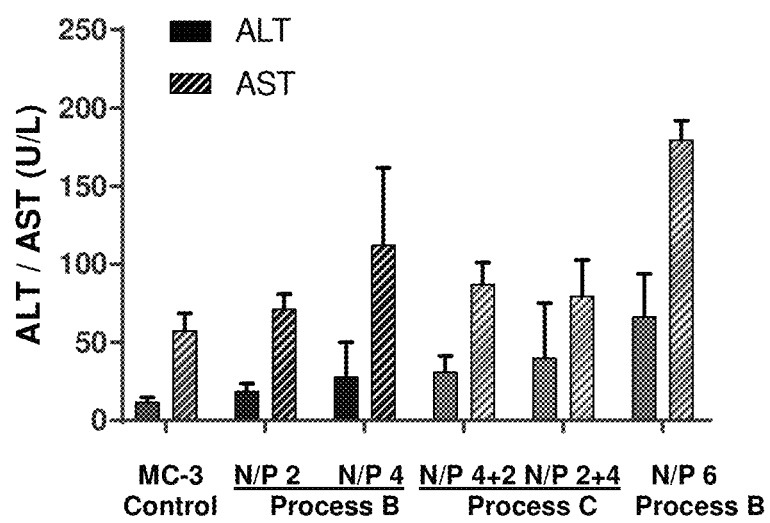
FIG. 6B is an exemplary graph that compares in vivo tolerability of mRNA-LNPs prepared by Process B and Process C. The level of liver enzymes, AST and ALT, were measured after the administration of mRNA-LNPs prepared by the Process B or Process C at comparable amounts of mRNA and lipid.

Mice were sacrificed at 24 hours post-administration and levels of liver enzymes AST and ALT were determined. As shown in FIG. 6B, in mice administered with LNPs at lipid:mRNA content i.e. N/P ratio of N/P 4 or N/P 6 prepared by Process B, the AST levels are high, indicative of low tolerability. In contrast, mice administered with the LNPs prepared by Process C (interchangeably N/P 4+2 or N/P 2+4) exhibited lower AST levels, indicative of high tolerability as compared to Process B N/P 4 or 6 preparations, and of comparable tolerability as LNP N/P 2 preparations prepared by Process B and MC-3 control LNPs. The data also indicate that the LNP N/P ratios in Process C are interchangeable in the two steps of the process and result in similar outcomes.

Overall, these data indicate higher expression of the mRNA-encoded protein in vivo was achieved with Process C preparations of this invention concomitant with high tolerability. The tolerability was greater than Process B LNPs preparations of comparable cumulative N/P ratios.

Example 7. High Potency mRNA-LNP Comprising Two Lipids Formed by Process C Showed High Tolerability as Compared to Process B LNPs Comprising a Single Lipid This example shows that mRNA-LNPs made according to the present invention using Process C that comprise a combination of LNPs prepared with the cHSe-E lipid in combination with LNPs prepared with the ML-2 lipid provide higher in vivo expression and higher potency with higher in vivo tolerability as compared to LNPs with cHSe lipid alone prepared by Process B. This demonstrates that the benefit of adding empty LNPs can be provided by LNPs that are different in composition from the LNP encapsulating the mRNA. Liver aspartate transaminase (AST) and aminotransferase (ALT) levels are typically measured as determinants for tolerability in response to a drug; the higher the expression is in the liver, the lower the level of tolerability.

In this example, mice were administered a single intravenous dose of human OTC mRNA encapsulated in lipid nanoparticles prepared by Process B or C, as described in Example 1. In this example, mRNA encoding EPO was encapsulated into lipid nanoparticles comprising the cationic lipid cHSe. Empty lipid nanoparticles were prepared with the cationic lipid ML-2.

Figure 7A:
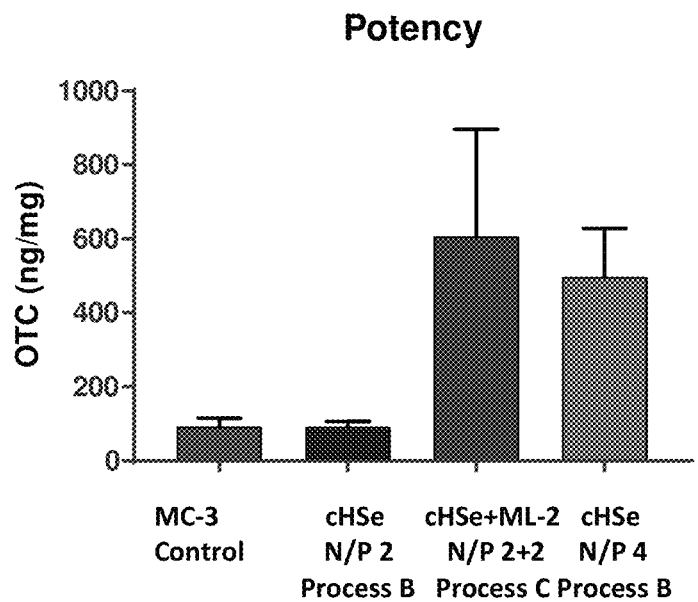
FIG. 7A is an exemplary graph that compares in vivo potency of mRNA-LNPs prepared by Process B and Process C at comparable lipid:mRNA ratio. Human OTC expression in serum of mice was measured after the administration of mRNA LNPs comprising a cHSe as the cationic lipid prepared by the Process B or Process C, or a combination of mRNA-encapsulating LNPs with cHSe as the cationic lipid and LNPs with ML-2 as the cationic lipid prepared by Process C at comparable amounts of mRNA and total lipid.

Liver homogenate and serum were collected from these mice at 24 hours and analyzed for human OTC protein levels and also ALT/AST, respectively. As shown in FIG. 7A, mRNA-LNPs prepared by Process C comprising a combination of cHSe-based LNPs and ML-2-based LNPs resulted in higher OTC expression compared to LNPs produced by Process B at N/P ratios of 2 or 4.

Figure 7B:
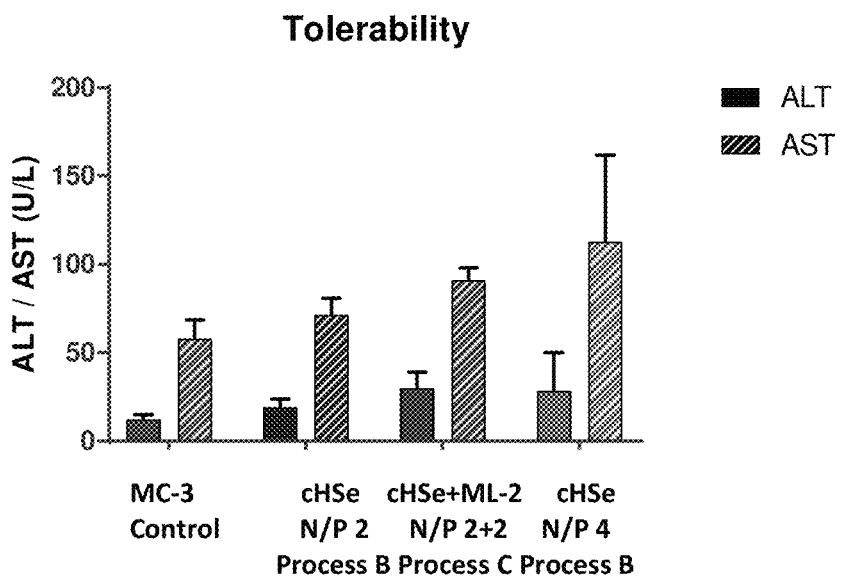
FIG. 7B is an exemplary graph that compares in vivo tolerability of mRNA-LNPs prepared by Process B and Process C. The level of liver enzymes, AST and ALT, were measured after the administration of mRNA-LNPs comprising a cHSe as the cationic lipid prepared by the Process B or Process C or a combination of mRNA-encapsulating LNPs with cHSe as the cationic lipid and empty LNPs containing ML-2 as the cationic lipid prepared by Process C at comparable amounts of mRNA and total lipid.

As shown in FIG. 7B, tolerability was observed as indicated by lower AST levels in mice administered LNPs comprising a combination of cHSe-based LNPs and ML-2-based LNPs, each at an N/P ratio of 2, cumulatively resulting in LNP formulation with an N/P ratio of 4 prepared by Process C, in comparison to cHSe-based LNPs prepared by Process B at an N/P ratio of 4. The tolerability of the LNPs prepared by Process C was comparable to the tolerability of a Process B preparation at an N/P ratio of 2 comprising cHSe-based LNPs, but which had much lower potency.

Overall, these data indicate higher expression of the mRNA-encoded protein in vivo was achieved with Process C preparations of this invention comprising a combination of two different LNPs (one set of LNPs encapsulating the mRNA, and another set of empty LNPs prepared with a different cationic lipid), with higher tolerability as compared to Process B LNPs preparations comprising a single lipid of comparable N/P ratio and comparable potency. Potency was increased in a Process C preparation by using a combination of two different LNP formulations and achieved comparable tolerability as a Process B LNP with a lower N/P ratio.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

We claim:
1. A method of manufacturing a composition comprising lipid nanoparticles encapsulating mRNA (mRNA-LNPs), the method comprising
  (a) mixing preformed empty lipid nanoparticles (LNPs) with mRNA under conditions that allow formation of mRNA-LNPs; and
  (b) combining the mRNA-LNPs formed in step (a) with an amount of preformed empty LNPs at a ratio of 20:1 to 1:20 mRNA-LNPs to preformed empty LNPs to increase the potency or tolerability of the mRNA-LNPs in vivo as compared to a composition comprising identical mRNA-LNPs but without the empty LNPs, resulting in the composition comprising the mRNA-LNPs and the empty LNPs, wherein the LNPs have an average size ranging from about 50-150 nm in diameter.
2. A method of manufacturing a composition comprising lipid nanoparticles encapsulating mRNA (mRNA-LNPs), the method comprising:
  (a) mixing preformed empty lipid nanoparticles (LNPs) with mRNA at a lipid:mRNA content that allows formation of mRNA-LNPs having an N/P ratio of about 2; and
  (b) combining the mRNA-LNPs formed in step (a) with preformed empty LNPs, resulting in the composition comprising the mRNA-LNPs and the empty LNPs having a cumulative N/P ratio of about 4, wherein the resulting composition has increased potency or tolerability in vivo as compared to a composition comprising identical mRNA-LNPs but without the empty LNPs.

* * * * *